US006831171B2

(12) United States Patent
Breaker et al.

(10) Patent No.: US 6,831,171 B2
(45) Date of Patent: Dec. 14, 2004

(54) NUCLEIC ACID CATALYSTS WITH ENDONUCLEASE ACTIVITY

(75) Inventors: Ronald Breaker, Guilford, CT (US); Leonid Beigelman, Longmont, CO (US)

(73) Assignees: Yale University, New Haven, CT (US); Sirna Therapeutics, Inc., Boulder, CO (US)

(*) Notice: Subject to any disclaimer, the term of this patent is extended or adjusted under 35 U.S.C. 154(b) by 0 days.

(21) Appl. No.: 09/780,929

(22) Filed: Feb. 8, 2001

(65) Prior Publication Data

US 2002/0151693 A1 Oct. 17, 2002

Related U.S. Application Data

(60) Provisional application No. 60/181,360, filed on Feb. 8, 2000.

(51) Int. Cl.[7] .............................................. C07H 21/04
(52) U.S. Cl. ......................... 536/24.5; 435/6; 435/325; 435/375; 536/23.1; 536/24.1; 514/44
(58) Field of Search ............................... 536/24.5, 23.1, 536/24.1; 435/6, 325, 375, 91.31, 320.1; 514/44

(56) References Cited

U.S. PATENT DOCUMENTS

| 5,334,711 A | 8/1994 | Sproat et al. |
| 5,624,803 A | 4/1997 | Noonberg et al. |
| 5,854,038 A | 12/1998 | Sullenger et al. |

FOREIGN PATENT DOCUMENTS

| WO | WO8902439 | 3/1989 |
| WO | WO9103162 | 3/1991 |
| WO | WO9207065 | 4/1992 |
| WO | WO9315187 | 8/1993 |
| WO | WO9323569 | 11/1993 |
| WO | WO9402595 | 2/1994 |
| WO | WO9506731 | 3/1995 |
| WO | WO9511910 | 5/1995 |
| WO | WO9610390 | 4/1996 |
| WO | WO9610391 | 4/1996 |
| WO | WO9610392 | 4/1996 |
| WO | WO9618736 | 6/1996 |
| WO | WO9726270 | 7/1997 |
| WO | WO9843993 | 10/1998 |
| WO | WO 99/16871 | 4/1999 |
| WO | WO 99/54459 | 10/1999 |

OTHER PUBLICATIONS

Agrawal et al., TIBTECH 1996. 14:376–380.*
Gewirtz et al., 1996. Proc. Natl. Acad. Sci. v 93, pp. 3161–3163.*
Braasch, D. A. Biochemistry. Apr. 2002; 41(14): 4503–4510.*
Branch, A. D., (1998).Trends Biochem Sci. Feb. 1998;23(2):45–50.*
Tamm, I. et al. The Lancet Aug. 2001, 358: 489–497.*
Castanotto et al., "Intracellular Expression and Function of Antisense Catalytic RNAs," Methods Enzymol, 313:401–20, 2000.
Breaker et al., "In vitro Selection of Catalytic Polynucleotides," Chemical Reviews 97:371–390 (1997).
Breaker et al., "In vitro Selection of Self–Cleaving Ribozymes and Deoxyribozymes," Horizon Scientific Press 1–19 (1999).
Bartel and Szostak, "Isolation of New Ribozymes From a Large Pool of Random Sequences," Science 261:1411–1418 (1993).
Beaucage and Iyer, "The Functionalization of Oligonucleotides Via Phosphoramidite Derivatives," Tetrahedron 49:1925–1963 (1993).
Beaudry and Joyce, "Directed Evolution of an RNA Enzyme," Science 257:635–641 (1992).
Beaudry and Joyce, "Minimum Secondary Structure Requirements for Catalytic Activity of a Self–Splicing Group I Intron," Biochemistry 29:6534–5639 (1990).
Been et al., "Secondary Structure of the Self–Cleaving RNA of Hepatitis Delta Virsus: Applications to Catalytic RNA Design," Biochemistry 31:11843–11852 (1992).
Beigelman et al., "Chemical Modification of Hammerhead Ribozymes," J. Biol. Chem. 270:25702–25708 (1995).
Beigelman et al., "Synthesis of 1–Deoxy–D–Ribofuranose Phosphoramidite & The Incorporation of Abasic Nucleotides in Stem–Loop II of a Hammerhead Ribozyme," Bioorganic & Medicinal Chemistry Letters 4:1715–1720 (1994).
Bellon et al., "Amino–Linked Ribozymes: Post–Synthetic Conjugation of Half–Ribozymes," Nucleosides & Nucleotides 16:951–954 (1997).
Bellon et al., "Post–synthetically Ligated Ribozymes: An Alternative Approach to Iterative Solid Phase Synthesis," Bioconjugate Chem. 8:204–212 (1997).
Benseler et al., "Hammerhead–like Molecules Containing Non–Nucleoside Linkers Are Active RNA Catalysts," J. Am. Chem. Soc. 115:8483–8484 (1993).
Breaker and Joyce, "Inventing and improving ribozyme function: rational design versus iterative selection methods," TIBTECH 12:268–275 (1994).
Breaker, "Are engineered proteins getting competition from RNA?" Current Opinion in Biotechnology 7:442–448 (1996).
Burgin et al., "Chemically Modified Hammerhead Ribozymes with Improved Catalytic Rates," Biochemistry 35:14090–14097 (1996) (volume no mistakenly listed as 6).
Castanotto et al., Methods Enzymol, 313:401–20, 2000.
Cech, "Ribozyme Engineering," Current Opinion in Structural Biology 2:605–609 (1992).

(List continued on next page.)

Primary Examiner—Sean McGarry
Assistant Examiner—James D. Schultz
(74) Attorney, Agent, or Firm—Needle & Rosenberg, P.C.

(57) ABSTRACT

The present invention relates to novel Nucleic acid catalysts, methods of synthesis, and uses thereof.

34 Claims, 8 Drawing Sheets

OTHER PUBLICATIONS

Cech, "Ribozymes and Their Medical Implications," *JAMA* 260:3030–3034 (1988).

Chen et al., "Multitarget–Ribozyme Directed to Cleave at up to Nine Highly Conserved HIV–1 env RNA Regions Inhibits HIV–1 Replication–Potential Effectiveness Against Most Presently Sequenced HIV–1 Isolates," *Nucleic Acids Research* 20:4581–4589 (1992).

Chorwira and Burke, "Extensive Phosphorothioate Substitution Yields Highly Active and Nuclease–Resistant Hairpin Ribozymes," *Nucleic Acids Research* 20:2835–2840 (1992).

Chowrira et al., "In Vitro and in Vivo Comparison of Hammerhead, Hairpin, and Hepatitis Delta Virus Self–Processing Ribozyme Cassettes," *J. Biol. Chem.* 269:25856–25864 (1994).

Christoffersen and Marr, "Riobozymes as Human Therapeutic Agents," *J. Med. Chem.* 38:2023–2037 (1995) (also referred to as Christofferson and Marr).

Cload and Schepartz, "Polyether Tethered Oligonucleotide Probes," *J. Am. Chem. Soc.* 113:6324–6326 (1991).

Couture and Stinchcomb, "Anti–gene therapy: the use of ribozymes to inhibit gene function," *Trends In Genetics* 12:510–515 (1996).

Dropulic et al., "Functional Characterization of a U5 Ribozyme: Intracellular Suppression of Human Immunodeficiency Virus Type I Expression," *Journal of Virology* 66:1432–1441 (1992).

Durand et al., "Circular Dichroism Studies of an Oligodeoxyribonucleotide Containing a Hairpin Loop Made of a Hexaethylene Glycol Chain: Conformation and Stability," *Nucleic Acids Research* 18:6353–6359 (1990).

Elroy–Stein and Moss, "Cytoplasmic Expression System Based on Constitutive Synthesis of Bacteriophage T7 RNA Polymerase in Mammalian Cells," *Proc. Natl. Acad. Sci. USA* 87:6743–6747 (1990).

Fedor and Uhlenbeck, "Kinetics of Intermolecular Cleavage by Hammerhead Ribozymes," *Biochemistry* 31:12042–12054 (1992).

Ferentz and Verdine, "Disulfied Cross–Linked Oligonucleotides," *J. Am. Chem. Soc.* 113:4000–4002 (1991).

Forster and Symons, "Self–Cleavage of Plus and Minus RNAs of a Virusoid and a Structural Model for the Active Sites," *Cell* 49:211–220 (1987).

Freier et al., "Improved free–energy parameters for predictions of RNA duplex stability," *Proc. Natl. Acad. Sci. USA* 83:9373–9377 (1986).

Gao and Huang, "Cytoplasmic Expression of a Reporter Gene by Co–Delivery of T7 RNA Polymerase and T7 Promoter Sequence with Cationic Liposomes," *Nucleic Acids Research* 21:2867–2872 (1993).

Gold et al., Diversity of Oligonucleotide Functions, *Annu. Rev. Biochem.* 64:763–797 (1995).

Good et al., "Expression of small, therapuetic RNAs in human nuclei," *Gene Therapy* 4:45–54 (1997).

Guo and Collins, "Efficient trans–cleavage of a stem–loop RNA substrate by a ribozyme derived from Neurospora VS RNA," *EMBO J.* 14:368–376 (1995).

Hendry et al., "Using linkers to investigate the spatial separation of the conserved nucleotides $A_g$ and $G_{12}$ in the Hammerhead Ribozyme," *Biochimica et Biophysica Acta* 1219:405–412 (1994).

Hertel et al., "Numbering System for the Hammerhead," *Nucleic Acids Research* 20:3252 (1992).

Hunziker et al., "Nucleic Acid Analogues: Synthesis and Properties, in Modern Synthetic Methods," *VCH*, 331–417, 1995.

Ishiwata et al., "Physical–Chemistry Characteristics and Biodistribution of Poly(ethylene glycol)–Coated Liposomes Using Poly(oxyethylene) Cholesteryl Ether," *Chem. Pharm. Bull.* 43:1005–1011 (1995) (mistakenly referred to as Ishiwataet).

Izant and Weintraub, "Constitutive and Conditional Suppression of Exogenous and Endogeneous Genes by Anti-Sense RNA," *Science* 229:345–352 (1985).

Jaschke et al., "Automated Incorporation of Polyethylene Glycol into Synthetic Oligonucleotides," *Tetrahedron Letters* 34:301–304 (1993).

Jeffries and Symons, "A Catalytic 13–mer Ribozyme," *Nucleic Acids Research* 17:1371–1377 (1989) (also referred to as Jefferies).

Joseph and Burke, "Optimization of an Anti–HIV Hairpin Ribozyme by in Vitro Selection," *J. Biol. Chem.* 268:24515–24518 (1993).

Joyce et al., "Amplification, mutation and selection of catalytic RNA," *Gene* 82:83–87 (1989).

Joyce, "Directed Molecular Evolution," *Scientific American* 267:90–97 (1992).

Kashani–Sabet et al., "Reversal of the Malignant Phenotype by an Anti–ras Ribozyme," *Antisense Research & Development* 2:3–15 (1992).

Kumar and Ellington, "Artificial evolution and natural ribozymes," *FASEB J.* 9:1183–1195 (1995).

Lasic and Needham "The 'Stealth' Liposome: A Prototypical Biomaterial," *Chemical Reviews* 95:2601–2627 (1995).

Lasic and Papahadjopoulos, "Liposomes Revisited," *Science* 267:1275–1276 (1995).

L'Huillier et al., "Cytoplasmic Delivery of Ribozymes Leads to Efficient Reduction in α–Lactalbumin mRNA Levels in C1271 Mouse," *EMBO J.* 11:4411–4418 (1992).

Li and Breaker, "Kinetics of RNA Degradation by Specific Base Catalysis of Transesterification Involving the 2'–Hydroxyl Group" 1999, *J. Am. Chem. Soc.*, 121, 5364–5372.

Lieber et al., "Stable High–Level Gene Expression in Mammalian Cells by T7 Phage RNA Polymerase," *Methods Enzymol.* 217:47–66 (1993).

Limbach et al., "Summary: the modified nucleosides of RNA," *Nucleic Acids Research* 22(12):2183–2196 (1994).

Lisziewicz et al., "Inhibition of Human Immunodeficiency Virus Type 1 Replication by Regulated Expression of a Polymeric Tat Activation Response RNA Decoy as a Strategy for Gene Therapy in AIDS," *Proc. Natl. Acad. Sci. U.S.A.* 90:8000–8004 (1993).

Liu et al., "Cationic Liposome–mediated Intravenous Gene Delivery," *J. Biol. Chem.* 270(42):24864–24870 (1995).

Long and Uhlenbeck, "Kinetic characterization of intramolecular and intermolecular hammerhead RNAs with stem II deletions," *Proc. Natl. Acad. Sci. USA* 91:6977–6981 (1994).

Ma et al., "Design and Synthesis of RNA Miniduplexes via a Synthetic Linker Approach," *Biochemistry* 32:1751–1758 (1993).

Ma et al., "Design and Synthesis of RNA Miniduplexes via a Synthetic Linker Approach. 2. Generation of Covalently Closed, Double–Stranded Cyclic HIV–1 TAR RNA Analogs with High Tat–Binding Affinity," *Nucleic Acids Research* 21:2585–2589 (1993).

McCall et al., "Minimal sequence requirements for ribozyme activity," *Proc. Natl. Acad. Sci. USA* 89:5710–5714 (1992).

McCurdy et al., "Deoxyoligonucleotides with Inverted Polarity: Synthesis and Use in Triple–Helix Formation" *Nucleosides & Nucleotides* 10:287–290 (1991).

McGarry and Lindquist, "Inhibition of heat shock protein synthesis by heat–inducible antisense RNA," *Proc. Natl. Acad. Sci. USA* 83:399–403 (1986).

Michels and Pyle, "Conversion of a Group II intron into a New Multiple–Turnover Ribozyme that Selectively Cleaves Oligonucleotides: Elucidation of Reaction Mechanism and Structure/Function Relationships," *Biochemistry* 34:2965–2977 (1995).

Milligan and Uhlenbeck, "Synthesis of Small RNAs Using T7 RNA Polymerase," *Methods Enzymol* 180:51–62 (1989).

Moore and Sharp, "Site–Specific Modification of Pre–mRNA: The 2'Hydroxyl Groups at the Splice Sites," *Science* 256:992–996 (1992).

Nathans and Smith, "Restriction Endonucleases in the Analysis and Restructuring of DNA Molecules," *Ann. Rev. Biochem.* 44:273–293 (1975).

Noonberg et al., In vivo generation of highly abundant sequence-specific oligonucleotides for antisense and triplex gene regulation *Nucleic Acids Research* 22(14):2830–2836 (1994).

Ohkawa et al., "Activities of HIV–RNA Targeted Ribozymes Transcribed From a 'Shot–Gun' Type Ribozyme–trimming Plasmid," *Nucleic Acids Symp. Ser.* 27:15–16 (1992).

Ojwang et al., "Inhibition of Human Immunodeficiency Virus Type 1 Expression by a Hairpin Ribozyme," *Proc. Natl. Acad. Sci. USA* 89:10802–10806 (1992).

Oku et al., "Real–time analysis of liposomal trafficking in tumor–bearing mice by use of positron emission tomography," *Biochimica et Biophysica Acta* 1238:86–90 (1995).

Ono et al., "DNA Triplex Formation of Oligonucleotide Analogues Consisting of Linker Groups and Octamer Segments That Have Opposite Sugar–Phosphate Backbone Polarities," *Biochemistry* 30:9914–9921 (1991).

Orgel, "Selection in vitro," *Proc. R. Soc. London B.* 205:435–442 (1979).

Pan et al., "Properties of an In Vitro Selected Pb$^{2+}$ Cleavage Motif," *Biochemistry* 33:9561–9565 (1994).

Perreault et al., "Mixed Deoxyribo– and Ribo–Oligonucleotides with Catalytic Activity," *Nature* 344:565–567 (1990) (often mistakenly listed as Perrault).

Pieken et al., "Kinetic Characterization of Ribonuclease–Resistant 2'–Modified Hammerhead Ribozymes," *Science* 253:314–317 (1991).

Richardson and Schepartz, "Tethered Oligonucleotide Probes. A Strategy for the Recognition of Structured RNA," *J. Am. Chem. Soc.* 113:5109–5111 (1991).

Rossi et al., *Science*, 285, 1685, 1999.

Ruffner et al., "Sequence Requirements of the Hammerhead RNA Self–Cleavage Reaction," *Biochemistry* 29:10695–10702 (1990).

Sarver et al., "Ribozymes as Potential Anti–HIV–1 Therapeutic Agents" *Science* 247:1222–1225 (1990).

Scanlon et al., "Ribozyme–Mediated Cleavage of c–fos mRNA Reduces Gene Expression of DNA Synthesis Enzymes and Metallothionein," *Proc. Natl. Acad. Sci. USA* 88:10591–10595 (1991).

Scaringe et al., "Chemical synthesis of biologically active oligoribonucleotides using β–cyanoethyl protected ribonucleoside phosphoramidites," *Nucl Acids Res.* 18:5433–5441 (1990).

Seela and Kaiser, "Oligodeoxyribonucleotides containing 1.3–propanediol as nucleoside substitute," *Nucleic Acids Research* 15:3113–3129 (1987).

Shabarova et al., "Chemical ligation of DNA: The first non–enzymatic assembly of a biologically active gene," *Nucleic Acids Research* 19:4247–4251 (1991).

Soukup and Breaker, "Relationship between internucleotide linkage geometry and the stability of RNA" 1999, *RNA*, 5, 1308–1325.

Sugiyama et al., "Catalytic activities of hammerhead ribozymes with a triterpenoid linker instead of stem/loop II," *FEBS Letters* 392:215–219 (1996).

Sullenger and Cech, "Tethering Ribozymes to a Retroviral Packaging Signal for Destruction of Viral RNA," *Science* 262:1566–1569 (1993).

Szostak and Ellington, "Ch. 20—In Vitro Selection of Functional RNA Sequences," in *The RNA World*, edited by Gesteland and Atkins, Cold Spring Harbor Laboratory Press, pp. 511–533 (1993).

Szostak, "In Vitro Genetics," *TIBS* 17:89–93 (1992).

Taira et al., "Construction of a novel RNA–transcript–trimming plasmid which can be used both in vitro in place of run–off and (G)–free transcriptions and in vivo as multi–sequences transcription vectors," *Nucleic Acids Research* 19:5125–5130 (1991).

Tang and Breaker, "Examination of the catalytic fitness of the hammerhead ribozyme by in vitro selection," *RNA* 3:914–925 (1997).

Thompson et al., "Improved accumulation and activity of ribozymes expressed from a tRNA–based RNA polymerase III promoter," *Nucleic Acids Research* 23:2259–2268 (1995).

Thomson et al., "In vitro selection of hammerhead ribozymes containing a bulged nucleotide in stem II," *Nucleic Acids Research* 24:4401–4406 (1996) (May Be Referred to as Thompson).

Turner et al., "Improved Parameters for Prediction of RNA Structure," *Cold Spring Harbor Symposia on Quantitative Biology* vol. LII, pp. 123–133 (1987).

Turner et al., "Free Energy Increments for Hydrogen Bonds in Nucleic Acid Base Pairs," *J. Am. Chem. Soc.* 109:3783–3785 (1987).

Usman and Cedergren, "Exploiting the chemical synthesis of RNA," *TIBS* 17:334–339 (1992).

Usman and McSwiggen, "Ch. 30—Catalytic RNA (Ribozymes) as Drugs," *Annual Reports in Medicinal Chemistry* 30:285–294 (1995).

Usman et al., "Automated Chemical Synthesis of Long Oligoribonucleotides Using 2'–O–Silylated Ribonucleoside 3'–O–Phosphoramidites on a Controlled–Pore Glass Support: Synthesis of a 43–Nucleotide Sequence Similar to the 3'–Half Molecule of an *Escherichia coli* Formylmethoionine tRNA," *J. Am. Chem. Soc.* 109:7845–7854 (1987).

Usman et al., "Chemical modification of hammerhead ribozymes: activity and nuclease resistance," *Nucleic Acids Symposium Series* 31:163–164 (1994).

Vaish et al., "In vitro selection of a purine nucleotide–specific hammerhead–like ribozyme," *Proc. Natl. Acad. Sci. USA* 95:2158–2162 (1998).

Ventura et al., "Activation of HIV–Specific Ribozyme Activity by Self–Cleavage," *Nucleic Acids Research* 21:3249–3255 (1993).

Weerasinghe et al., "Resistance to Human Immunodeficiency Virus Type 1 (HIV–1) Infection in Human CD4+ Lymphocyte–Derived Cell Lines Conferred by Using Retroviral Vectors Expressing an HIV–1 RNA–Specific Ribozyme," *Journal of Virology* 65:5531–5534 (1994).

Wincott et al., "Synthesis, deprotection, analysis and purification of RNA and ribozymes," *Nucleic Acids Research* 23(14):2677–2684 (1995).

Wincott et al., "A Practical Method for the Production of RNA and Ribozymes," *Methods in Molecular Biology* 74:59–69 (1997).

Yu et al., "A Hairpin Ribozyme Inhibits Expression of Diverse Strains of Human Immunodeficiency Virus Type 1," *Proc. Natl. Acad. Sci. USA* . 90:6340–6344 (1993).

Zaug et al., "The Tetrahymena Ribozyme Acts Like an RNA Restriction Endonuclease," *Nature* 324:429–433 (1986).

Zhou et al., "Synthesis of Functional mRNA in Mammalian Cells by Bacteriophage T3 RNA Polymerase," *Mol. Cell. Biol.* 10:4529–4537 (1990).

Zuker, "On Finding All Suboptimal Foldings of an RNA Molecule," *Science* 244:48–52 (1989).

* cited by examiner (SEQ ID NO 102)

Figure 3
A
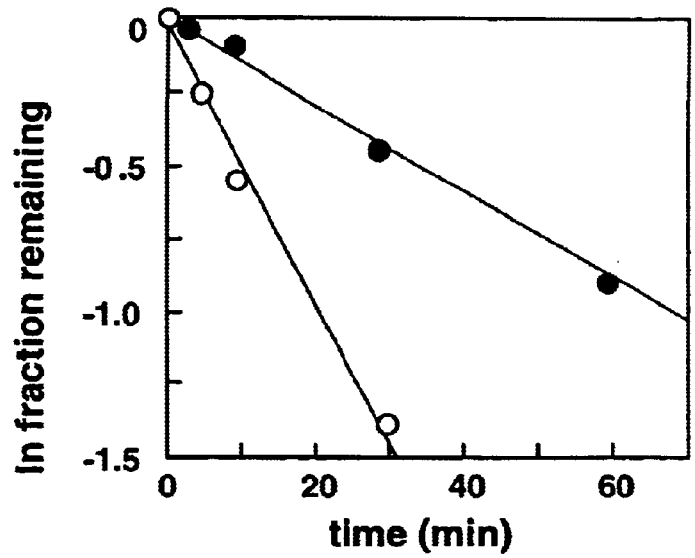
B
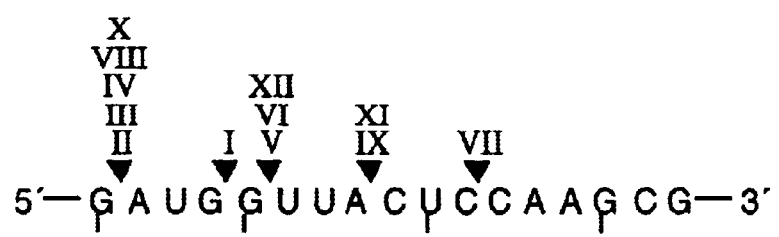
(SEQ ID NO 116)

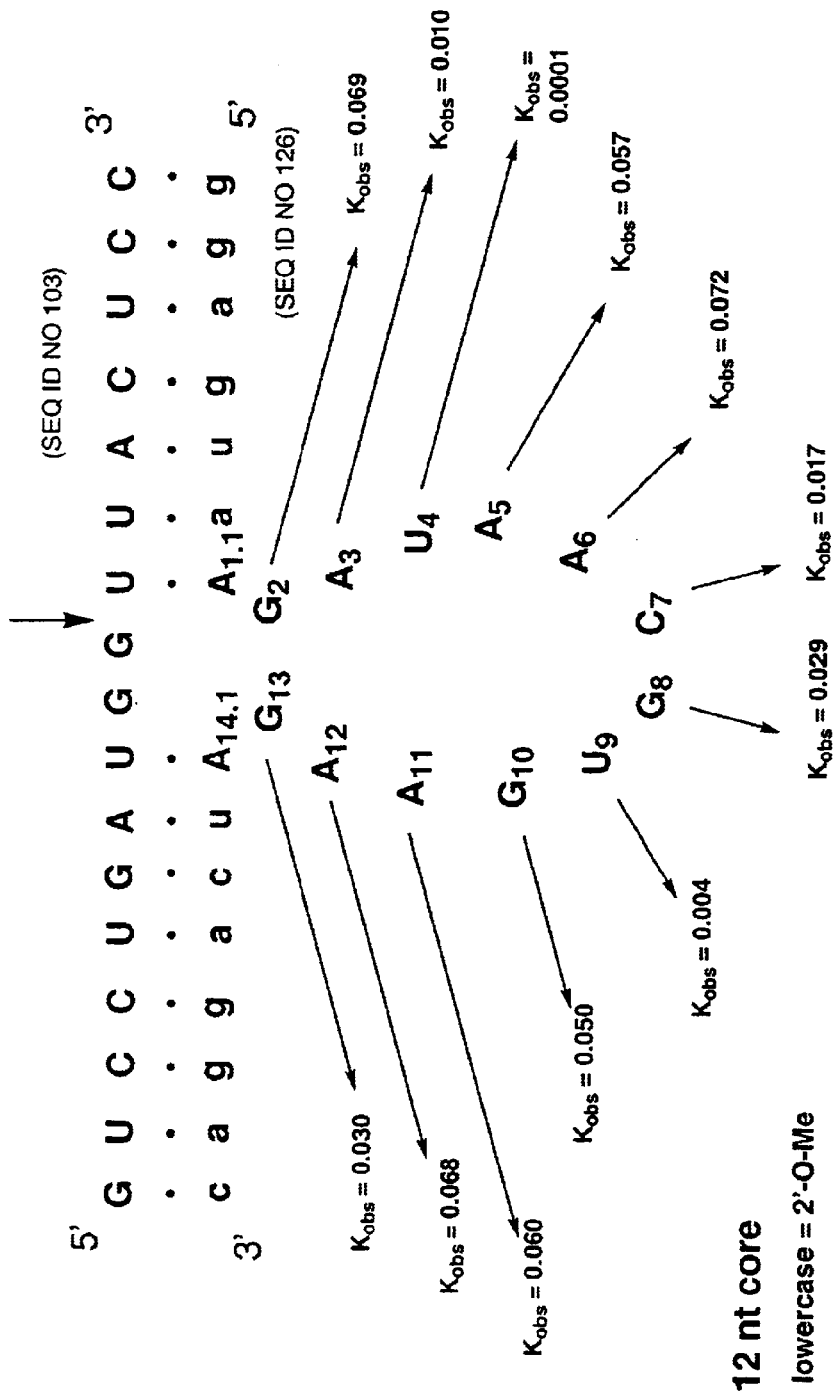

Figure 7: Class I and VIII Sequence and Structural Similarities
(SEQ ID NO 103)
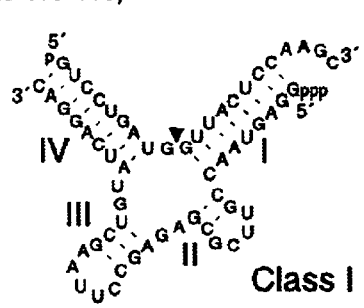
Class I
(SEQ ID NO 117)
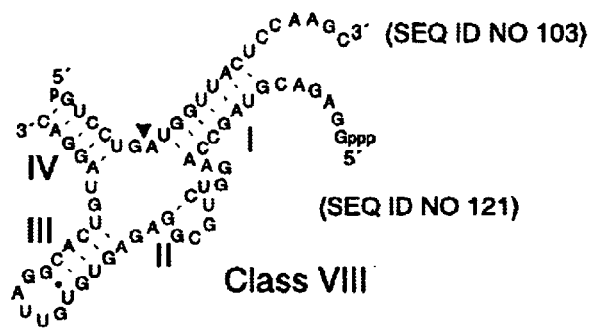
(SEQ ID NO 103)
(SEQ ID NO 121)
Class VIII
Class I motif cleavage site
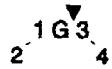
1 = A or U
2 = complementary to 1
3 = G, A or U
4 = complementary to 3

SEQUENCE LISTING

<160> NUMBER OF SEQ ID NOS: 126

<210> SEQ ID NO 1
<211> LENGTH: 28
<212> TYPE: RNA
<213> ORGANISM: Artificial Sequence
<220> FEATURE:
<223> OTHER INFORMATION: Description of Artificial Sequence: Enzymatic
      Nucleic Acid
<221> NAME/KEY: misc_feature
<222> LOCATION: (1)..(6)
<223> OTHER INFORMATION: 2'-O-Methyl
<221> NAME/KEY: misc_feature
<222> LOCATION: (21)..(27)
<223> OTHER INFORMATION: 2'-O-Methyl
<221> NAME/KEY: misc_feature
<222> LOCATION: (28)..(28)
<223> OTHER INFORMATION: n stands for inverted deoxyabasic derivative

<400> SEQUENCE: 1
ggaguaagau aacgugaaga ucaggacn                                    28

```
<210> SEQ ID NO 2
<211> LENGTH: 28
<212> TYPE: RNA
<213> ORGANISM: Artificial Sequence
<220> FEATURE:
<223> OTHER INFORMATION: Description of Artificial Sequence:  Enzymatic
      Nucleic Acid
<221> NAME/KEY: misc_feature
<222> LOCATION: (1)..(5)
<223> OTHER INFORMATION: 2'-O-Methyl
<221> NAME/KEY: misc_feature
<222> LOCATION: (21)..(27)
<223> OTHER INFORMATION: 2'-O-Methyl
<221> NAME/KEY: misc_feature
<222> LOCATION: (28)..(28)
<223> OTHER INFORMATION: n stands for inverted deoxyabasic derivative

<400> SEQUENCE: 2
ggaguaagau aacgugaaga ucaggacn                                             28

<210> SEQ ID NO 3
<211> LENGTH: 27
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 3
ggaguaagau aacgugaaga ucaggac                                              27

<210> SEQ ID NO 4
<211> LENGTH: 28
<212> TYPE: RNA
<213> ORGANISM: Artificial Sequence
<220> FEATURE:
<223> OTHER INFORMATION: Description of Artificial Sequence:  Enzymatic
      Nucleic Acid
<221> NAME/KEY: misc_feature
<222> LOCATION: (1)..(5)
<223> OTHER INFORMATION: 2'-O-Methyl
<221> NAME/KEY: misc_feature
<222> LOCATION: (22)..(27)
<223> OTHER INFORMATION: 2'-O-Methyl
<221> NAME/KEY: misc_feature
<222> LOCATION: (28)..(28)
<223> OTHER INFORMATION: n stands for inverted deoxyabasic derivative

<400> SEQUENCE: 4
ggaguaagau aacgugaaga ucaggacn                                             28

<210> SEQ ID NO 5
<211> LENGTH: 28
<212> TYPE: RNA
<213> ORGANISM: Artificial Sequence
<220> FEATURE:
<223> OTHER INFORMATION: Description of Artificial Sequence:  Enzymatic
      Nucleic Acid
<221> NAME/KEY: misc_feature
<222> LOCATION: (1)..(5)
<223> OTHER INFORMATION: 2'-O-Methyl
<221> NAME/KEY: misc_feature
<222> LOCATION: (23)..(27)
<223> OTHER INFORMATION: 2'-O-Methyl
<221> NAME/KEY: misc_feature
<222> LOCATION: (28)..(28)
<223> OTHER INFORMATION: n stands for inverted deoxyabasic derivative

<400> SEQUENCE: 5
ggaguaagau aacgugaaga ucaggacn                                             28
```

```
<210> SEQ ID NO 6
<211> LENGTH: 28
<212> TYPE: RNA
<213> ORGANISM: Artificial Sequence
<220> FEATURE:
<223> OTHER INFORMATION: Description of Artificial Sequence: Enzymatic
      Nucleic Acid
<221> NAME/KEY: misc_feature
<222> LOCATION: (1)..(4)
<223> OTHER INFORMATION: 2'-O-Methyl
<221> NAME/KEY: misc_feature
<222> LOCATION: (24)..(27)
<223> OTHER INFORMATION: 2'-O-Methyl
<221> NAME/KEY: misc_feature
<222> LOCATION: (28)..(28)
<223> OTHER INFORMATION: n stands for inverted deoxyabasic derivative

<400> SEQUENCE: 6
ggaguaagau aacgugaaga ucaggacn                                    28

<210> SEQ ID NO 7
<211> LENGTH: 28
<212> TYPE: RNA
<213> ORGANISM: Artificial Sequence
<220> FEATURE:
<223> OTHER INFORMATION: Description of Artificial Sequence: Enzymatic
      Nucleic Acid
<221> NAME/KEY: misc_feature
<222> LOCATION: (1)..(4)
<223> OTHER INFORMATION: 2'-O-Methyl
<221> NAME/KEY: misc_feature
<222> LOCATION: (23)..(27)
<223> OTHER INFORMATION: 2'-O-Methyl
<221> NAME/KEY: misc_feature
<222> LOCATION: (28)..(28)
<223> OTHER INFORMATION: n stands for inverted deoxyabasic derivative

<400> SEQUENCE: 7
ggaguaagau aacgugaaga ucaggacn                                    28

<210> SEQ ID NO 8
<211> LENGTH: 28
<212> TYPE: RNA
<213> ORGANISM: Artificial Sequence
<220> FEATURE:
<223> OTHER INFORMATION: Description of Artificial Sequence: Enzymatic
      Nucleic Acid
<221> NAME/KEY: misc_feature
<222> LOCATION: (1)..(6)
<223> OTHER INFORMATION: 2'-O-Methyl
<221> NAME/KEY: misc_feature
<222> LOCATION: (20)..(27)
<223> OTHER INFORMATION: 2'-O-Methyl
<221> NAME/KEY: misc_feature
<222> LOCATION: (28)..(28)
<223> OTHER INFORMATION: n stands for inverted deoxyabasic derivative

<400> SEQUENCE: 8
ggaguaagau aacgugaaga ucaggacn                                    28

<210> SEQ ID NO 9
<211> LENGTH: 28
<212> TYPE: RNA
<213> ORGANISM: Artificial Sequence
<220> FEATURE:
<223> OTHER INFORMATION: Description of Artificial Sequence: Enzymatic
      Nucleic Acid
<221> NAME/KEY: misc_feature
<222> LOCATION: (1)..(6)
<223> OTHER INFORMATION: 2'-O-Methyl
<221> NAME/KEY: misc_feature
<222> LOCATION: (12)..(12)
```

-continued

```
<223> OTHER INFORMATION: 2'-O-Methyl
<221> NAME/KEY: misc_feature
<222> LOCATION: (21)..(27)
<223> OTHER INFORMATION: 2'-O-Methyl
<221> NAME/KEY: misc_feature
<222> LOCATION: (28)..(28)
<223> OTHER INFORMATION: n stands for inverted deoxyabasic derivative

<400> SEQUENCE: 9
ggaguaagau aacgugaaga ucaggacn                                              28

<210> SEQ ID NO 10
<211> LENGTH: 28
<212> TYPE: RNA
<213> ORGANISM: Artificial Sequence
<220> FEATURE:
<223> OTHER INFORMATION: Description of Artificial Sequence:  Enzymatic
      Nucleic Acid
<221> NAME/KEY: misc_feature
<222> LOCATION: (1)..(7)
<223> OTHER INFORMATION: 2'-O-Methyl
<221> NAME/KEY: misc_feature
<222> LOCATION: (21)..(27)
<223> OTHER INFORMATION: 2'-O-Methyl
<221> NAME/KEY: misc_feature
<222> LOCATION: (28)..(28)
<223> OTHER INFORMATION: n stands for inverted deoxyabasic derivative

<400> SEQUENCE: 10
ggaguaagau aacgugaaga ucaggacn                                              28

<210> SEQ ID NO 11
<211> LENGTH: 28
<212> TYPE: RNA
<213> ORGANISM: Artificial Sequence
<220> FEATURE:
<223> OTHER INFORMATION: Description of Artificial Sequence:  Enzymatic
      Nucleic Acid
<221> NAME/KEY: misc_feature
<222> LOCATION: (1)..(6)
<223> OTHER INFORMATION: 2'-O-Methyl
<221> NAME/KEY: misc_feature
<222> LOCATION: (21)..(27)
<223> OTHER INFORMATION: 2'-O-Methyl
<221> NAME/KEY: misc_feature
<222> LOCATION: (28)..(28)
<223> OTHER INFORMATION: n stands for inverted deoxyabasic derivative

<400> SEQUENCE: 11
ggaguaagau aacgugaaga ucaggacn                                              28

<210> SEQ ID NO 12
<211> LENGTH: 28
<212> TYPE: RNA
<213> ORGANISM: Artificial Sequence
<220> FEATURE:
<223> OTHER INFORMATION: Description of Artificial Sequence:  Enzymatic
      Nucleic Acid
<221> NAME/KEY: misc_feature
<222> LOCATION: (1)..(6)
<223> OTHER INFORMATION: 2'-O-Methyl
<221> NAME/KEY: misc_feature
<222> LOCATION: (18)..(18)
<223> OTHER INFORMATION: 2'-O-Methyl
<221> NAME/KEY: misc_feature
<222> LOCATION: (21)..(27)
<223> OTHER INFORMATION: 2'-O-Methyl
<221> NAME/KEY: misc_feature
<222> LOCATION: (28)..(28)
<223> OTHER INFORMATION: n stands for inverted deoxyabasic derivative

<400> SEQUENCE: 12
```

```
ggaguaagau aacgugaaga ucaggacn                              28
```

<210> SEQ ID NO 13
<211> LENGTH: 28
<212> TYPE: RNA
<213> ORGANISM: Artificial Sequence
<220> FEATURE:
<223> OTHER INFORMATION: Description of Artificial Sequence:  Enzymatic
      Nucleic Acid
<221> NAME/KEY: misc_feature
<222> LOCATION: (1)..(6)
<223> OTHER INFORMATION: 2'-O-Methyl
<221> NAME/KEY: misc_feature
<222> LOCATION: (17)..(17)
<223> OTHER INFORMATION: 2'-O-Methyl
<221> NAME/KEY: misc_feature
<222> LOCATION: (21)..(27)
<223> OTHER INFORMATION: 2'-O-Methyl
<221> NAME/KEY: misc_feature
<222> LOCATION: (28)..(28)
<223> OTHER INFORMATION: n stands for inverted deoxyabasic derivative

<400> SEQUENCE: 13

```
ggaguaagau aacgugaaga ucaggacn                              28
```

<210> SEQ ID NO 14
<211> LENGTH: 28
<212> TYPE: RNA
<213> ORGANISM: Artificial Sequence
<220> FEATURE:
<223> OTHER INFORMATION: Description of Artificial Sequence:  Enzymatic
      Nucleic Acid
<221> NAME/KEY: misc_feature
<222> LOCATION: (1)..(6)
<223> OTHER INFORMATION: 2'-O-Methyl
<221> NAME/KEY: misc_feature
<222> LOCATION: (11)..(11)
<223> OTHER INFORMATION: 2'-O-Methyl
<221> NAME/KEY: misc_feature
<222> LOCATION: (16)..(16)
<223> OTHER INFORMATION: 2'-O-Methyl
<221> NAME/KEY: misc_feature
<222> LOCATION: (21)..(27)
<223> OTHER INFORMATION: 2'-O-Methyl
<221> NAME/KEY: misc_feature
<222> LOCATION: (28)..(28)
<223> OTHER INFORMATION: n stands for inverted deoxyabasic derivative

<400> SEQUENCE: 14

```
ggaguaagau aacgugaaga ucaggacn                              28
```

<210> SEQ ID NO 15
<211> LENGTH: 28
<212> TYPE: RNA
<213> ORGANISM: Artificial Sequence
<220> FEATURE:
<223> OTHER INFORMATION: Description of Artificial Sequence:  Enzymatic
      Nucleic Acid
<221> NAME/KEY: misc_feature
<222> LOCATION: (1)..(6)
<223> OTHER INFORMATION: 2'-O-Methyl
<221> NAME/KEY: misc_feature
<222> LOCATION: (21)..(27)
<223> OTHER INFORMATION: 2'-O-Methyl
<221> NAME/KEY: misc_feature
<222> LOCATION: (28)..(28)
<223> OTHER INFORMATION: n stands for inverted deoxyabasic derivative

<400> SEQUENCE: 15

```
ggaguaagau aacgugaaga ucaggacn                              28
```

<210> SEQ ID NO 16

```
<211> LENGTH: 28
<212> TYPE: RNA
<213> ORGANISM: Artificial Sequence
<220> FEATURE:
<223> OTHER INFORMATION: Description of Artificial Sequence: Enzymatic
      Nucleic Acid
<221> NAME/KEY: misc_feature
<222> LOCATION: (1)..(6)
<223> OTHER INFORMATION: 2'-O-Methyl
<221> NAME/KEY: misc_feature
<222> LOCATION: (19)..(19)
<223> OTHER INFORMATION: 2'-O-Methyl
<221> NAME/KEY: misc_feature
<222> LOCATION: (21)..(27)
<223> OTHER INFORMATION: 2'-O-Methyl
<221> NAME/KEY: misc_feature
<222> LOCATION: (28)..(28)
<223> OTHER INFORMATION: n stands for inverted deoxyabasic derivative

<400> SEQUENCE: 16
ggaguaagau aacgugaaga ucaggacn                                      28

<210> SEQ ID NO 17
<211> LENGTH: 28
<212> TYPE: RNA
<213> ORGANISM: Artificial Sequence
<220> FEATURE:
<223> OTHER INFORMATION: Description of Artificial Sequence: Enzymatic
      Nucleic Acid
<221> NAME/KEY: misc_feature
<222> LOCATION: (1)..(6)
<223> OTHER INFORMATION: 2'-O-Methyl
<221> NAME/KEY: misc_feature
<222> LOCATION: (14)..(14)
<223> OTHER INFORMATION: 2'-O-Methyl
<221> NAME/KEY: misc_feature
<222> LOCATION: (21)..(27)
<223> OTHER INFORMATION: 2'-O-Methyl
<221> NAME/KEY: misc_feature
<222> LOCATION: (28)..(28)
<223> OTHER INFORMATION: n stands for inverted deoxyabasic derivative

<400> SEQUENCE: 17
ggaguaagau aacgugaaga ucaggacn                                      28

<210> SEQ ID NO 18
<211> LENGTH: 28
<212> TYPE: RNA
<213> ORGANISM: Artificial Sequence
<220> FEATURE:
<223> OTHER INFORMATION: Description of Artificial Sequence: Enzymatic
      Nucleic Acid
<221> NAME/KEY: misc_feature
<222> LOCATION: (1)..(6)
<223> OTHER INFORMATION: 2'-O-Methyl
<221> NAME/KEY: misc_feature
<222> LOCATION: (13)..(13)
<223> OTHER INFORMATION: 2'-O-Methyl
<221> NAME/KEY: misc_feature
<222> LOCATION: (21)..(27)
<223> OTHER INFORMATION: 2'-O-Methyl
<221> NAME/KEY: misc_feature
<222> LOCATION: (28)..(28)
<223> OTHER INFORMATION: n stands for inverted deoxyabasic derivative

<400> SEQUENCE: 18
ggaguaagau aacgugaaga ucaggacn                                      28

<210> SEQ ID NO 19
<211> LENGTH: 28
<212> TYPE: RNA
<213> ORGANISM: Artificial Sequence
<220> FEATURE:
```

```
<223> OTHER INFORMATION: Description of Artificial Sequence:  Enzymatic
      Nucleic Acid
<221> NAME/KEY: misc_feature
<222> LOCATION: (1)..(6)
<223> OTHER INFORMATION: 2'-O-Methyl
<221> NAME/KEY: misc_feature
<222> LOCATION: (21)..(27)
<223> OTHER INFORMATION: 2'-O-Methyl
<221> NAME/KEY: misc_feature
<222> LOCATION: (28)..(28)
<223> OTHER INFORMATION: n stands for inverted deoxyabasic derivative

<400> SEQUENCE: 19
ggaguaagau aacgugaaga ucaggacn                                              28

<210> SEQ ID NO 20
<211> LENGTH: 28
<212> TYPE: RNA
<213> ORGANISM: Artificial Sequence
<220> FEATURE:
<223> OTHER INFORMATION: Description of Artificial Sequence:  Enzymatic
      Nucleic Acid
<221> NAME/KEY: misc_feature
<222> LOCATION: (1)..(6)
<223> OTHER INFORMATION: 2'-O-Methyl
<221> NAME/KEY: misc_feature
<222> LOCATION: (15)..(15)
<223> OTHER INFORMATION: 2'-O-Methyl
<221> NAME/KEY: misc_feature
<222> LOCATION: (21)..(27)
<223> OTHER INFORMATION: 2'-O-Methyl
<221> NAME/KEY: misc_feature
<222> LOCATION: (28)..(28)
<223> OTHER INFORMATION: n stands for inverted deoxyabasic derivative

<400> SEQUENCE: 20
ggaguaagau aacgugaaga ucaggacn                                              28

<210> SEQ ID NO 21
<211> LENGTH: 28
<212> TYPE: RNA
<213> ORGANISM: Artificial Sequence
<220> FEATURE:
<223> OTHER INFORMATION: Description of Artificial Sequence:  Enzymatic
      Nucleic Acid
<221> NAME/KEY: misc_feature
<222> LOCATION: (1)..(6)
<223> OTHER INFORMATION: 2'-O-Methyl
<221> NAME/KEY: misc_feature
<222> LOCATION: (10)..(10)
<223> OTHER INFORMATION: 2'-O-Methyl
<221> NAME/KEY: misc_feature
<222> LOCATION: (21)..(27)
<223> OTHER INFORMATION: 2'-O-Methyl
<221> NAME/KEY: misc_feature
<222> LOCATION: (28)..(28)
<223> OTHER INFORMATION: n stands for inverted deoxyabasic derivative

<400> SEQUENCE: 21
ggaguaagau aacgugaaga ucaggacn                                              28

<210> SEQ ID NO 22
<211> LENGTH: 28
<212> TYPE: RNA
<213> ORGANISM: Artificial Sequence
<220> FEATURE:
<223> OTHER INFORMATION: Description of Artificial Sequence:  Enzymatic
      Nucleic Acid
<221> NAME/KEY: misc_feature
<222> LOCATION: (1)..(19)
<223> OTHER INFORMATION: 2'-O-Methyl
<221> NAME/KEY: misc_feature
<222> LOCATION: (21)..(27)
```

```
<223> OTHER INFORMATION: 2'-O-Methyl
<221> NAME/KEY: misc_feature
<222> LOCATION: (28)..(28)
<223> OTHER INFORMATION: n stands for inverted deoxyabasic derivative

<400> SEQUENCE: 22
ggaguaagau aacgugaaga ucaggacn                                          28

<210> SEQ ID NO 23
<211> LENGTH: 28
<212> TYPE: RNA
<213> ORGANISM: Artificial Sequence
<220> FEATURE:
<223> OTHER INFORMATION: Description of Artificial Sequence:  Enzymatic
      Nucleic Acid
<221> NAME/KEY: misc_feature
<222> LOCATION: (1)..(8)
<223> OTHER INFORMATION: 2'-O-Methyl
<221> NAME/KEY: misc_feature
<222> LOCATION: (11)..(12)
<223> OTHER INFORMATION: 2'-O-Methyl
<221> NAME/KEY: misc_feature
<222> LOCATION: (16)..(18)
<223> OTHER INFORMATION: 2'-O-Methyl
<221> NAME/KEY: misc_feature
<222> LOCATION: (21)..(27)
<223> OTHER INFORMATION: 2'-O-Methyl
<221> NAME/KEY: misc_feature
<222> LOCATION: (28)..(28)
<223> OTHER INFORMATION: n stands for inverted deoxyabasic derivative

<400> SEQUENCE: 23
ggaguaagau aacgugaaga ucaggacn                                          28

<210> SEQ ID NO 24
<211> LENGTH: 28
<212> TYPE: RNA
<213> ORGANISM: Artificial Sequence
<220> FEATURE:
<223> OTHER INFORMATION: Description of Artificial Sequence:  Enzymatic
      Nucleic Acid
<221> NAME/KEY: misc_feature
<222> LOCATION: (1)..(9)
<223> OTHER INFORMATION: 2'-O-Methyl
<221> NAME/KEY: misc_feature
<222> LOCATION: (11)..(12)
<223> OTHER INFORMATION: 2'-O-Methyl
<221> NAME/KEY: misc_feature
<222> LOCATION: (16)..(18)
<223> OTHER INFORMATION: 2'-O-Methyl
<221> NAME/KEY: misc_feature
<222> LOCATION: (21)..(27)
<223> OTHER INFORMATION: 2'-O-Methyl
<221> NAME/KEY: misc_feature
<222> LOCATION: (28)..(28)
<223> OTHER INFORMATION: n stands for inverted deoxyabasic derivative

<400> SEQUENCE: 24
ggaguaagau aacgugaaga ucaggacn                                          28

<210> SEQ ID NO 25
<211> LENGTH: 28
<212> TYPE: RNA
<213> ORGANISM: Artificial Sequence
<220> FEATURE:
<223> OTHER INFORMATION: Description of Artificial Sequence:  Enzymatic
      Nucleic Acid
<221> NAME/KEY: misc_feature
<222> LOCATION: (1)..(9)
<223> OTHER INFORMATION: 2'-O-Methyl
<221> NAME/KEY: misc_feature
<222> LOCATION: (11)..(12)
<223> OTHER INFORMATION: 2'-O-Methyl
```

```
<221> NAME/KEY: misc_feature
<222> LOCATION: (14)..(14)
<223> OTHER INFORMATION: 2'-O-Methyl
<221> NAME/KEY: misc_feature
<222> LOCATION: (16)..(19)
<223> OTHER INFORMATION: 2'-O-Methyl
<221> NAME/KEY: misc_feature
<222> LOCATION: (21)..(27)
<223> OTHER INFORMATION: 2'-O-Methyl
<221> NAME/KEY: misc_feature
<222> LOCATION: (28)..(28)
<223> OTHER INFORMATION: n stands for inverted deoxyabasic derivative

<400> SEQUENCE: 25
ggaguaagau aacgugaaga ucaggacn                                        28

<210> SEQ ID NO 26
<211> LENGTH: 28
<212> TYPE: RNA
<213> ORGANISM: Artificial Sequence
<220> FEATURE:
<223> OTHER INFORMATION: Description of Artificial Sequence: Enzymatic
      Nucleic Acid
<221> NAME/KEY: misc_feature
<222> LOCATION: (1)..(9)
<223> OTHER INFORMATION: 2'-O-Methyl
<221> NAME/KEY: misc_feature
<222> LOCATION: (11)..(12)
<223> OTHER INFORMATION: 2'-O-Methyl
<221> NAME/KEY: misc_feature
<222> LOCATION: (16)..(19)
<223> OTHER INFORMATION: 2'-O-Methyl
<221> NAME/KEY: misc_feature
<222> LOCATION: (21)..(27)
<223> OTHER INFORMATION: 2'-O-Methyl
<221> NAME/KEY: misc_feature
<222> LOCATION: (28)..(28)
<223> OTHER INFORMATION: n stands for inverted deoxyabasic derivative

<400> SEQUENCE: 26
ggaguaagau aacgugaaga ucaggacn                                        28

<210> SEQ ID NO 27
<211> LENGTH: 28
<212> TYPE: RNA
<213> ORGANISM: Artificial Sequence
<220> FEATURE:
<223> OTHER INFORMATION: Description of Artificial Sequence: Enzymatic
      Nucleic Acid
<221> NAME/KEY: misc_feature
<222> LOCATION: (1)..(9)
<223> OTHER INFORMATION: 2'-O-Methyl
<221> NAME/KEY: misc_feature
<222> LOCATION: (11)..(14)
<223> OTHER INFORMATION: 2'-O-Methyl
<221> NAME/KEY: misc_feature
<222> LOCATION: (16)..(19)
<223> OTHER INFORMATION: 2'-O-Methyl
<221> NAME/KEY: misc_feature
<222> LOCATION: (21)..(27)
<223> OTHER INFORMATION: 2'-O-Methyl
<221> NAME/KEY: misc_feature
<222> LOCATION: (28)..(28)
<223> OTHER INFORMATION: n stands for inverted deoxyabasic derivative

<400> SEQUENCE: 27
ggaguaagau aacgugaaga ucaggacn                                        28

<210> SEQ ID NO 28
<211> LENGTH: 28
<212> TYPE: RNA
<213> ORGANISM: Artificial Sequence
<220> FEATURE:
```

<223> OTHER INFORMATION: Description of Artificial Sequence: Enzymatic
      Nucleic Acid
<221> NAME/KEY: misc_feature
<222> LOCATION: (1)..(8)
<223> OTHER INFORMATION: 2'-O-Methyl
<221> NAME/KEY: misc_feature
<222> LOCATION: (11)..(12)
<223> OTHER INFORMATION: 2'-O-Methyl
<221> NAME/KEY: misc_feature
<222> LOCATION: (16)..(18)
<223> OTHER INFORMATION: 2'-O-Methyl
<221> NAME/KEY: misc_feature
<222> LOCATION: (21)..(27)
<223> OTHER INFORMATION: 2'-O-Methyl
<221> NAME/KEY: misc_feature
<222> LOCATION: (10)..(10)
<223> OTHER INFORMATION: Phosphorodithioate 3'-Internucleotide Linkage
<221> NAME/KEY: misc_feature
<222> LOCATION: (28)..(28)
<223> OTHER INFORMATION: n stands for inverted deoxyabasic derivative

<400> SEQUENCE: 28
ggaguaagau aacgugaaga ucaggacn                                    28

<210> SEQ ID NO 29
<211> LENGTH: 28
<212> TYPE: RNA
<213> ORGANISM: Artificial Sequence
<220> FEATURE:
<223> OTHER INFORMATION: Description of Artificial Sequence: Enzymatic
      Nucleic Acid
<221> NAME/KEY: misc_feature
<222> LOCATION: (1)..(8)
<223> OTHER INFORMATION: 2'-O-Methyl
<221> NAME/KEY: misc_feature
<222> LOCATION: (11)..(12)
<223> OTHER INFORMATION: 2'-O-Methyl
<221> NAME/KEY: misc_feature
<222> LOCATION: (16)..(18)
<223> OTHER INFORMATION: 2'-O-Methyl
<221> NAME/KEY: misc_feature
<222> LOCATION: (21)..(27)
<223> OTHER INFORMATION: 2'-O-Methyl
<221> NAME/KEY: misc_feature
<222> LOCATION: (13)..(13)
<223> OTHER INFORMATION: 2'-deoxy-2'-fluoro
<221> NAME/KEY: misc_feature
<222> LOCATION: (28)..(28)
<223> OTHER INFORMATION: n stands for inverted deoxyabasic derivative

<400> SEQUENCE: 29
ggaguaagau aacgugaaga ucaggacn                                    28

<210> SEQ ID NO 30
<211> LENGTH: 28
<212> TYPE: RNA
<213> ORGANISM: Artificial Sequence
<220> FEATURE:
<223> OTHER INFORMATION: Description of Artificial Sequence: Enzymatic
      Nucleic Acid
<221> NAME/KEY: misc_feature
<222> LOCATION: (1)..(8)
<223> OTHER INFORMATION: 2'-O-Methyl
<221> NAME/KEY: misc_feature
<222> LOCATION: (11)..(12)
<223> OTHER INFORMATION: 2'-O-Methyl
<221> NAME/KEY: misc_feature
<222> LOCATION: (16)..(18)
<223> OTHER INFORMATION: 2'-O-Methyl
<221> NAME/KEY: misc_feature
<222> LOCATION: (21)..(27)
<223> OTHER INFORMATION: 2'-O-Methyl
<221> NAME/KEY: misc_feature
<222> LOCATION: (13)..(13)
<223> OTHER INFORMATION: 2'-deoxy-2'-amino

```
<221> NAME/KEY: misc_feature
<222> LOCATION: (28)..(28)
<223> OTHER INFORMATION: n stands for inverted deoxyabasic derivative

<400> SEQUENCE: 30
ggaguaagau aacgugaaga ucaggacn                                         28

<210> SEQ ID NO 31
<211> LENGTH: 28
<212> TYPE: RNA
<213> ORGANISM: Artificial Sequence
<220> FEATURE:
<223> OTHER INFORMATION: Description of Artificial Sequence:  Enzymatic
      Nucleic Acid
<221> NAME/KEY: misc_feature
<222> LOCATION: (1)..(8)
<223> OTHER INFORMATION: 2'-O-Methyl
<221> NAME/KEY: misc_feature
<222> LOCATION: (11)..(12)
<223> OTHER INFORMATION: 2'-O-Methyl
<221> NAME/KEY: misc_feature
<222> LOCATION: (16)..(18)
<223> OTHER INFORMATION: 2'-O-Methyl
<221> NAME/KEY: misc_feature
<222> LOCATION: (21)..(27)
<223> OTHER INFORMATION: 2'-O-Methyl
<221> NAME/KEY: misc_feature
<222> LOCATION: (15)..(15)
<223> OTHER INFORMATION: Phosphorodithioate 3'-Internucleotide Linkage
<221> NAME/KEY: misc_feature
<222> LOCATION: (28)..(28)
<223> OTHER INFORMATION: n stands for inverted deoxyabasic derivative

<400> SEQUENCE: 31
ggaguaagau aacgugaaga ucaggacn                                         28

<210> SEQ ID NO 32
<211> LENGTH: 28
<212> TYPE: RNA
<213> ORGANISM: Artificial Sequence
<220> FEATURE:
<223> OTHER INFORMATION: Description of Artificial Sequence:  Enzymatic
      Nucleic Acid
<221> NAME/KEY: misc_feature
<222> LOCATION: (1)..(8)
<223> OTHER INFORMATION: 2'-O-Methyl
<221> NAME/KEY: misc_feature
<222> LOCATION: (11)..(12)
<223> OTHER INFORMATION: 2'-O-Methyl
<221> NAME/KEY: misc_feature
<222> LOCATION: (16)..(18)
<223> OTHER INFORMATION: 2'-O-Methyl
<221> NAME/KEY: misc_feature
<222> LOCATION: (21)..(27)
<223> OTHER INFORMATION: 2'-O-Methyl
<221> NAME/KEY: misc_feature
<222> LOCATION: (13)..(13)
<223> OTHER INFORMATION: 2'-deoxy
<221> NAME/KEY: misc_feature
<222> LOCATION: (28)..(28)
<223> OTHER INFORMATION: n stands for inverted deoxyabasic derivative

<400> SEQUENCE: 32
ggaguaagau aacgugaaga ucaggacn                                         28

<210> SEQ ID NO 33
<211> LENGTH: 28
<212> TYPE: RNA
<213> ORGANISM: Artificial Sequence
<220> FEATURE:
<223> OTHER INFORMATION: Description of Artificial Sequence:  Enzymatic
      Nucleic Acid
<221> NAME/KEY: misc_feature
```

```
<222> LOCATION: (1)..(8)
<223> OTHER INFORMATION: 2'-O-Methyl
<221> NAME/KEY: misc_feature
<222> LOCATION: (11)..(12)
<223> OTHER INFORMATION: 2'-O-Methyl
<221> NAME/KEY: misc_feature
<222> LOCATION: (16)..(18)
<223> OTHER INFORMATION: 2'-O-Methyl
<221> NAME/KEY: misc_feature
<222> LOCATION: (21)..(27)
<223> OTHER INFORMATION: 2'-O-Methyl
<221> NAME/KEY: misc_feature
<222> LOCATION: (15)..(15)
<223> OTHER INFORMATION: 2'-deoxy-2'-amino
<221> NAME/KEY: misc_feature
<222> LOCATION: (28)..(28)
<223> OTHER INFORMATION: n stands for inverted deoxyabasic derivative

<400> SEQUENCE: 33
ggaguaagau aacgugaaga ucaggacn                                28

<210> SEQ ID NO 34
<211> LENGTH: 28
<212> TYPE: RNA
<213> ORGANISM: Artificial Sequence
<220> FEATURE:
<223> OTHER INFORMATION: Description of Artificial Sequence:  Enzymatic
      Nucleic Acid
<221> NAME/KEY: misc_feature
<222> LOCATION: (1)..(8)
<223> OTHER INFORMATION: 2'-O-Methyl
<221> NAME/KEY: misc_feature
<222> LOCATION: (11)..(12)
<223> OTHER INFORMATION: 2'-O-Methyl
<221> NAME/KEY: misc_feature
<222> LOCATION: (16)..(18)
<223> OTHER INFORMATION: 2'-O-Methyl
<221> NAME/KEY: misc_feature
<222> LOCATION: (21)..(27)
<223> OTHER INFORMATION: 2'-O-Methyl
<221> NAME/KEY: misc_feature
<222> LOCATION: (15)..(15)
<223> OTHER INFORMATION: 2'-deoxy-2'-fluoro
<221> NAME/KEY: misc_feature
<222> LOCATION: (28)..(28)
<223> OTHER INFORMATION: n stands for inverted deoxyabasic derivative

<400> SEQUENCE: 34
ggaguaagau aacgugaaga ucaggacn                                28

<210> SEQ ID NO 35
<211> LENGTH: 28
<212> TYPE: RNA
<213> ORGANISM: Artificial Sequence
<220> FEATURE:
<223> OTHER INFORMATION: Description of Artificial Sequence:  Enzymatic
      Nucleic Acid
<221> NAME/KEY: misc_feature
<222> LOCATION: (1)..(8)
<223> OTHER INFORMATION: 2'-O-Methyl
<221> NAME/KEY: misc_feature
<222> LOCATION: (11)..(12)
<223> OTHER INFORMATION: 2'-O-Methyl
<221> NAME/KEY: misc_feature
<222> LOCATION: (16)..(18)
<223> OTHER INFORMATION: 2'-O-Methyl
<221> NAME/KEY: misc_feature
<222> LOCATION: (21)..(27)
<223> OTHER INFORMATION: 2'-O-Methyl
<221> NAME/KEY: misc_feature
<222> LOCATION: (15)..(15)
<223> OTHER INFORMATION: 2'-deoxy
<221> NAME/KEY: misc_feature
<222> LOCATION: (28)..(28)
<223> OTHER INFORMATION: n stands for inverted deoxyabasic derivative
```

```
<400> SEQUENCE: 35
ggaguaagau aacgugaaga ucaggacn                                             28

<210> SEQ ID NO 36
<211> LENGTH: 28
<212> TYPE: RNA
<213> ORGANISM: Artificial Sequence
<220> FEATURE:
<223> OTHER INFORMATION: Description of Artificial Sequence:  Enzymatic
      Nucleic Acid
<221> NAME/KEY: misc_feature
<222> LOCATION: (1)..(8)
<223> OTHER INFORMATION: 2'-O-Methyl
<221> NAME/KEY: misc_feature
<222> LOCATION: (11)..(12)
<223> OTHER INFORMATION: 2'-O-Methyl
<221> NAME/KEY: misc_feature
<222> LOCATION: (16)..(18)
<223> OTHER INFORMATION: 2'-O-Methyl
<221> NAME/KEY: misc_feature
<222> LOCATION: (21)..(27)
<223> OTHER INFORMATION: 2'-O-Methyl
<221> NAME/KEY: misc_feature
<222> LOCATION: (10)..(10)
<223> OTHER INFORMATION: 2'-deoxy-2'-amino
<221> NAME/KEY: misc_feature
<222> LOCATION: (28)..(28)
<223> OTHER INFORMATION: n stands for inverted deoxyabasic derivative

<400> SEQUENCE: 36
ggaguaagau aacgugaaga ucaggacn                                             28

<210> SEQ ID NO 37
<211> LENGTH: 28
<212> TYPE: RNA
<213> ORGANISM: Artificial Sequence
<220> FEATURE:
<223> OTHER INFORMATION: Description of Artificial Sequence:  Enzymatic
      Nucleic Acid
<221> NAME/KEY: misc_feature
<222> LOCATION: (1)..(8)
<223> OTHER INFORMATION: 2'-O-Methyl
<221> NAME/KEY: misc_feature
<222> LOCATION: (11)..(12)
<223> OTHER INFORMATION: 2'-O-Methyl
<221> NAME/KEY: misc_feature
<222> LOCATION: (16)..(18)
<223> OTHER INFORMATION: 2'-O-Methyl
<221> NAME/KEY: misc_feature
<222> LOCATION: (21)..(27)
<223> OTHER INFORMATION: 2'-O-Methyl
<221> NAME/KEY: misc_feature
<222> LOCATION: (10)..(10)
<223> OTHER INFORMATION: 2'-deoxy-2'-fluoro
<221> NAME/KEY: misc_feature
<222> LOCATION: (28)..(28)
<223> OTHER INFORMATION: n stands for inverted deoxyabasic derivative

<400> SEQUENCE: 37
ggaguaagau aacgugaaga ucaggacn                                             28

<210> SEQ ID NO 38
<211> LENGTH: 28
<212> TYPE: RNA
<213> ORGANISM: Artificial Sequence
<220> FEATURE:
<223> OTHER INFORMATION: Description of Artificial Sequence:  Enzymatic
      Nucleic Acid
<221> NAME/KEY: misc_feature
<222> LOCATION: (1)..(8)
<223> OTHER INFORMATION: 2'-O-Methyl
<221> NAME/KEY: misc_feature
```

```
<222> LOCATION: (11)..(12)
<223> OTHER INFORMATION: 2'-O-Methyl
<221> NAME/KEY: misc_feature
<222> LOCATION: (16)..(18)
<223> OTHER INFORMATION: 2'-O-Methyl
<221> NAME/KEY: misc_feature
<222> LOCATION: (21)..(27)
<223> OTHER INFORMATION: 2'-O-Methyl
<221> NAME/KEY: misc_feature
<222> LOCATION: (10)..(10)
<223> OTHER INFORMATION: 2'-deoxy-2'-fluoro
<221> NAME/KEY: misc_feature
<222> LOCATION: (28)..(28)
<223> OTHER INFORMATION: n stands for inverted deoxyabasic derivative

<400> SEQUENCE: 38
ggaguaagau aacgugaaga ucaggacn                                28

<210> SEQ ID NO 39
<211> LENGTH: 28
<212> TYPE: RNA
<213> ORGANISM: Artificial Sequence
<220> FEATURE:
<223> OTHER INFORMATION: Description of Artificial Sequence: Enzymatic
      Nucleic Acid
<221> NAME/KEY: misc_feature
<222> LOCATION: (1)..(9)
<223> OTHER INFORMATION: 2'-O-Methyl
<221> NAME/KEY: misc_feature
<222> LOCATION: (11)..(13)
<223> OTHER INFORMATION: 2'-O-Methyl
<221> NAME/KEY: misc_feature
<222> LOCATION: (16)..(19)
<223> OTHER INFORMATION: 2'-O-Methyl
<221> NAME/KEY: misc_feature
<222> LOCATION: (21)..(27)
<223> OTHER INFORMATION: 2'-O-Methyl
<221> NAME/KEY: misc_feature
<222> LOCATION: (28)..(28)
<223> OTHER INFORMATION: n stands for inverted deoxyabasic derivative

<400> SEQUENCE: 39
ggaguaagau aacgugaaga ucaggacn                                28

<210> SEQ ID NO 40
<211> LENGTH: 28
<212> TYPE: RNA
<213> ORGANISM: Artificial Sequence
<220> FEATURE:
<223> OTHER INFORMATION: Description of Artificial Sequence: Enzymatic
      Nucleic Acid
<221> NAME/KEY: misc_feature
<222> LOCATION: (1)..(9)
<223> OTHER INFORMATION: 2'-O-Methyl
<221> NAME/KEY: misc_feature
<222> LOCATION: (11)..(13)
<223> OTHER INFORMATION: 2'-O-Methyl
<221> NAME/KEY: misc_feature
<222> LOCATION: (16)..(19)
<223> OTHER INFORMATION: 2'-O-Methyl
<221> NAME/KEY: misc_feature
<222> LOCATION: (21)..(27)
<223> OTHER INFORMATION: 2'-O-Methyl
<221> NAME/KEY: misc_feature
<222> LOCATION: (10)..(10)
<223> OTHER INFORMATION: Phosphorothioate 3'-Internucleotide Linkage
<221> NAME/KEY: misc_feature
<222> LOCATION: (15)..(15)
<223> OTHER INFORMATION: Phosphorothioate 3'-Internucleotide Linkage
<221> NAME/KEY: misc_feature
<222> LOCATION: (28)..(28)
<223> OTHER INFORMATION: n stands for inverted deoxyabasic derivative

<400> SEQUENCE: 40
```

```
ggaguaagau aacgugaaga ucaggacn                    28
```

<210> SEQ ID NO 41
<211> LENGTH: 28
<212> TYPE: RNA
<213> ORGANISM: Artificial Sequence
<220> FEATURE:
<223> OTHER INFORMATION: Description of Artificial Sequence: Enzymatic
      Nucleic Acid
<221> NAME/KEY: misc_feature
<222> LOCATION: (1)..(9)
<223> OTHER INFORMATION: 2'-O-Methyl
<221> NAME/KEY: misc_feature
<222> LOCATION: (11)..(13)
<223> OTHER INFORMATION: 2'-O-Methyl
<221> NAME/KEY: misc_feature
<222> LOCATION: (16)..(18)
<223> OTHER INFORMATION: 2'-O-Methyl
<221> NAME/KEY: misc_feature
<222> LOCATION: (21)..(27)
<223> OTHER INFORMATION: 2'-O-Methyl
<221> NAME/KEY: misc_feature
<222> LOCATION: (10)..(10)
<223> OTHER INFORMATION: Phosphorothioate 3'-Internucleotide Linkage
<221> NAME/KEY: misc_feature
<222> LOCATION: (15)..(15)
<223> OTHER INFORMATION: Phosphorothioate 3'-Internucleotide Linkage
<221> NAME/KEY: misc_feature
<222> LOCATION: (28)..(28)
<223> OTHER INFORMATION: n stands for inverted deoxyabasic derivative

<400> SEQUENCE: 41

```
ggaguaagau aacgugaaga ucaggacn                    28
```

<210> SEQ ID NO 42
<211> LENGTH: 28
<212> TYPE: RNA
<213> ORGANISM: Artificial Sequence
<220> FEATURE:
<223> OTHER INFORMATION: Description of Artificial Sequence: Enzymatic
      Nucleic Acid
<221> NAME/KEY: misc_feature
<222> LOCATION: (1)..(9)
<223> OTHER INFORMATION: 2'-O-Methyl
<221> NAME/KEY: misc_feature
<222> LOCATION: (11)..(13)
<223> OTHER INFORMATION: 2'-O-Methyl
<221> NAME/KEY: misc_feature
<222> LOCATION: (16)..(19)
<223> OTHER INFORMATION: 2'-O-Methyl
<221> NAME/KEY: misc_feature
<222> LOCATION: (21)..(27)
<223> OTHER INFORMATION: 2'-O-Methyl
<221> NAME/KEY: misc_feature
<222> LOCATION: (10)..(10)
<223> OTHER INFORMATION: Phosphorothioate 3'-Internucleotide Linkage
<221> NAME/KEY: misc_feature
<222> LOCATION: (15)..(15)
<223> OTHER INFORMATION: 2'-deoxy-2'-amino
<221> NAME/KEY: misc_feature
<222> LOCATION: (28)..(28)
<223> OTHER INFORMATION: n stands for inverted deoxyabasic derivative

<400> SEQUENCE: 42

```
ggaguaagau aacgugaaga ucaggacn                    28
```

<210> SEQ ID NO 43
<211> LENGTH: 28
<212> TYPE: RNA
<213> ORGANISM: Artificial Sequence
<220> FEATURE:
<223> OTHER INFORMATION: Description of Artificial Sequence: Enzymatic
      Nucleic Acid
<221> NAME/KEY: misc_feature

```
<222> LOCATION: (1)..(9)
<223> OTHER INFORMATION: 2'-O-Methyl
<221> NAME/KEY: misc_feature
<222> LOCATION: (11)..(13)
<223> OTHER INFORMATION: 2'-O-Methyl
<221> NAME/KEY: misc_feature
<222> LOCATION: (16)..(18)
<223> OTHER INFORMATION: 2'-O-Methyl
<221> NAME/KEY: misc_feature
<222> LOCATION: (21)..(27)
<223> OTHER INFORMATION: 2'-O-Methyl
<221> NAME/KEY: misc_feature
<222> LOCATION: (10)..(10)
<223> OTHER INFORMATION: Phosphorothioate 3'-Internucleotide Linkage
<221> NAME/KEY: misc_feature
<222> LOCATION: (15)..(15)
<223> OTHER INFORMATION: 2'-deoxy-2'-amino
<221> NAME/KEY: misc_feature
<222> LOCATION: (28)..(28)
<223> OTHER INFORMATION: n stands for inverted deoxyabasic derivative

<400> SEQUENCE: 43
ggaguaagau aacgugaaga ucaggacn                                        28

<210> SEQ ID NO 44
<211> LENGTH: 28
<212> TYPE: RNA
<213> ORGANISM: Artificial Sequence
<220> FEATURE:
<223> OTHER INFORMATION: Description of Artificial Sequence:  Enzymatic
      Nucleic Acid
<221> NAME/KEY: misc_feature
<222> LOCATION: (1)..(9)
<223> OTHER INFORMATION: 2'-O-Methyl
<221> NAME/KEY: misc_feature
<222> LOCATION: (11)..(12)
<223> OTHER INFORMATION: 2'-O-Methyl
<221> NAME/KEY: misc_feature
<222> LOCATION: (16)..(18)
<223> OTHER INFORMATION: 2'-O-Methyl
<221> NAME/KEY: misc_feature
<222> LOCATION: (21)..(27)
<223> OTHER INFORMATION: 2'-O-Methyl
<221> NAME/KEY: misc_feature
<222> LOCATION: (10)..(10)
<223> OTHER INFORMATION: Phosphorothioate 3'-Internucleotide Linkage
<221> NAME/KEY: misc_feature
<222> LOCATION: (13)..(13)
<223> OTHER INFORMATION: 2'-deoxy-2'-fluoro
<221> NAME/KEY: misc_feature
<222> LOCATION: (15)..(15)
<223> OTHER INFORMATION: 2'-deoxy-2'-amino
<221> NAME/KEY: misc_feature
<222> LOCATION: (28)..(28)
<223> OTHER INFORMATION: n stands for inverted deoxyabasic derivative

<400> SEQUENCE: 44
ggaguaagau aacgugaaga ucaggacn                                        28

<210> SEQ ID NO 45
<211> LENGTH: 28
<212> TYPE: RNA
<213> ORGANISM: Artificial Sequence
<220> FEATURE:
<223> OTHER INFORMATION: Description of Artificial Sequence:  Enzymatic
      Nucleic Acid
<221> NAME/KEY: misc_feature
<222> LOCATION: (1)..(9)
<223> OTHER INFORMATION: 2'-O-Methyl
<221> NAME/KEY: misc_feature
<222> LOCATION: (11)..(12)
<223> OTHER INFORMATION: 2'-O-Methyl
<221> NAME/KEY: misc_feature
<222> LOCATION: (16)..(18)
<223> OTHER INFORMATION: 2'-O-Methyl
```

```
<221> NAME/KEY: misc_feature
<222> LOCATION: (21)..(27)
<223> OTHER INFORMATION: 2'-O-Methyl
<221> NAME/KEY: misc_feature
<222> LOCATION: (13)..(13)
<223> OTHER INFORMATION: Phosphorothioate 3'-Internucleotide Linkage
<221> NAME/KEY: misc_feature
<222> LOCATION: (28)..(28)
<223> OTHER INFORMATION: n stands for inverted deoxyabasic derivative

<400> SEQUENCE: 45
ggaguaagau aacgugaaga ucaggacn                                    28

<210> SEQ ID NO 46
<211> LENGTH: 28
<212> TYPE: RNA
<213> ORGANISM: Artificial Sequence
<220> FEATURE:
<223> OTHER INFORMATION: Description of Artificial Sequence: Enzymatic
      Nucleic Acid
<221> NAME/KEY: misc_feature
<222> LOCATION: (1)..(9)
<223> OTHER INFORMATION: 2'-O-Methyl
<221> NAME/KEY: misc_feature
<222> LOCATION: (11)..(13)
<223> OTHER INFORMATION: 2'-O-Methyl
<221> NAME/KEY: misc_feature
<222> LOCATION: (16)..(18)
<223> OTHER INFORMATION: 2'-O-Methyl
<221> NAME/KEY: misc_feature
<222> LOCATION: (21)..(27)
<223> OTHER INFORMATION: 2'-O-Methyl
<221> NAME/KEY: misc_feature
<222> LOCATION: (10)..(10)
<223> OTHER INFORMATION: Phosphorothioate 3'-Internucleotide Linkage
<221> NAME/KEY: misc_feature
<222> LOCATION: (15)..(15)
<223> OTHER INFORMATION: Phosphorothioate 3'-Internucleotide Linkage
<221> NAME/KEY: misc_feature
<222> LOCATION: (28)..(28)
<223> OTHER INFORMATION: n stands for inverted deoxyabasic derivative

<400> SEQUENCE: 46
ggaguaagau aacgugaaga ucaggacn                                    28

<210> SEQ ID NO 47
<211> LENGTH: 28
<212> TYPE: RNA
<213> ORGANISM: Artificial Sequence
<220> FEATURE:
<223> OTHER INFORMATION: Description of Artificial Sequence: Enzymatic
      Nucleic Acid
<221> NAME/KEY: misc_feature
<222> LOCATION: (1)..(9)
<223> OTHER INFORMATION: 2'-O-Methyl
<221> NAME/KEY: misc_feature
<222> LOCATION: (11)..(12)
<223> OTHER INFORMATION: 2'-O-Methyl
<221> NAME/KEY: misc_feature
<222> LOCATION: (16)..(19)
<223> OTHER INFORMATION: 2'-O-Methyl
<221> NAME/KEY: misc_feature
<222> LOCATION: (21)..(27)
<223> OTHER INFORMATION: 2'-O-Methyl
<221> NAME/KEY: misc_feature
<222> LOCATION: (10)..(10)
<223> OTHER INFORMATION: Phosphorothioate 3'-Internucleotide Linkage
<221> NAME/KEY: misc_feature
<222> LOCATION: (15)..(15)
<223> OTHER INFORMATION: Phosphorothioate 3'-Internucleotide Linkage
<221> NAME/KEY: misc_feature
<222> LOCATION: (13)..(13)
<223> OTHER INFORMATION: 2'-deoxy-2'-fluoro
<221> NAME/KEY: misc_feature
<222> LOCATION: (28)..(28)
```

```
<223> OTHER INFORMATION: n stands for inverted deoxyabasic derivative

<400> SEQUENCE: 47
ggaguaagau aacgugaaga ucaggacn                                          28

<210> SEQ ID NO 48
<211> LENGTH: 40
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 48
augcaaugca uuugagaacu guaaguugua ugagggcaug                             40

<210> SEQ ID NO 49
<211> LENGTH: 40
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 49
augugaugca uuugagaacu gcaaguugua ugagggcaug                             40

<210> SEQ ID NO 50
<211> LENGTH: 40
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 50
uugcaaugcc uuugagaacu gaaaguugua uuagggagug                             40

<210> SEQ ID NO 51
<211> LENGTH: 40
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 51
gugcaaugca uuugagaacu guaaguugua uuagggugug                             40

<210> SEQ ID NO 52
<211> LENGTH: 40
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 52
augcacugca uuugagaaca gaaaguugua ugagggagug                             40

<210> SEQ ID NO 53
<211> LENGTH: 40
<212> TYPE: RNA
<213> ORGANISM: Artificial Sequence
<220> FEATURE:
<223> OTHER INFORMATION: Description of Artificial Sequence:  Enzymatic
      Nucleic Acid
```

-continued

```
<400> SEQUENCE: 53
augcauugcg uuugagaacu ggaaguugaa ugagggcaug                40

<210> SEQ ID NO 54
<211> LENGTH: 40
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 54
gugcaaugca uuugagaacu ggaaguugua uuaggucaug                40

<210> SEQ ID NO 55
<211> LENGTH: 40
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 55
auguaaugca uuugagaacu caaaguugua uuagggcaug                40

<210> SEQ ID NO 56
<211> LENGTH: 40
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 56
augcaaugua uuugagaacc guaaguugua ucagggcaug                40

<210> SEQ ID NO 57
<211> LENGTH: 40
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 57
augcaaugca uuugagaacu cuaaguugua ugagggcgug                40

<210> SEQ ID NO 58
<211> LENGTH: 40
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 58
augcgaggca uuugagaacu ucaaguugua ugagggcaug                40

<210> SEQ ID NO 59
<211> LENGTH: 39
<212> TYPE: RNA
<213> ORGANISM: Artificial Sequence
<220> FEATURE:
<223> OTHER INFORMATION: Description of Artificial Sequence:  Enzymatic
      Nucleic Acid
```

```
<400> SEQUENCE: 59
augcauugca cuugagagcu gaaagcugau gagggcagg                              39

<210> SEQ ID NO 60
<211> LENGTH: 40
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 60
gugcaaugca uuugagaacu ggaaguugua uuagggcaua                             40

<210> SEQ ID NO 61
<211> LENGTH: 40
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 61
augcuaugca uuugagaacu gagaguugua uggggcacg                              40

<210> SEQ ID NO 62
<211> LENGTH: 40
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 62
augcagugcg uuugagaacu guaaguugua ucagggcagg                             40

<210> SEQ ID NO 63
<211> LENGTH: 40
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 63
gugcaaugca uuugagaacu guaaguugua ugagggcaug                             40

<210> SEQ ID NO 64
<211> LENGTH: 40
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 64
augaaaugca uuugagaacu ggaaguugua ugagggcagg                             40

<210> SEQ ID NO 65
<211> LENGTH: 40
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 65
```
gugcaaugca uuugagaacu gaaaguugua ugagggcauu          40

<210> SEQ ID NO 66
<211> LENGTH: 40
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 66
gugcaaugca uuugagaacu gaaaguugua uuaggucaug          40

<210> SEQ ID NO 67
<211> LENGTH: 40
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 67
ggcgauaggu gaguacacug ggucggaggg auagcuaggu          40

<210> SEQ ID NO 68
<211> LENGTH: 40
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 68
ggcgauaagu gcguacacug ggucggaggg acagcuaggu          40

<210> SEQ ID NO 69
<211> LENGTH: 40
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 69
ggcgauaagu gaguacacug ggucggaggg auagcuagga          40

<210> SEQ ID NO 70
<211> LENGTH: 40
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 70
ggcgauaggu caguacacug ggucggaggg auagcuaggu          40

<210> SEQ ID NO 71
<211> LENGTH: 40
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 71

-continued ggcgauaagu gagaacacug ggucggaggg auagcuaggu                    40

<210> SEQ ID NO 72
<211> LENGTH: 40
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 72
ggcgauaggu gaguacacug ggucggaggg aaagcuaggu                    40

<210> SEQ ID NO 73
<211> LENGTH: 40
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 73
ggcgauagau ggguacacug ggucggaggg auagggaggu                    40

<210> SEQ ID NO 74
<211> LENGTH: 40
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 74
ggcgauaagu gagaacacug ggucggaggg auagcuaggu                    40

<210> SEQ ID NO 75
<211> LENGTH: 40
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 75
ggcgauaggu gaauacacug ggucggaggg auagcuaaca                    40

<210> SEQ ID NO 76
<211> LENGTH: 40
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 76
ggcgauaggu gagugcacug ggucggaggg auugcuaguc                    40

<210> SEQ ID NO 77
<211> LENGTH: 40
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 77
ggcgauaggu gaauacacug ggucggaggg acggcuaggc                    40

```
<210> SEQ ID NO 78
<211> LENGTH: 40
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 78
ggcgauaggu gaguacacug ggucggaggg auagcguggu                         40

<210> SEQ ID NO 79
<211> LENGTH: 40
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 79
ggcgacaggu guuuacacug ggucggaggg auagcuaagc                         40

<210> SEQ ID NO 80
<211> LENGTH: 40
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 80
ggcgauaggu guguacacug ggucggaggg auagcuagcu                         40

<210> SEQ ID NO 81
<211> LENGTH: 40
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 81
ggcgauaggu gaguacacug ggucggaggg auaucgaggu                         40

<210> SEQ ID NO 82
<211> LENGTH: 40
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 82
ggcgauaggu gaguacacug ggucggaggg guaggaagau                         40

<210> SEQ ID NO 83
<211> LENGTH: 43
<212> TYPE: RNA
<213> ORGANISM: Artificial Sequence
<220> FEATURE:
<223> OTHER INFORMATION: Description of Artificial Sequence:  Enzymatic
      Nucleic Acid

<400> SEQUENCE: 83
ggcucguggg gagugagaua acgugaagau cuagggcggg gga                     43
```

<210> SEQ ID NO 84
<211> LENGTH: 43
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 84
ggcucgugcg gagugagaua acgugaagau cuagggcugg gga                43

<210> SEQ ID NO 85
<211> LENGTH: 43
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 85
ggcucguugg gggugagaua acgugaagau cuagggcggg uga                43

<210> SEQ ID NO 86
<211> LENGTH: 43
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 86
ugcuugugcg gagugagaua acgugaagau cgagggcagg gga                43

<210> SEQ ID NO 87
<211> LENGTH: 43
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 87
ggcucgugcg gaguaagaua acgugaagau cacgggcggu gca                43

<210> SEQ ID NO 88
<211> LENGTH: 43
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 88
ggcugguugg gagugagaua acgugaagau cuagggcggg uga                43

<210> SEQ ID NO 89
<211> LENGTH: 43
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 89
ggcucgcggg gagugagaua acgugaagau cuagggcggu gga                43

-continued

<210> SEQ ID NO 90
<211> LENGTH: 43
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 90
gacucguggg gaguaagaua acgugaagau cuugggcugg uga            43

<210> SEQ ID NO 91
<211> LENGTH: 43
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 91
ggcuuguuug gagugagaua acgugaagau cuagggcgcg cga            43

<210> SEQ ID NO 92
<211> LENGTH: 43
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 92
ggcucguggc gagugagaua acgugaagau auagggcggu ggu            43

<210> SEQ ID NO 93
<211> LENGTH: 43
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 93
ggcucguggg gaguaagaua acgugaagau cuaggguggc gga            43

<210> SEQ ID NO 94
<211> LENGTH: 43
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 94
ggcucguggg gagugagaua acgugaagau cuaggacugu agg            43

<210> SEQ ID NO 95
<211> LENGTH: 43
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 95
gacucguggg gagugagaua acgugaagau cuagggcgcg gua            43

<210> SEQ ID NO 96

```
<211> LENGTH: 43
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 96
ggcucguggg gagugagaua acgugaagau cuagggcggg cga                43

<210> SEQ ID NO 97
<211> LENGTH: 15
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 97
agauaacgug aagau                                               15

<210> SEQ ID NO 98
<211> LENGTH: 18
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 98
aauggccuau cggugcga                                            18

<210> SEQ ID NO 99
<211> LENGTH: 42
<212> TYPE: DNA
<213> ORGANISM: Artificial Sequence
<220> FEATURE:
<223> OTHER INFORMATION: Description of Artificial Sequence: Nucleic
      Acid Primer

<400> SEQUENCE: 99
gaaataaact cgcttggagt aaccatcagg acagcgaccg ta                 42

<210> SEQ ID NO 100
<211> LENGTH: 90
<212> TYPE: DNA
<213> ORGANISM: Artificial Sequence
<220> FEATURE:
<223> OTHER INFORMATION: Description of Artificial Sequence: Nucleic
      Acid Template
<221> NAME/KEY: misc_feature
<222> LOCATION: (35)..(74)
<223> OTHER INFORMATION: n stands for any a, c, g, or u

<400> SEQUENCE: 100
tctaatacga ctcactatag gaagacgtag ccaannnnnn nnnnnnnnnn nnnnnnnnnn    60
nnnnnnnnnn nnnntacggt cgctgtcctg                                    90

<210> SEQ ID NO 101
<211> LENGTH: 38
<212> TYPE: DNA
<213> ORGANISM: Artificial Sequence
<220> FEATURE:
<223> OTHER INFORMATION: Description of Artificial Sequence: Nucleic
      Acid Primer

<400> SEQUENCE: 101
```

```
                                                        -continued gaattctaat acgactcact ataggaagac gtagccaa                            38

<210> SEQ ID NO 102
<211> LENGTH: 97
<212> TYPE: RNA
<213> ORGANISM: Artificial Sequence
<220> FEATURE:
<223> OTHER INFORMATION: Description of Artificial Sequence: Enzymatic
      Nucleic Acid
<221> NAME/KEY: misc_feature
<222> LOCATION: (16)..(55)
<223> OTHER INFORMATION: n stands for any a, c, g, or u

<400> SEQUENCE: 102
ggaagacgua gccaannnnn nnnnnnnnnn nnnnnnnnnn nnnnnnnnnn nnnnnuacgg     60
ucgcuguccu gaugguuacu ccaagcgagu uuauuug                             97

<210> SEQ ID NO 103
<211> LENGTH: 21
<212> TYPE: RNA
<213> ORGANISM: Artificial Sequence
<220> FEATURE:
<223> OTHER INFORMATION: Description of Artificial Sequence: Nucleic
      Acid Substrate

<400> SEQUENCE: 103
guccugaugg uuacuccaag c                                              21

<210> SEQ ID NO 104
<211> LENGTH: 46
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 104
gguagccaag ugcaaugcac uugagaacug uaaguuguau uagggc                   46

<210> SEQ ID NO 105
<211> LENGTH: 44
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 105
gguagccaag gcgauaagug aguacacugg gucggaggga uagc                     44

<210> SEQ ID NO 106
<211> LENGTH: 45
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 106
gguagccaag gcgcuggcac aagcguugcu gaucggaagg gacag                    45

<210> SEQ ID NO 107
<211> LENGTH: 29
<212> TYPE: RNA
<213> ORGANISM: Artificial Sequence
<220> FEATURE:
<223> OTHER INFORMATION: Description of Artificial Sequence: Enzymatic
```

-continued

Nucleic Acid

<400> SEQUENCE: 107
gguagccaau ggccuaucgg ugcgaggac                                29

<210> SEQ ID NO 108
<211> LENGTH: 28
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 108
ggaguaagau aacgugaaga ucuaggac                                 28

<210> SEQ ID NO 109
<211> LENGTH: 61
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 109
ggaguagcau cccugagau gggguagag cgaauacggu cgcuguccug augguuacuc    60
c                                                                 61

<210> SEQ ID NO 110
<211> LENGTH: 13
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 110
cuuguggcgc guc                                                 13

<210> SEQ ID NO 111
<211> LENGTH: 49
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 111
ggaagacgua gccaaggugc ugcggagagu guguuaggca cuguaggac            49

<210> SEQ ID NO 112
<211> LENGTH: 37
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 112
ggcuuggagc ugaagaggaa ucaaacccga aaacuac                       37

<210> SEQ ID NO 113
<211> LENGTH: 50
<212> TYPE: RNA
<213> ORGANISM: Artificial Sequence
<220> FEATURE:

<223> OTHER INFORMATION: Description of Artificial Sequence: Enzymatic
      Nucleic Acid

<400> SEQUENCE: 113
ggaagacacg uagccaaaca guaggcuaug gagauccgga aagagcggau        50

<210> SEQ ID NO 114
<211> LENGTH: 30
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 114
gcuuggagcc gguggugca uagucaggac        30

<210> SEQ ID NO 115
<211> LENGTH: 35
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 115
ggcuuggagu guggcgauuc agaucggagu uggac        35

<210> SEQ ID NO 116
<211> LENGTH: 17
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 116
gaugguuacu ccaagcg        17

<210> SEQ ID NO 117
<211> LENGTH: 39
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 117
ggaguaaccg uucgcgagag ccuuaagcug uaucaggac        39

<210> SEQ ID NO 118
<211> LENGTH: 17
<212> TYPE: RNA
<213> ORGANISM: Artificial Sequence
<220> FEATURE:
<223> OTHER INFORMATION: Description of Artificial Sequence: Nucleic
      Acid Substrate

<400> SEQUENCE: 118
agacgaaugg ucagacg        17

<210> SEQ ID NO 119
<211> LENGTH: 17
<212> TYPE: RNA
<213> ORGANISM: Artificial Sequence
<220> FEATURE:
<223> OTHER INFORMATION: Description of Artificial Sequence: Nucleic Acid Substrate

<400> SEQUENCE: 119
cacguuaugg cucaacg                                                17

<210> SEQ ID NO 120
<211> LENGTH: 27
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 120
caaugugaau ugagagccuu aagcugu                                     27

<210> SEQ ID NO 121
<211> LENGTH: 47
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 121
ggagacguag ccaaggucug cggagagugu guuaggcacu guaggac               47

<210> SEQ ID NO 122
<211> LENGTH: 30
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 122
gcuuggagcu gaggagaugu ucgaaaacca                                  30

<210> SEQ ID NO 123
<211> LENGTH: 96
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 123
ggaagacgua gccaauguga auugagagcc uuaagcugua ucagagagug uacauacggu   60
cgcuguccug augguuacuc caagcgaguu uauuug                           96

<210> SEQ ID NO 124
<211> LENGTH: 43
<212> TYPE: RNA
<213> ORGANISM: Artificial Sequence
<220> FEATURE:
<223> OTHER INFORMATION: Description of Artificial Sequence: Enzymatic
      Nucleic Acid

<400> SEQUENCE: 124
ggaguagcca augugaauug agagccuuaa gcuguaucag gac                   43

<210> SEQ ID NO 125
<211> LENGTH: 17
<212> TYPE: RNA
<213> ORGANISM: Artificial Sequence
<220> FEATURE:

-continued

```
<223> OTHER INFORMATION: Description of Artificial Sequence:  Nucleic
      Acid Substrate

<400> SEQUENCE: 125
guccugaugg uuacucc                                                    17

<210> SEQ ID NO 126
<211> LENGTH: 27
<212> TYPE: RNA
<213> ORGANISM: Artificial Sequence
<220> FEATURE:
<223> OTHER INFORMATION: Description of Artificial Sequence:  Enzymatic
      Nucleic Acid
<221> NAME/KEY: misc_feature
<222> LOCATION: (1)..(6)
<223> OTHER INFORMATION: 2'-O-Methyl
<221> NAME/KEY: misc_feature
<222> LOCATION: (21)..(27)
<223> OTHER INFORMATION: 2'-O-Methyl

<400> SEQUENCE: 126
ggaguaagau aacgugaaga ucaggac                                         27
```

NUCLEIC ACID CATALYSTS WITH ENDONUCLEASE ACTIVITY

BACKGROUND OF THE INVENTION

This patent application claims priority from Breaker et al., U.S. Ser. No. (60/181,360), filed Feb. 8, 2000, entitled "NUCLEIC ACID CATALYSTS WITH ENDONUCLEASE ACTIVITY". This patent application is hereby incorporated by reference herein in its entirety including the drawings.

This invention relates to nucleic acid molecules with catalytic activity and derivatives thereof.

The following is a brief description of enzymatic nucleic acid molecules. This summary is not meant to be complete but is provided only for understanding of the invention that follows. This summary is not an admission that all of the work described below is prior art to the claimed invention.

Enzymatic nucleic acid molecules (e.g., ribozymes) are nucleic acid molecules capable of catalyzing one or more of a variety of reactions, including the ability to repeatedly cleave other separate nucleic acid molecules in a nucleotide base sequence-specific manner. Such enzymatic nucleic acid molecules can be used, for example, to target virtually any RNA transcript (Zaug et al., 324, *Nature* 429 1986; Cech, 260 *JAMA* 3030, 1988; and Jefferies et al., 17 *Nucleic Acids Research* 1371, 1989).

Because of their sequence-specificity, trans-cleaving enzymatic nucleic acid molecules show promise as therapeutic agents for human disease (Usman & McSwiggen, 1995 *Ann. Rep. Med. Chem.* 30, 285–294; Christoffersen and Marr, 1995 *J. Med. Chem.* 38, 2023–2037). Enzymatic nucleic acid molecules can be designed to cleave specific RNA targets within the background of cellular RNA. Such a cleavage event renders the mRNA non-functional and abrogates protein expression from that RNA. In this manner, synthesis of a protein associated with a disease state can be selectively inhibited.

In general, enzymatic nucleic acids with RNA cleaving activity act by first binding to a target RNA. Such binding occurs through the target binding portion of a enzymatic nucleic acid which is held in close proximity to an enzymatic portion of the molecule that acts to cleave the target RNA. Thus, the enzymatic nucleic acid first recognizes and then binds a target RNA through complementary base pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets.

Several approaches such as in vitro selection (evolution) strategies (Orgel, 1979, *Proc. R. Soc. London*, B 205, 435) have been used to evolve new nucleic acid catalysts capable of catalyzing a variety of reactions, such as cleavage and ligation of phosphodiester linkages and amide linkages, (Joyce, 1989, *Gene*, 82, 83–87; Beaudry et al., 1992, *Science* 257, 635–641; Joyce, 1992, *Scientific American* 267, 90–97; Breaker et al., 1994, *TIBTECH* 12, 268; Bartel et al., 1993, *Science* 261:1411–1418; Szostak, 1993, *TIBS* 17, 89–93; Kumar et al., 1995, *FASEB J.*, 9, 1183; Breaker, 1996, *Curr. Op. Biotech.*, 7, 442).

The development of ribozymes that are optimal for catalytic activity would contribute significantly to any strategy that employs RNA-cleaving ribozymes for the purpose of regulating gene expression. The hammerhead ribozyme, for example, functions with a catalytic rate ($k_{cat}$) of ~1 min$^{-1}$ in the presence of saturating (10 mM) concentrations of Mg$^{2+}$ cofactor. However, the rate for this ribozyme in Mg$^{2+}$ concentrations that are closer to those found inside cells (0.5–2 mM) can be 10- to 100-fold slower. In contrast, the RNase P holoenzyme can catalyze pre-tRNA cleavage with a $k_{cat}$ of ~30 min$^{-1}$ under optimal assay conditions. An artificial 'RNA ligase' ribozyme has been shown to catalyze the corresponding self-modification reaction with a rate of ~100 min$^{-1}$. In addition, it is known that certain modified hammerhead ribozymes that have substrate binding arms made of DNA catalyze RNA cleavage with multiple turn-over rates that approach 100 min$^{-1}$. Finally, replacement of a specific residue within the catalytic core of the hammerhead with certain nucleotide analogues gives modified ribozymes that show as much as a 10-fold improvement in catalytic rate. These findings demonstrate that ribozymes can promote chemical transformations with catalytic rates that are significantly greater than those displayed in vitro by most natural self-cleaving ribozymes. It is then possible that the structures of certain self-cleaving ribozymes may be optimized to give maximal catalytic activity, or that entirely new RNA motifs can be made that display significantly faster rates for RNA phosphodiester cleavage.

An extensive array of site-directed mutagenesis studies have been conducted with ribozymes such as the hammerhead ribozyme and the hairpin ribozyme to probe relationships between nucleotide sequence and catalytic activity. These systematic studies have made clear that most nucleotides in the conserved core of the ribozyme cannot be mutated without significant loss of catalytic activity. In contrast, a combinatorial strategy that simultaneously screens a large pool of mutagenized ribozymes for RNAs that retain catalytic activity could be used more efficiently to define immutable sequences and to identify new ribozyme variants.

Tang et al, 1997, *RNA* 3, 914, reported novel ribozyme sequences with endonuclease activity, where the authors used an in vitro selection approach to isolate these ribozymes.

Vaish et al., 1998 PNAS 95, 2158–2162, describes the in vitro selection of a hammerhead-like ribozyme with an extended range of cleavable triplets.

Breaker, International PCT publication No. WO 98/43993, describes the in vitro selection of hammerhead-like ribozymes with sequence variants encompassing the catalytic core.

The references cited above are distinct from the presently claimed invention since they do not disclose and/or contemplate the catalytic nucleic acid molecules of the instant invention.

SUMMARY OF THE INVENTION

This invention relates to nucleic acid molecules with catalytic activity, which are particularly useful for cleavage of RNA or DNA. The nucleic acid catalysts of the instant invention are distinct from other nucleic acid catalysts known in the art. The nucleic acid catalysts of the instant invention do not share sequence homology with other known ribozymes. Specifically, nucleic acid catalysts of the instant invention are capable of catalyzing an intermolecular or intramolecular endonuclease reaction.

In a preferred embodiment, the invention features a nucleic acid molecule with catalytic activity having either the formulae I and II:

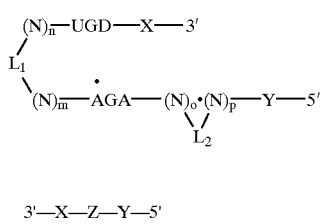

Formula I

3'—X—Z—Y—5'    Formula II

In the above formulae, each N represents independently a nucleotide or a non-nucleotide linker, which may be same or different; X and Y are independently oligonucleotides of length sufficient to stably interact (e.g., by forming hydrogen bonds with complementary nucleotides in the target) with a target nucleic acid molecule (the target can be an RNA, DNA or RNA/DNA mixed polymers, including polymers that may include base, sugar, and/or phosphate nucleotide modifications; such modifications are preferably naturally occurring modifications), preferably, the length of X and Y are independently between 3–20 nucleotides long, e.g., specifically, 3, 4, 5, 6, 7, 8, 9, 10, 11, 12, 13, 14, 15, 17, and 20); X and Y may have the same lengths or may have different lengths; m, n, o, and p are integers independently greater than or equal to 1 and preferably less than about 100, specifically 2, 3, 4, 5, 6, 7, 8, 9, 10, 15, 20, 25, 30, 35, 50; wherein if $(N)_m$ and $(N)_n$ and/or $(N)_o$ and $(N)_p$ are nucleotides, (N)m and (N)n and/or $(N)_o$ and $(N)_p$ are optionally able to interact by hydrogen bond interaction; preferably, (N)m and (N)n and/or $(N)_{o\ and\ (N)p}$ independently form 1, 2, 3, 4, 5, 6, 7, 8, 9 base-paired stem structures; D is U, G or A; $L_1$ and $L_2$ are independently linkers, which may be the same or different and which may be present or absent (i.e., the molecule is assembled from two separate molecules), but when present, are nucleotide and/or non-nucleotide linkers, which may comprise a single-stranded and/or double-stranded region; _____ represents a chemical linkage (e.g. a phosphate ester linkage, amide linkage or others known in the art); * represents a base-pair interaction; Z is independently a nucleotide sequence selected from the group comprising 5'-AGAUAACGUGAAGAU-3' (SEQ ID NO 97) and 5'-AAUGGCCUAUCGGUGCGA-3' (SEQ ID NO 98), additions, deletions, and substitutions to these sequences may be made without significantly altering the activity of the molecules and are hence within the scope of the invention; and C, G, A, and U represent cytidine, guanosine, adenosine and uridine nucleotides, respectively. The nucleotides in each of the formulae I and II are unmodified or modified at the sugar, base, and/or phosphate as known in the art.

In a preferred embodiment, the invention features nucleic acid molecules of Formula I, where the sequence of oligonucleotide $(N)_m$ is selected from the group consisting of 5'-AC-3', 5'-GC-3', and 5'-CG-3'.

In another preferred embodiment, the invention features nucleic acid molecules of Formula I, where the sequence of oligonucleotide $(N)_n$ is selected from the group consisting of 5'-GU-3', 5'-GC-3', and 5'-CG-3'.

In yet another preferred embodiment, the invention features nucleic acid molecules of Formula I, where the sequence of oligonucleotide $(N)_o$ is selected from the group consisting of 5'-AUUG-3', 5'-UUG-3', 5'-UUC-3', and 5'-UAG-3'.

In an additional preferred embodiment, the invention features nucleic acid molecules of Formula I, where the sequence of oligonucleotide $(N)_p$ is selected from the group consisting of 5'-CAAU-3', 5'-CAA-3', 5'-GAA-3', and 5'-CUA-3'.

In another embodiment, the nucleotide linker ($L_1$) is a nucleic acid sequence selected from the group consisting of 5'-CUUAA-3' and 5'-CUAAA-3'.

In another embodiment, the nucleotide linker ($L_2$) is a nucleic acid sequence selected from the group consisting of 5'-UGUGAA-3' and 5'-GUGA-3'.

In yet another embodiment, the nucleotide linker ($L_1$ and/or $L_2$) is a nucleic acid aptamer, such as an ATP aptamer, HIV Rev aptamer (RRE), HIV Tat aptamer (TAR) and others (for a review see Gold et al., 1995, *Annu. Rev. Biochem.*, 64, 763; and Szostak & Ellington, 1993, in *The RNA World*, ed. Gesteland and Atkins, pp. 511, CSH Laboratory Press). A "nucleic acid aptamer" as used herein is meant to indicate a nucleic acid sequence capable of interacting with a ligand. The ligand can be any natural or synthetic molecule, including but not limited to a resin, metabolites, nucleosides, nucleotides, drugs, toxins, transition state analogs, peptides, lipids, proteins, amino acids, nucleic acid molecules, hormones, carbohydrates, receptors, cells, viruses, bacteria and others.

In another embodiment, the non-nucleotide linker ($L_1$ and/or $L_2$) is as defined herein. The term "non-nucleotide" as used herein include either abasic nucleotide, polyether, polyamine, polyamide, peptide, carbohydrate, lipid, or polyhydrocarbon compounds. These compounds can be incorporated into a nucleic acid chain in the place of one or more nucleotide units, including either sugar and/or phosphate substitutions, and allows the remaining bases to exhibit their enzymatic activity. The group or compound is abasic in that it does not contain a commonly recognized nucleotide base, such as adenine, guanine, cytosine, uracil or thymine. The terms "abasic" or "abasic nucleotide" as used herein encompass sugar moieties lacking a base or having other chemical groups in place of a nucleotide base at the 1' position. Specific examples of non-nucleotides include those described by Seela and Kaiser, *Nucleic Acids Res.* 1990, 18:6353 and *Nucleic Acids Res.* 1987, 15:3113; Cload and Schepartz, *J. Am. Chem. Soc.* 1991, 113:6324; Richardson and Schepartz, *J. Am. Chem. Soc.* 1991, 113:5109; Ma et al., *Nucleic Acids Res.* 1993, 21:2585 and *Biochemistry* 1993, 32:1751; Durand et al., *Nucleic Acids Res.* 1990, 18:6353; McCurdy et al., *Nucleosides & Nucleotides* 1991, 10:287; Jschke et al., *Tetrahedron Lett.* 1993, 34:301; Ono et al., *Biochemistry* 1991, 30:9914; Arnold et al., International Publication No. WO 89/02439; Usman et al., International Publication No. WO 95/06731; Dudycz et al., International Publication No. WO 95/11910 and Ferentz and Verdine, *J. Am. Chem. Soc.* 1991, 113:4000, all hereby incorporated by reference herein. Thus, in a preferred embodiment, the invention features an enzymatic nucleic acid molecule having one or more non-nucleotide moieties, and having enzymatic activity to cleave an RNA or DNA molecule.

In preferred embodiments, the enzymatic nucleic acid includes one or more stretches of RNA, which provide the enzymatic activity of the molecule, linked to the non-nucleotide moiety. The necessary RNA components are known in the art (see for e.g., Usman et al., supra). By RNA is meant a molecule comprising at least one ribonucleotide residue. By "ribonucleotide" is meant a nucleotide with a hydroxyl group at the 2' position of the β-D-ribo-furanose moiety.

Thus, in one preferred embodiment, the invention features ribozymes that inhibit gene expression and/or cell proliferation. These chemically or enzymatically synthesized nucleic acid molecules contain substrate binding domains that bind to accessible regions of specific target nucleic acid molecules. The nucleic acid molecules also contain domains that catalyze the cleavage of target. Upon binding, the enzymatic nucleic acid molecules cleave the target molecules, preventing, for example, translation and protein accumulation. In the absence of the expression of the target gene, cell proliferation, for example, is inhibited. In another aspect of the invention, enzymatic nucleic acid molecules that cleave target molecules are expressed from transcription units inserted into DNA or RNA vectors. The recombinant vectors are preferably DNA plasmids or viral vectors. Ribozyme expressing viral vectors can be constructed based on, but not limited to, adeno-associated virus, retrovirus, adenovirus, or alphavirus. Preferably, the recombinant vectors capable of expressing the ribozymes are delivered as described below, and persist in target cells. Alternatively, viral vectors can be used that provide for transient expression of ribozymes. Such vectors can be repeatedly administered as necessary. Once expressed, the ribozymes cleave the target mRNA. Delivery of ribozyme expressing vectors can be systemic, such as by intravenous or intramuscular administration, by administration to target cells ex-planted from the patient followed by reintroduction into the patient, or by any other means that would allow for introduction into the desired target cell (for a review, see Couture and Stinchcomb, 1996, TIG., 12, 510).

As used herein "cell" is used in its usual biological sense, and does not refer to an entire multicellular organism, e.g., specifically does not refer to a human. The cell may be present in an organism, preferably a non-human multicellular organism, e.g., birds, plants and mammals such as cows, sheep, apes, monkeys, swine, dogs, and cats. The cell may be prokaryotic (e.g. bacterial cell) or eukaryotic (e.g., mammalian or plant cell).

In a preferred embodiment, an expression vector comprising a nucleic acid sequence encoding at least one of the nucleic acid catalysts of the instant invention is disclosed. The nucleic acid sequence encoding the nucleic acid catalyst of the instant invention is operable linked in a manner which allows expression of that nucleic acid molecule.

In one embodiment, the expression vector comprises: a transcription initiation region (e.g., eukaryotic pol I, II or III initiation region); b) a transcription termination region (e.g., eukaryotic pol I, II or III termination region); c) a nucleic acid sequence encoding at least one of the nucleic acid catalyst of the instant invention; and wherein said sequence is operably linked to said initiation region and said termination region, in a manner which allows expression and/or delivery of said nucleic acid molecule. The vector may optionally include an open reading frame (ORF) for a protein operably linked on the 5' side or the 3'-side of the sequence encoding the nucleic acid catalyst of the invention; and/or an intron (intervening sequences).

By "patient" is meant an organism which is a donor or recipient of explanted cells or the cells themselves. "Patient" also refers to an organism to which enzymatic nucleic acid molecules can be administered. Preferably, a patient is a mammal or mammalian cells. More preferably, a patient is a human or human cells.

By "vectors" is meant any nucleic acid- and/or viral-based technique used to deliver a desired nucleic acid.

Another means of accumulating high concentrations of a ribozyme(s) within cells is to incorporate the ribozyme-encoding sequences into a DNA or RNA expression vector. Transcription of the ribozyme sequences are driven from a promoter for eukaryotic RNA polymerase I (pol I), RNA polymerase II (pol II), or RNA polymerase III (pol III). Transcripts from pol II or pol III promoters will be expressed at high levels in all cells; the levels of a given pol II promoter in a given cell type will depend on the nature of the gene regulatory sequences (enhancers, silencers, etc.) present nearby. Prokaryotic RNA polymerase promoters are also used, providing that the prokaryotic RNA polymerase enzyme is expressed in the appropriate cells (Elroy-Stein and Moss, 1990 *Proc. Natl. Acad. Sci. USA*, 87, 6743–7; Gao and Huang 1993 *Nucleic Acids Res.*, 21, 2867–72; Lieber et al., 1993 *Methods Enzymol.*, 217, 47–66; Zhou et al., 1990 *Mol. Cell. Biol.*, 10, 4529–37). Several investigators have demonstrated that ribozymes expressed from such promoters can function in mammalian cells (e.g. Kashani-Sabet et al., 1992 *Antisense Res. Dev.*, 2, 3–15; Ojwang et al., 1992 *Proc. Natl. Acad. Sci. USA*, 89, 10802–6; Chen et al., 1992 *Nucleic Acids Res.*, 20, 4581–9; Yu et al., 1993 *Proc. Natl. Acad. Sci. USA*, 90, 6340–4; L'Huillier et al., 1992 *EMBO J.* 11, 4411–8; Lisziewicz et al., 1993 *Proc. Natl. Acad. Sci. U.S.A.*, 90, 8000–4; Thompson et al., 1995 *Nucleic Acids Res.* 23, 2259; Sullenger & Cech, 1993, *Science*, 262, 1566). The above ribozyme transcription units can be incorporated into a variety of vectors for introduction into mammalian cells, including but not restricted to, plasmid DNA vectors, viral DNA vectors (such as adenovirus or adeno-associated virus vectors), or viral RNA vectors (such as retroviral or alphavirus vectors) (for a review see Couture and Stinchcomb, 1996, supra).

In another preferred embodiment, catalytic activity of the molecules described in the instant invention can be optimized. Modifications which enhance their efficacy in cells, and removal of bases from stem loop structures to shorten RNA synthesis times and reduce chemical requirements are desired. Catalytic activity of the molecules described in the instant invention can be optimized as described by Draper et al., supra. The details will not be repeated here, but include altering the length of the ribozyme binding arms, or chemically synthesizing ribozymes with modifications (base, sugar and/or phosphate) that prevent their degradation by serum ribonucleases and/or enhance their enzymatic activity (see e.g., Eckstein et al., International Publication No. WO 92/07065; Perrault et al., 1990 *Nature* 344, 565; Pieken et al., 1991 *Science* 253, 314; Usman and Cedergren, 1992 *Trends in Biochem. Sci*. 17, 334; Usman et al., International Publication No. WO 93/15187; and Rossi et al., International Publication No. WO 91/03162; Sproat, U.S. Pat. No. 5,334,711; and Burgin et al., supra; all of these describe various chemical modifications that can be made to the base, phosphate and/or sugar moieties of enzymatic RNA molecules). All these publications are hereby incorporated by reference herein.

By "enhanced enzymatic activity" is meant to include activity measured in cells and/or in vivo where the activity is a reflection of both catalytic activity and ribozyme stability. In this invention, the product of these properties is increased or not significantly (less than 10-fold) decreased in vivo compared to an all RNA ribozyme.

In yet another preferred embodiment, nucleic acid catalysts having chemical modifications which maintain or enhance enzymatic activity is provided. Such nucleic acid is also generally more resistant to nucleases than unmodified nucleic acid. Thus, in a cell and/or in vivo the activity may not be significantly lowered. As exemplified herein such ribozymes are useful in a cell and/or in vivo even if activity over all is reduced 10-fold (Burgin et al., 1996, *Biochemistry*, 35, 14090). Such ribozymes herein are said to "maintain" the enzymatic activity of an all RNA ribozyme.

Other features and advantages of the invention will be apparent from the following description of the preferred embodiments thereof, and from the claims.

DESCRIPTION OF THE PREFERRED EMBODIMENTS

The drawings will first briefly be described.

Drawings

FIG. 1A is a diagram that shows a selection scheme for the isolation of self-cleaving ribozymes from a random-sequence RNA population. (I) RNAs are incubated under permissive reaction conditions. (II) The 5' fragments of cleaved RNAs are separated from uncleaved precursors by denaturing 10% PAGE and recovered by crush/soaking from the appropriate gel section. (III) The recovered RNA fragments are amplified by RT-PCR, which introduces a T7 promoter sequence and restores the nucleotides that were lost upon ribozyme cleavage. The resulting double-stranded DNAs are transcribed by T7 RNAP to generate the subsequent population of RNAs. FIG. 1B is a diagram of the RNA construct used to initiate the in vitro selection process. $N_{40}$ depicts 40 random-sequence positions. Underlined nucleotides identify the region that represents all 16 possible nearest neighbor combinations.

FIG. 2 is a diagram that shows non-limiting secondary-structure models for different classes of self-cleaving ribozymes of this invention. For each class (I-XII), the generation of its first appearance in the selection process (see FIG. 1) is encircled. In addition, the cleavage sites (arrowheads) and observed rate constants are given for all RNA constructs as depicted. In some cases, secondary-structure models are based on artificial phylogenetic data (e.g. see Table VIII) or otherwise reflect the most stable structure predicted by the Zuker RNA mfold program that is accessible on the Internet (www.ibc.wustl.edu/~mfold/rna/forml.cgi). Putative Watson/Crick base pairing interactions are represented by dashes and putative G•U wobble interactions are represented by dots. Note that classes VI and VII were examined as unimolecular constructs. No reasonable secondary-structure model was established for class VII ribozymes. In this case, the boxed regions identify variable (shaded) or conserved nucleotides that reside in the original random-sequence domain. The nucleotides of the hammerhead ribozyme (class VIII) are numbered according to the system suggested by Hertel et al. (Hertel et al., 1992, *Nucleic Acids Research*, 20, 3252).

FIG. 3A is a diagram showing cleavage reaction profiles for bimolecular class I (open circles) and class II (filled circles) ribozymes as depicted in FIG. 2 under the permissive reaction conditions. Observed rate constants for class I and class II ribozymes are 0.01 and 0.05 $min^{-1}$, respectively, as determined by the negative slope of the lines. FIG. 3B shows a compilation of the cleavage sites of the 12 classes of ribozymes. Numbers identify the nucleotides within the nearest-neighbor domain depicted in FIG. 1B.

FIG. 4 shows a comparison of the secondary structures of two hammerhead ribozymes and the dominant X motif. FIG. 4A is a diagram of two distinct versions (i and ii) of the hammerhead ribozyme which were isolated and examined for catalytic activity with S21 substrate. Both variants retain the highly conserved catalytic core, which is known to tolerate sequence variation only at position 7 (Tang and Breaker, 1997, *RNA*, 3, 914–925). Stem elements and nucleotides in (I) are numbered according to the nomenclature defined by Hertel et al. (Hertel et al., supra). FIG. 4B shows the dominant unimolecular construct isolated after a total of 25 rounds of in vitro selection conforms to the X-motif (class I) class of self-cleaving ribozymes. This self-cleaving ribozyme can be reorganized into a bimolecular format wherein separate substrate RNAs (S21) are cleaved by a 43-nt enzyme domain, the latter which encompasses all highly conserved nucleotides that were identified during reselection (Table VIII). Enzyme-substrate interactions result from the formation of two (stems I and IV) of the four putative helical regions that define the motif. Arrowheads identify the sites of ribozyme-mediated cleavage.

FIG. 5 is a demonstration of cleavage site versatility of the X motif ribozyme. FIG. 5 shows three different 43-nt RNAs carrying the conserved core of the X motif class of ribozymes were generated by in vitro transcription such that each differed in the base pairing potential of binding arms I and IV. Specifically, ribozyme X-E1 is engineered to form eight base pairs that flank both the 5' and 3' sides of an unpaired G reside. The lines represent nucleotides within binding arms I and IV that are complementary to the X-E1 target site (depicted by the arrow). Similarly, ribozymes X-E2 and X-E3 carry the corresponding binding arm sequences that allow base pairing only with their corresponding target sites. Base pairing interactions are depicted by dashes.

FIG. 6 is a representative diagram of a Class V ribozyme motif which shows the effect of sequential 2'-O-methyl substitutions on $K_{obs}$ in the ribozyme core. FIG. 6 also shows a typical site of substrate cleavage for the Class V ribozyme as well as the numbering system used in this application for describing modifications to this class of ribozyme as described in Tables II–VI.

FIG. 7 is a representative diagram of structural similarities between Class I (SEQ ID NO 117), (substrate SEQ ID NO 103) and Class VIII (SEQ ID NO 121), (substrate SEQ ID NO 103) enzymatic nucleic acid molecules of the invention.

Figure 8:
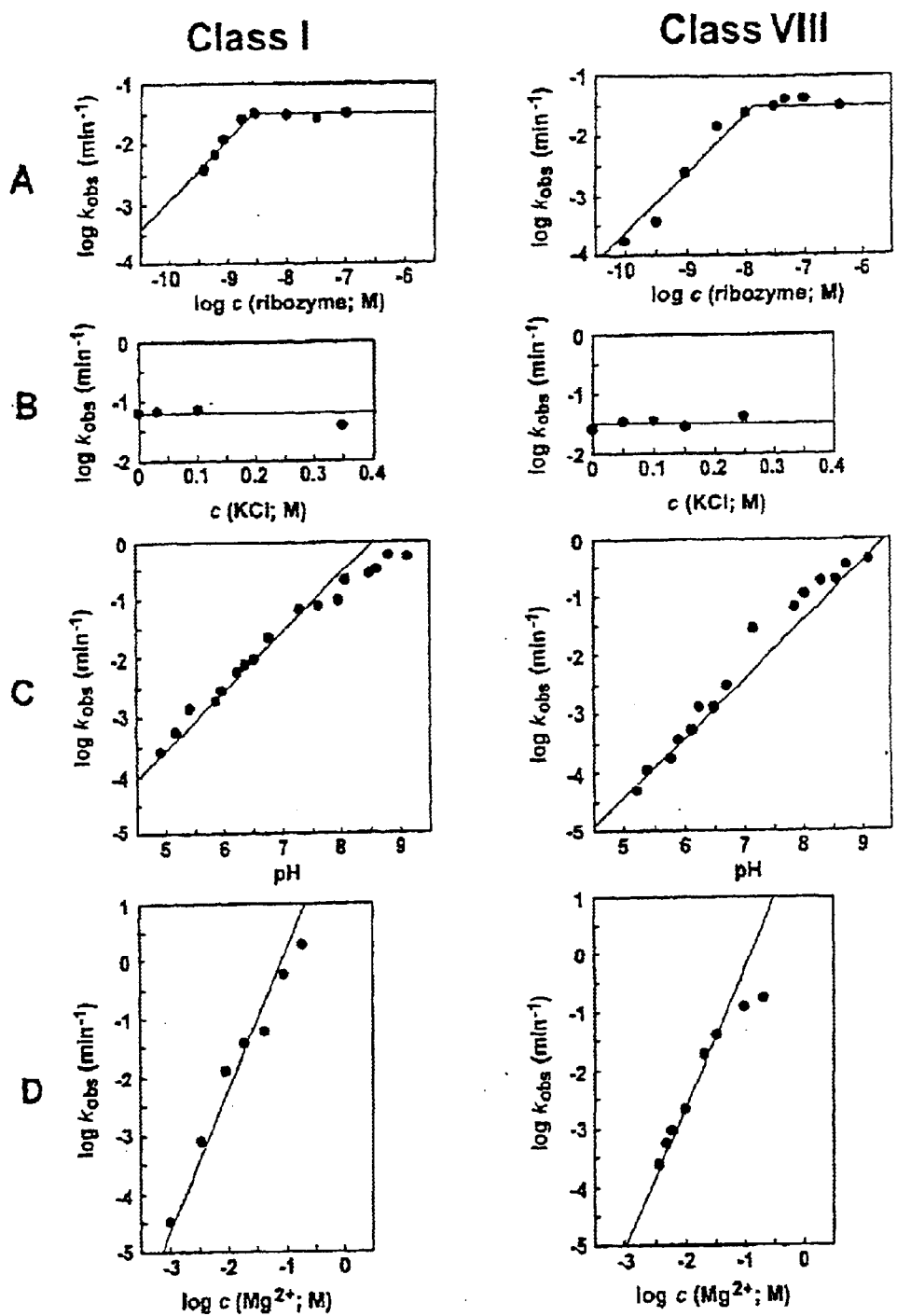

FIG. 8 is a comparison of the kinetic characteristics of the Class I and Class VIII enzymatic nucleic acid molecules of the invention. (A) Saturation of substrate with enzymes based on Class I motif and Class VIII motif enzymes, respectively. (B) Influence of monovalent ions on ribozyme activity. (C) Magnesium dependence of each ribozyme. Reactions were conducted in 50 mM Tris-HCl (pH 7.5 at 23° C.), and 20 mM magnesium chloride unless otherwise indicated.

Nucleic Acid Catalysts

The invention provides nucleic acid catalysts and methods for producing a class of enzymatic nucleic acid cleaving agents which exhibit a high degree of specificity for the nucleic acid sequence of a desired target. The enzymatic nucleic acid molecule is preferably targeted to a highly conserved sequence region of a target such that specific diagnosis and/or treatment of a disease or condition in a variety of biological systems can be provided with a single enzymatic nucleic acid. Such enzymatic nucleic acid molecules can be delivered exogenously to specific cells as required. In the preferred Class I and V motifs, the small size (less than 60 nucleotides, preferably between 25–40 nucleotides in length) of the molecule allows the cost of treatment to be reduced.

By "nucleic acid catalyst" as used herein is meant a nucleic acid molecule (e.g., the molecules of formulae I and II), capable of catalyzing (altering the velocity and/or rate of) a variety of reactions including the ability to repeatedly cleave other separate nucleic acid molecules (endonuclease activity) in a nucleotide base sequence-specific manner. Such a molecule with endonuclease activity may have complementarity in a substrate binding region (e.g. X and Y in formulae I and II) to a specified gene target, and also has an enzymatic activity that specifically cleaves RNA or DNA in that target. That is, the nucleic acid molecule with endonuclease activity is able to intramolecularly or intermolecularly cleave RNA or DNA and thereby inactivate a target RNA or DNA molecule. This complementarity functions to allow sufficient hybridization of the enzymatic RNA molecule to the target RNA or DNA to allow the cleavage to occur. 100% complementarity is preferred, but complementarity as low as 50–75% may also be useful in this invention. The nucleic acids may be modified at the base, sugar, and/or phosphate groups. The term enzymatic nucleic acid is used interchangeably with phrases such as ribozymes, catalytic RNA, enzymatic RNA, catalytic DNA, nucleozyme, RNA enzyme, endoribonuclease, endonuclease, minizyme, oligozyme, finderon or nucleic acid catalyst. All of these terminologies describe nucleic acid molecules with enzymatic activity. The specific examples of enzymatic nucleic acid molecules described in the instant application are not limiting in the invention and those skilled in the art will recognize that all that is important in an enzymatic nucleic acid molecule of this invention is that it has a specific substrate binding site which is complementary to one or more of the target nucleic acid regions, and that it have nucleotide sequences within or surrounding that substrate binding site which impart a nucleic acid cleaving activity to the molecule.

By "nucleic acid molecule" as used herein is meant a molecule having nucleotides. The nucleic acid can be single, double, or multiple stranded and may comprise modified or unmodified nucleotides or non-nucleotides or various mixtures and combinations thereof.

In preferred embodiments of the present invention, a nucleic acid molecule, e.g., an enzymatic nucleic acid molecule, is 13 to 100 nucleotides in length, e.g., in specific embodiments 35, 36, 37, or 38 nucleotides in length (e.g., for particular ribozymes). In particular embodiments, the nucleic acid molecule is 15–100, 17–100, 20–100, 21–100, 23–100, 25–100, 27–100, 30–100, 32–100, 35–100, 40–100, 50–100, 60–100, 70–100, or 80–100 nucleotides in length. Instead of 100 nucleotides being the upper limit on the length ranges specified above, the upper limit of the length range can be, for example, 30, 40, 50, 60, 70, or 80 nucleotides. Thus, for any of the length ranges, the length range for particular embodiments has lower limit as specified, with an upper limit as specified which is greater than the lower limit. For example, in a particular embodiment, the length range can be 35–50 nucleotides in length. All such ranges are expressly included. Also in particular embodiments, a nucleic acid molecule can have a length which is any of the lengths specified above, for example, 21 nucleotides in length.

By "complementarity" is meant that a nucleic acid can form hydrogen bond(s) with another RNA sequence by either traditional Watson-Crick or other non-traditional types. In reference to the nucleic molecules of the present invention, the binding free energy for a nucleic acid molecule with its target or complementary sequence is sufficient to allow the relevant function of the nucleic acid to proceed, e.g., enzymatic nucleic acid cleavage, antisense or triple helix inhibition. Determination of binding free energies for nucleic acid molecules is well-known in the art (see, e.g., Turner et al., 1987, *CSH Symp. Quant. Biol. LII* pp.123–133; Frier et al., 1986, *Proc. Nat. Acad. Sci. USA* 83:9373–9377; Turner et al., 1987, *J. Am. Chem. Soc.* 109:3783–3785. A percent complementarity indicates the percentage of contiguous residues in a nucleic acid molecule which can form hydrogen bonds (e.g., Watson-Crick base pairing) with a second nucleic acid sequence (e.g., 5, 6, 7, 8, 9, 10 out of 10 being 50%, 60%, 70%, 80%, 90%, and 100% complementary). "Perfectly complementary" means that all the contiguous residues of a nucleic acid sequence will hydrogen bond with the same number of contiguous residues in a second nucleic acid sequence.

The enzymatic nucleic acid molecules of Formulae I and II may independently comprise a cap structure which may independently be present or absent.

By "sufficient length" is meant an oligonucleotide of greater than or equal to 3 nucleotides. For example, for the X and Y portions of the nucleic acid molecules disclosed in formulae I and II, "sufficient length" means that the nucleotide length is long enough to provide stable binding to a target site under the expected binding conditions. Preferably, the X and Y protions are not so long as to prevent useful turnover.

By "stably interact" is meant, interaction of the oligonucleotides with target nucleic acid (e.g., by forming hydrogen bonds with complementary nucleotides in the target under physiological conditions).

By "chimeric nucleic acid molecule" or "mixed polymer" is meant that, the molecule may be comprised of both modified or unmodified nucleotides.

By "cap structure" is meant chemical modifications, which have been incorporated either terminus of the oligonucleotide. These terminal modifications protect the nucleic acid molecule from exonuclease degradation, and may help in delivery and/or localization within a cell. The cap may be present at the 5'-terminus (5'-cap) or at the 3'-terminus (3'-cap) or may be present on both termini. In non-limiting examples: the 5'-cap is selected from the group comprising inverted abasic residue (moiety), 4',5'-methylene nucleotide; 1-(beta-D-erythrofuranosyl) nucleotide, 4'-thio nucleotide, carbocyclic nucleotide; 1,5-anhydrohexitol nucleotide; L-nucleotides; alpha-nucleotides; modified base nucleotide; phosphorodithioate linkage; threo-pentofuranosyl nucleotide; acyclic 3',4'-seco nucleotide; acyclic 3,4-dihydroxybutyl nucleotide; acyclic 3,5-dihydroxypentyl nucleotide, 3'-3'-inverted nucleotide moiety; 3'-3'-inverted abasic moiety; 3'-2'-inverted nucleotide moiety; 3'-2'-inverted abasic moiety; 1,4-butanediol phosphate; 3'-phosphoramidate; hexylphosphate; aminohexyl phosphate; 3-phosphate; 3'-phosphorothioate; phosphorodithioate; or bridging or non-bridging methylphosphonate moiety (for more details see Beigelman et al., International PCT publication No. WO 97/26270, incorporated by reference herein).

In yet another preferred embodiment, the 3'-cap is selected from a group comprising, 4',5'-methylene nucleotide; 1-(beta-D-erythrofuranosyl) nucleotide; 4'-thio nucleotide, carbocyclic nucleotide; 5'-amino-alkyl phosphate; 1,3-diamino-2-propyl phosphate, 3-aminopropyl phosphate; 6-aminohexyl phosphate; 1,2-aminododecyl phosphate; hydroxypropyl phosphate; 1,5-anhydrohexitol nucleotide; L-nucleotide; alpha-nucleotide; modified base nucleotide; phosphorodithioate; threo-pentofuranosyl nucleotide; acyclic 3',4'-seco nucleotide; 3,4-dihydroxybutyl nucleotide; 3,5-dihydroxypentyl nucleotide, 5'-5'-inverted nucleotide moiety; 5'-5'-inverted abasic moiety; 5'-phosphoramidate; 5'-phosphorothioate; 1,4-butanediol phosphate; 5'-amino; bridging and/or non-bridging 5'-phosphoramidate, phosphorothioate and/or phosphorodithioate, bridging or non bridging methylphosphonate and 5'-mercapto moieties (for more details see Beaucage and Iyer, 1993, *Tetrahedron* 49, 1925; incorporated by reference herein).

By "oligonucleotide" as used herein, is meant a molecule comprising two or more nucleotides.

The specific enzymatic nucleic acid molecules described in the instant application are not limiting in the invention and those skilled in the art will recognize that all that is important in an enzymatic nucleic acid molecule of this invention is that it has a specific substrate binding site (e.g., X and Y of Formulae I and II above) which is complementary to one or more of the target nucleic acid regions, and that it have nucleotide sequences within or surrounding that substrate binding site which impart a nucleic acid cleaving activity to the molecule.

By "enzymatic portion" is meant that part of the ribozyme essential for cleavage of an RNA substrate.

Figure 5:
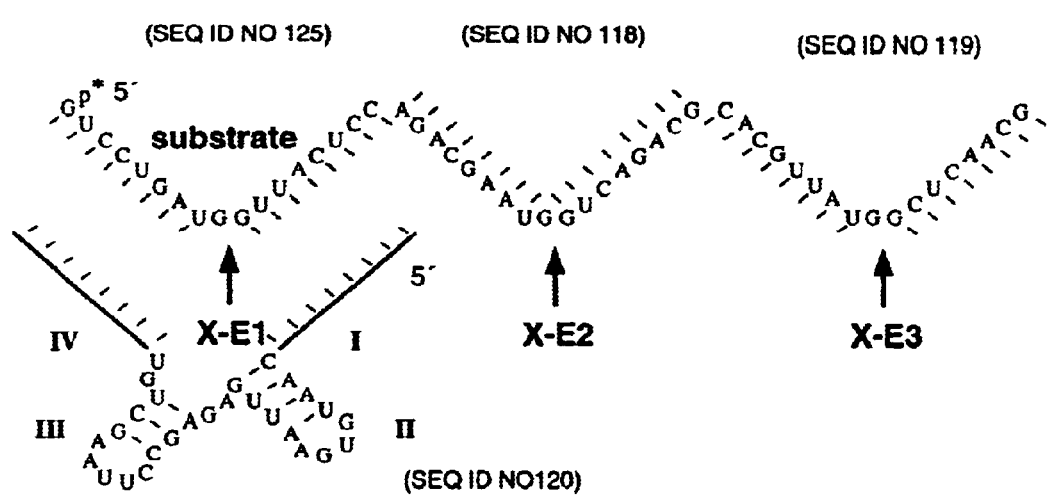

By "substrate binding arm" or "substrate binding domain" is meant that portion of a ribozyme which is complementary to (i.e., able to base-pair with) a portion of its substrate. Generally, such complementarity is 100%, but can be less if desired. For example, as few as 10 nucleotides out of a total of 14 may be base-paired. Such arms are shown generally in FIGS. 2 and 5 and as X and Y in Formulae I and II. That is, these arms contain sequences within a ribozyme which are intended to bring ribozyme and target RNA together through complementary base-pairing interactions. The ribozyme of the invention may have binding arms that are contiguous or non-contiguous and may be of varying lengths. The length of the binding arm(s) are preferably greater than or equal to four nucleotides; specifically 12–100 nucleotides; more specifically 14–24 nucleotides long. The two binding arms are chosen, such that the length of the binding arms are symmetrical (i.e., each of the binding arms is of the same length; e.g., five and five nucleotides, six and six nucleotides or seven and seven nucleotides long) or asymmetrical (i.e., the binding arms are of different length; e.g., six and three nucleotides; three and six nucleotides long; four and five nucleotides long; four and six nucleotides long; four and seven nucleotides long; and the like).

Catalytic activity of the ribozymes described in the instant invention can be optimized as described by Draper et al., supra. The details will not be repeated here, but include altering the length of the ribozyme binding arms, or chemically synthesizing ribozymes with modifications (base, sugar and/or phosphate) that prevent their degradation by serum ribonucleases and/or enhance their enzymatic activity (see e.g., Eckstein et al., International Publication No. WO 92/07065; Perrault et al., 1990 *Nature* 344, 565; Pieken et al., 1991 *Science* 253, 314; Usman and Cedergren, 1992 *Trends in Biochem. Sci.* 17, 334; Usman et al., International Publication No. WO 93/15187; and Rossi et al., International Publication No. WO 91/03162; Sproat, U.S. Pat. No. 5,334,711; and Burgin et al., supra; all of these describe various chemical modifications that can be made to the base, phosphate and/or sugar moieties of enzymatic RNA molecules). Modifications which enhance their efficacy in cells, and removal of bases from stem loop structures to shorten RNA synthesis times and reduce chemical requirements are desired. All these publications are hereby incorporated by reference herein.

Therapeutic ribozymes must remain stable within cells until translation of the target RNA has been inhibited long enough to reduce the levels of the undesirable protein. This period of time varies between hours to days depending upon the disease state. Clearly, ribozymes must be resistant to nucleases in order to function as effective intracellular therapeutic agents. Improvements in the chemical synthesis of RNA (Wincott et al., 1995 *Nucleic Acids Res.* 23, 2677; incorporated by reference herein) have expanded the ability to modify ribozymes to enhance their nuclease stability. The term "nucleotide" is used as recognized in the art to include natural bases, and modified bases well known in the art. Such bases are generally located at the 1' position of a sugar moiety. Nucleotides generally comprise a base, sugar and a phosphate group. The nucleotides can be unmodified or modified at the sugar, phosphate and/or base moiety, (see for example, Usman and McSwiggen, supra; Eckstein et al., International PCT Publication No. WO 92/07065; Usman et al., International PCT Publication No. WO 93/15187; all hereby incorporated by reference herein). There are several examples of modified nucleic acid bases known in the art; and these have recently been summarized by Limbach et al., 1994, *Nucleic Acids Res.* 22, 2183. Some of the non-limiting examples of base modifications that can be introduced into enzymatic nucleic acids without significantly effecting their catalytic activity include, inosine, purine, pyridin-4-one, pyridin-2-one, phenyl, pseudouracil, 2,4,6-trimethoxy benzene, 3-methyluracil, dihydrouridine, naphthyl, aminophenyl, 5-alkylcytidines (e.g., 5-methylcytidine), 5-alkyluridines (e.g., ribothymidine), 5-halouridine (e.g., 5-bromouridine) or 6-azapyrimidines or 6-alkylpyrimidines (e.g. 6-methyluridine) and others (Burgin et al., 1996, *Biochemistry*, 35, 14090). By "modified bases" in this aspect is meant nucleotide bases other than adenine, guanine, cytosine and uracil at 1' position or their equivalents; such bases may be used within the catalytic core of the enzyme and/or in the substrate-binding regions.

In a preferred embodiment, the invention features modified ribozymes with phosphate backbone modifications comprising one or more phosphorothioate, phosphorodithioate, methylphosphonate, morpholino, amidate carbamate, carboxymethyl, acetamidate, polyamide, sulfonate, sulfonamide, sulfamate, formacetal, thioformacetal, and/or alkylsilyl, substitutions. For a review of oligonucleotide backbone modifications see Hunziker and Leumann, 1995, *Nucleic Acid Analogues: Synthesis and Properties*, in *Modern Synthetic Methods*, VCH, 331–417, and Mesmaeker et al., 1994, *Novel Backbone Replacements for Oligonucleotides*, in *Carbohydrate Modifications in Antisense Research*, ACS, 24–39.

In a further preferred embodiment of the instant invention, an inverted deoxy abasic moiety is utilized at the 3' end of the enzymatic nucleic acid molecule.

In particular, the invention features modified ribozymes having a base substitution selected from pyridin-4-one, pyridin-2-one, phenyl, pseudouracil, 2, 4, 6-trimethoxy benzene, 3-methyluracil, dihydrouracil, naphthyl, 6-methyluracil and aminophenyl.

There are several examples in the art describing sugar and phosphate modifications that can be introduced into enzymatic nucleic acid molecules without significantly effecting catalysis and with significant enhancement in their nuclease stability and efficacy. Ribozymes are modified to enhance stability and/or enhance catalytic activity by modification with nuclease resistant groups, for example, 2'-amino, 2'-C-allyl, 2'-flouro, 2'-O-methyl, 2'-H, nucleotide base modifications (for a review see Usman and Cedergren, 1992 *TIBS* 17, 34; Usman et al., 1994 *Nucleic Acids Symp. Ser.* 31, 163; Burgin et al., 1996 *Biochemistry* 35, 14090). Sugar modifications of enzymatic nucleic acid molecules have been extensively described in the art (see Eckstein et al., *International Publication* PCT No. WO 92/07065; Perrault et al. *Nature* 1990, 344, 565–568; Pieken et al. *Science* 1991, 253, 314–317; Usman and Cedergren, *Trends in Biochem. Sci.* 1992, 17, 334–339; Usman et al. *International Publication* PCT No. WO 30 93/15187; Sproat, U.S. Pat. No. 5,334,711 and Beigelman et al., 1995 *J. Biol. Chem.* 270, 25702).

Such publications describe general methods and strategies to determine the location of incorporation of sugar, base and/or phosphate modifications and the like into ribozymes without inhibiting catalysis, and are incorporated by reference herein. In view of such teachings, similar modifications can be used as described herein to modify the nucleic acid catalysts of the instant invention.

As the term is used in this application, non-nucleotide-containing enzymatic nucleic acid means a nucleic acid molecule that contains at least one non-nucleotide component which replaces a portion of a ribozyme, e.g., but not limited to, a double-stranded stem, a single-stranded "catalytic core" sequence, a single-stranded loop or a single-stranded recognition sequence. These molecules are able to cleave (preferably, repeatedly cleave) separate RNA or DNA molecules in a nucleotide base sequence specific manner. Such molecules can also act to cleave intramolecularly if that is desired. Such enzymatic molecules can be targeted to virtually any RNA transcript.

The sequences of ribozymes that are chemically synthesized, useful in this invention, are shown in the Tables and Figures. Those in the art will recognize that these sequences are representative only of many more such sequences where the enzymatic portion of the enzymatic nucleic acid molecule (all but the binding arms) is altered to affect activity. The ribozyme sequences listed in the tables and figures may be formed of ribonucleotides or other nucleotides or non-nucleotides. Such ribozymes with enzymatic activity are equivalent to the ribozymes described specifically in the tables and figures.

Synthesis of Nucleic Acid Molecules

Synthesis of nucleic acids greater than 100 nucleotides in length can be difficult using automated methods, and the therapeutic cost of such molecules can be prohibitive. In this invention, small nucleic acid motifs ("small" refers to nucleic acid motifs no more than 100 nucleotides in length, preferably no more than 80 nucleotides in length, and most preferably no more than 50 nucleotides in length; e.g., antisense oligonucleotides, hammerhead or the Inozyme enzymatic nucleic acids) are preferably used for exogenous delivery. The simple structure of these molecules increases the ability of the nucleic acid to invade targeted regions of RNA structure. Exemplary molecules of the instant invention are chemically synthesized, and others can similarly be synthesized.

The nucleic acid molecules of the invention, including certain enzymatic nucleic acid molecules, can be synthesized using the methods described in Usman et al., 1987, J. Am. Chem. Soc., 109, 7845; Scaringe et al., 1990, Nucleic Acids Res., 18, 5433; and Wincott et al., 1995, Nucleic Acids Res. 23, 2677–2684 Wincott et al., 1997, Methods Mol. Bio., 74, 59. Such methods make use of common nucleic acid protecting and coupling groups, such as dimethoxytrityl at the 5'-end, and phosphoramidites at the 3'-end. In a non-limiting example, small scale syntheses are conducted on a 394 Applied Biosystems, Inc. synthesizer using a 0.2 μmol scale protocol with a 7.5 min coupling step for alkylsilyl protected nucleotides and a 2.5 min coupling step for 2'-O-methylated nucleotides. Table I outlines the amounts and the contact times of the reagents used in the synthesis cycle. Alternatively, syntheses at the 0.2 μmol scale can be done on a 96-well plate synthesizer, such as the PG2100 instrument produced by Protogene (Palo Alto, Calif.) with minimal modification to the cycle. A 33-fold excess (60 μL of 0.11 M=6.6 μmol) of 2'-O-methyl phosphoramidite and a 75-fold excess of S-ethyl tetrazole (60 μL of 0.25 M=15 μmol) can be used in each coupling cycle of 2'-O-methyl residues relative to polymer-bound 5'-hydroxyl. A 66-fold excess (120 μL of 0.11 M=13.2 μmol) of alkylsilyl (ribo) protected phosphoramidite and a 150-fold excess of S-ethyl tetrazole (120 μL of 0.25 M=30 μmol) can be used in each coupling cycle of ribo residues relative to polymer-bound 5'-hydroxyl. Average coupling yields on the 394 Applied Biosystems, Inc. synthesizer, determined by colorimetric quantitation of the trityl fractions, are typically 97.5–99%. Other oligonucleotide synthesis reagents for the 394 Applied Biosystems, Inc. synthesizer include; detritylation solution is 3% TCA in methylene chloride (ABI); capping is performed with 16% N-methyl imidazole in THF (ABI) and 10% acetic anhydride/10% 2,6-lutidine in THF (ABI); oxidation solution is 16.9 mM 12, 49 mM pyridine, 9% water in THF (PERSEPTIVE™). Burdick & Jackson Synthesis Grade acetonitrile is used directly from the reagent bottle. S-Ethyltetrazole solution (0.25 M in acetonitrile) is made up from the solid obtained from American International Chemical, Inc. Alternately, for the introduction of phosphorothioate linkages, Beaucage reagent (3H-1,2-Benzodithiol-3-one 1,1-dioxide 0.05 M in acetonitrile) is used.

Cleavage from the solid support and deprotection of the oligonucleotide is typically performed using either a two-pot or one-pot protocol. For the two-pot protocol, the polymer-bound trityl-on oligoribonucleotide is transferred to a 4 mL glass screw top vial and suspended in a solution of 40% aq. methylamine (1 mL) at 65° C. for 10 min. After cooling to −20° C., the supernatant is removed from the polymer support. The support is washed three times with 1.0 mL of EtOH:MeCN:H2O/3:1:1, vortexed and the supernatant is then added to the first supernatant. The combined supernatants, containing the oligoribonucleotide, are dried to a white powder. The base deprotected oligoribonucleotide is resuspended in anhydrous TEA/HF/NMP solution (300 μL of a solution of 1.5 mL N-methylpyrrolidinone, 750 μL TEA and 1 mL TEA.3HF to provide a 1.4 M HF concentration) and heated to 65° C. After 1.5 h, the oligomer is quenched with 1.5 M NH4HCO3.

Alternatively, for the one-pot protocol, the polymer-bound trityl-on oligoribonucleotide is transferred to a 4 mL glass screw top vial and suspended in a solution of 33% ethanolic methylamine/DMSO: 1/1 (0.8 mL) at 65° C. for 15 min. The vial is brought to r.t. TEA.3HF (0.1 mL) is added and the vial is heated at 65° C. for 15 min. The sample is cooled at −20° C. and then quenched with 1.5 M NH4HCO3. An alternative deprotection cocktail for use in the one pot protocol comprises the use of aqueous methylamine (0.5 ml) at 65° C. for 15 min followed by DMSO (0.8 ml) and TEA.3HF (0.3 ml) at 65° C. for 15 min. A similar methodology can be employed with 96-well plate synthesis formats by using a Robbins Scientific Flex Chem block, in which the reagents are added for cleavage and deprotection of the oligonucleotide.

For anion exchange desalting of the deprotected oligomer, the TEAB solution is loaded onto a Qiagen 500® anion exchange cartridge (Qiagen Inc.) that is prewashed with 50 mM TEAB (10 mL). After washing the loaded cartridge with 50 mM TEAB (10 mL), the RNA is eluted with 2 M TEAB (10 mL) and dried down to a white powder.

For purification of the trityl-on oligomers, the quenched NH4HCO3 solution is loaded onto a C-18 containing cartridge that had been prewashed with acetonitrile followed by 50 mM TEAA. After washing the loaded cartridge with water, the RNA is detrytylated with 0.5% TFA for 13 min. The cartridge is then washed again with water, salt exchanged with 1 M NaCl and washed with water again. The oligonucleotide is then eluted with 30% acetonitrile. Alternatively, for oligonucleotides synthesized in a 96-well format, the crude trityl-on oligonucleotide is purified using a 96-well solid phase extraction block packed with C18 material, on a Bohdan Automation workstation.

The average stepwise coupling yields are typically >98% (Wincott et al., 1995 Nucleic Acids Res. 23, 2677–2684). Those of ordinary skill in the art will recognize that the scale of synthesis can be adapted as larger or smaller than the example described above including but not limited to 96 well format, all that is important is the ratio of chemicals used in the reaction.

To ensure the quality of synthesis of nucleic acid molecules of the invention, quality control measures are utilized for the analysis of nucleic acid material. Capillary Gel Electrophoresis, for example using a Beckman MDQ CGE instrument, can be ulitized for rapid analysis of nucleic acid molecules, by introducing sample on the short end of the capillary. In addition, mass spectrometry, for example using a PE Biosystems Voyager-DE MALDI instrument, in combination with the Bohdan workstation, can be utilized in the analysis of oligonucleotides, including oligonucleotides synthesized in the 96-well format.

Enzymatic nucleic acids can also be synthesized in two parts and annealed to reconstruct the active enzymatic nucleic acid (Chowrira and Burke, 1992 Nucleic Acids Res., 20, 2835–2840). Enzymatic nucleic acids are also synthesized from DNA templates using bacteriophage T7 RNA polymerase (Milligan and Uhlenbeck, 1989, Methods Enzymol. 180, 51).

Alternatively, the nucleic acid molecules of the present invention can be synthesized separately and joined together post-synthetically, for example by ligation (Moore et al., 1992, Science 256, 9923; Draper et al., International PCT publication No. WO 93/23569; Shabarova et al., 1991, Nucleic Acids Research 19, 4247; Bellon et al., 1997, Nucleosides & Nucleotides, 16, 951; Bellon et al., 1997, Bioconjugate Chem. 8, 204).

The nucleic acid molecules of the present invention are preferably modified to enhance stability by modification with nuclease resistant groups, for example, 2'-amino, 2'-C-allyl, 2'-flouro, 2'-O-methyl, 2'-H (for a review see Usman and Cedergren, 1992, TIBS 17, 34; Usman et al., 1994, Nucleic Acids Symp. Ser. 31, 163). Enzymatic nucleic acids are purified by gel electrophoresis using known methods or are purified by high pressure liquid chromatography (HPLC; See Wincott et al., Supra, the totality of which is hereby incorporated herein by reference) and are re-suspended in water.

Administration of Ribozymes

Sullivan et al., PCT WO 94/02595, describe the general methods for delivery of enzymatic RNA molecules. Ribozymes can be administered to cells by a variety of methods known to those familiar to the art, including, but not restricted to, encapsulation in liposomes, by iontophoresis, or by incorporation into other vehicles, such as hydrogels, cyclodextrins, biodegradable nanocapsules, and bioadhesive microspheres. For some indications, ribozymes can be directly delivered ex vivo to cells or tissues with or without the aforementioned vehicles. Alternatively, the RNA/vehicle combination is locally delivered by direct injection or by use of a catheter, infusion pump or stent. Other routes of delivery include, but are not limited to, intravascular, intramuscular, subcutaneous or joint injection, aerosol inhalation, oral (tablet or pill form), topical, systemic, ocular, intraperitoneal and/or intrathecal delivery. More detailed descriptions of ribozyme delivery and administration are provided in Sullivan et al., supra and Draper et al., PCT WO93/23569 which have been incorporated by reference herein.

The molecules of the instant invention can be used as pharmaceutical agents. Pharmaceutical agents prevent, inhibit the occurrence, or treat (alleviate a symptom to some extent, preferably all of the symptoms) of a disease state in a patient.

The negatively charged polynucleotides of the invention can be administered (e.g., RNA, DNA or protein) and introduced into a patient by any standard means, with or without stabilizers, buffers, and the like, to form a pharmaceutical composition. When it is desired to use a liposome delivery mechanism, standard protocols for formation of liposomes can be followed. The compositions of the present invention can also be formulated and used as tablets, capsules or elixirs for oral administration; suppositories for rectal administration; sterile solutions; suspensions for injectable administration; and other compositions known in the art.

The present invention also includes pharmaceutically acceptable formulations of the compounds described. These formulations include salts of the above compounds, e.g., acid addition salts, including salts of hydrochloric, hydrobromic, acetic acid, and benzene sulfonic acid.

A pharmacological composition or formulation refers to a composition or formulation in a form suitable for administration, e.g., systemic administration, into a cell or patient, preferably a human. Suitable forms, in part, depend upon the use or the route of entry, for example, oral, transdermal, or by injection. Such forms should not prevent the composition or formulation from reaching a target cell (i.e., a cell to which the negatively charged polymer is desired to be delivered to). For example, pharmacological compositions injected into the blood stream should be soluble. Other factors are known in the art, and include considerations such as toxicity and forms which prevent the composition or formulation from exerting its effect.

By "systemic administration" is meant in vivo systemic absorption or accumulation of drugs in the blood stream followed by distribution throughout the entire body. Administration routes which lead to systemic absorption include, without limitations: intravenous, subcutaneous, intraperitoneal, inhalation, oral, intrapulmonary and intramuscular. Each of these administration routes expose the desired negatively charged polymers, e.g., nucleic acids, to an accessible diseased tissue. The rate of entry of a drug into the circulation has been shown to be a function of molecular weight or size. The use of a liposome or other drug carrier comprising the compounds of the instant invention can potentially localize the drug, for example, in certain tissue types, such as the tissues of the reticular endothelial system (RES). A liposome formulation which can facilitate the association of drug with the surface of cells, such as, lymphocytes and macrophages is also useful. This approach can provide enhanced delivery of the drug to target cells by taking advantage of the specificity of macrophage and lymphocyte immune recognition of abnormal cells, such as the cancer cells.

The invention also features the use of a composition comprising surface-modified liposomes containing poly (ethylene glycol) lipids (PEG-modified, or long-circulating liposomes or stealth liposomes). These formulations offer a method for increasing the accumulation of drugs in target tissues. This class of drug carriers resists opsonization and elimination by the mononuclear phagocytic system (MPS or RES), thereby enabling longer blood circulation times and enhanced tissue exposure for the encapsulated drug (Lasic et al. *Chem. Rev.* 1995, 95, 2601–2627; Ishiwata et al., *Chem. Pharm. Bull.* 1995, 43, 1005–1011). Such liposomes have been shown to accumulate selectively in tumors, presumably by extravasation and capture in the neovascularized target tissues (Lasic et al., *Science* 1995, 267, 1275–1276; Oku et al., 1995, *Biochim. Biophys. Acta*, 1238, 86–90). The long-circulating liposomes enhance the pharmacokinetics and pharmacodynamics of DNA and RNA, particularly compared to conventional cationic liposomes which are known to accumulate in tissues of the MPS (Liu et al., *J. Biol. Chem.* 1995, 42, 24864–24870; Choi et al., International PCT Publication No. WO 96/10391; Ansell et al., International PCT Publication No. WO 96/10390; Holland et al., International PCT Publication No. WO 96/10392; all of which are incorporated by reference herein). Long-circulating liposomes are also likely to protect drugs from nuclease degradation to a greater extent compared to cationic liposomes, based on their ability to avoid accumulation in metabolically aggressive MPS tissues such as the liver and spleen. All of these references are incorporated by reference herein.

The present invention also includes compositions prepared for storage or administration which include a pharmaceutically effective amount of the desired compounds in a pharmaceutically acceptable carrier or diluent. Acceptable carriers or diluents for therapeutic use are well known in the pharmaceutical art, and are described, for example, in *Remington's Pharmaceutical Sciences*, Mack Publishing Co. (A. R. Gennaro edit. 1985) hereby incorporated by reference herein. For example, preservatives, stabilizers, dyes and flavoring agents may be provided. Id. at 1449. These include sodium benzoate, sorbic acid and esters of p-hydroxybenzoic acid. In addition, antioxidants and suspending agents can be used.

A pharmaceutically effective dose is that dose required to prevent, inhibit the occurrence, or treat (alleviate a symptom to some extent, preferably all of the symptoms) of a disease state. The pharmaceutically effective dose depends on the type of disease, the composition used, the route of administration, the type of mammal being treated, the physical characteristics of the specific mammal under consideration, concurrent medication, and other factors which those skilled in the medical arts will recognize. Generally, an amount between 0.1 mg/kg and 100 mg/kg body weight/day of active ingredients is administered dependent upon potency of the negatively charged polymer. In a one aspect, the invention provides enzymatic nucleic acid molecules that can be delivered exogenously to specific cells as required. The enzymatic nucleic acid molecules are added directly, or can be complexed with cationic lipids, packaged within liposomes, or otherwise delivered to smooth muscle cells. The RNA or RNA complexes can be locally administered to relevant tissues through the use of a catheter, infusion pump or stent, with or without their incorporation in biopolymers. Using the methods described herein, other enzymatic nucleic acid molecules that cleave target nucleic acid may be derived and used as described above. Specific examples of nucleic acid catalysts of the instant invention are provided below in the Tables and figures.

Alternatively, the enzymatic nucleic acid molecules of the instant invention can be expressed within cells from transcription promoters (e.g., Izant and Weintraub, 1985 *Science* 229, 345; McGarry and Lindquist, 1986 *Proc. Natl. Acad. Sci. USA* 83, 399; Scanlon et al., 1991, *Proc. Natl. Acad. Sci. USA*, 88, 10591–5; Kashani-Sabet et al., 1992 *Antisense Res. Dev.*, 2, 3–15; Dropulic et al., 1992 *J. Virol*, 66, 1432–41; Weerasinghe et al., 1991 *J. Virol*, 65, 5531–4; Ojwang et al., 1992 *Proc. Natl. Acad. Sci. USA* 89, 10802–6; Chen et al., 1992 *Nucleic Acids Res.*, 20, 4581–9; Sarver et al., 1990 *Science* 247, 1222–1225; Thompson et al., 1995 *Nucleic Acids Res.* 23, 2259; Good et al., 1997, *Gene Therapy*, 4, 45; all of these references are hereby incorporated in their totalities by reference herein). Those skilled in the art realize that any nucleic acid can be expressed in eukaryotic cells from the appropriate DNA/RNA vector. The activity of such nucleic acids can be augmented by their release from the primary transcript by a ribozyme (Draper et al., PCT WO 93/23569, and Sullivan et al., PCT WO 94/02595; Ohkawa et al., 1992 *Nucleic Acids Symp. Ser.*, 27, 15–6; Taira et al., 1991, *Nucleic Acids Res.*, 19, 5125–30; Ventura et al., 1993 *Nucleic Acids Res.*, 21, 3249–55; Chowrira et al., 1994 *J. Biol. Chem.* 269, 25856; all of these references are hereby incorporated by reference herein in their totalities).

In another aspect of the invention, enzymatic nucleic acid molecules that cleave target molecules are expressed from transcription units (see for example Couture et al., 1996, *TIG.*, 12, 510) inserted into DNA or RNA vectors. The recombinant vectors are preferably DNA plasmids or viral vectors. Ribozyme expressing viral vectors can be constructed based on, but not limited to, adeno-associated virus, retrovirus, adenovirus, or alphavirus or baculovirus. Preferably, the recombinant vectors capable of expressing the ribozymes are delivered as described above, and persist in target cells. Alternatively, viral vectors can be used that provide for transient expression of ribozymes. Such vectors might be repeatedly administered as necessary. Once expressed, the ribozymes cleave the target mRNA. The active ribozyme contains an enzymatic center or core equivalent to those in the examples, and binding arms able to bind target nucleic acid molecules such that cleavage at the target site occurs. Other sequences can be present which do not interfere with such cleavage. Delivery of ribozyme expressing vectors could be systemic, such as by intravenous or intramuscular administration, by administration to target cells ex-planted from the patient followed by reintroduction into the patient, or by any other means that would allow for introduction into the desired target cell (for a review see Couture et al., 1996, *TIG.*, 12, 510).

In one aspect the invention features, an expression vector comprising a nucleic acid sequence encoding at least one of the nucleic acid catalysts of the instant invention. The nucleic acid sequence encoding the nucleic acid catalyst of the instant invention is operably linked in a manner which allows expression of that nucleic acid molecule.

In another aspect the invention features, an expression vector comprising: a) a transcription initiation region (e.g., eukaryotic pol I, II or III initiation region); b) a transcription termination region (e.g., eukaryotic pol I, II or III termination region); c) a nucleic acid sequence encoding at least one of the nucleic acid catalyst of the instant invention; and wherein said sequence is operably linked to said initiation region and said termination region, in a manner which allows expression and/or delivery of said nucleic acid molecule. The vector can optionally include an open reading frame (ORF) for a protein operably linked on the 5' side or the 3'-side of the sequence encoding the nucleic acid catalyst of the invention; and/or an intron (intervening sequences).

Transcription of the ribozyme sequences are driven from a promoter for eukaryotic RNA polymerase I (pol I), RNA polymerase II (pol II), or RNA polymerase III (pol III). Transcripts from pol II or pol III promoters are expressed at high levels in all cells; the levels of a given pol II promoter in a given cell type depends on the nature of the gene regulatory sequences (enhancers, silencers, etc.) present nearby. Prokaryotic RNA polymerase promoters are also used, providing that the prokaryotic RNA polymerase enzyme is expressed in the appropriate cells (Elroy-Stein and Moss, 1990 *Proc. Natl. Acad. Sci. USA*, 87, 6743–7; Gao and Huang 1993 *Nucleic Acids Res.*, 21, 2867–72; Lieber et al., 1993 *Methods Enzymol.*, 217, 47–66; Zhou et al., 1990 *Mol. Cell. Biol.*, 10, 4529–37). All of these references are incorporated by reference herein. Several investigators have demonstrated that ribozymes expressed from such promoters can function in mammalian cells (e.g. Kashani-Sabet et al., 1992 *Antisense Res. Dev.*, 2, 3–15; Ojwang et al., 1992 *Proc. Natl. Acad. Sci. USA*, 89, 10802–6; Chen et al, 1992 *Nucleic Acids Res.*, 20, 4581–9; Yu et al., 1993 *Proc. Natl. Acad. Sci. USA*, 90, 6340–4; L'Huillier et al., 1992 *EMBO J*. 11, 4411–8; Lisziewicz et al., 1993 *Proc. Natl. Acad. Sci. U.S.A.*, 90, 8000–4; Thompson et al., 1995 *Nucleic Acids Res*. 23, 2259; Sullenger & Cech, 1993, *Science*, 262, 1566). More specifically, transcription units such as the ones derived from genes encoding U6 small nuclear (snRNA), transfer RNA (tRNA) and adenovirus VA RNA are useful in generating high concentrations of desired RNA molecules such as ribozymes in cells (Thompson et al., supra; Couture and Stinchcomb, 1996, supra; Noonberg et al., 1994, *Nucleic Acid Res*., 22, 2830; Noonberg et al., U.S. Pat. No. 5,624,803; Good et al., 1997, *Gene Ther*. 4, 45; Beigelman et al., International PCT Publication No. WO 96/18736; all of these publications are incorporated by reference herein. The above ribozyme transcription units can be incorporated into a variety of vectors for introduction into mammalian cells, including but not restricted to, plasmid DNA vectors, viral DNA vectors (such as adenovirus or adeno-associated virus vectors), or viral RNA vectors (such as retroviral or alphavirus vectors) (for a review see Couture and Stinchcomb, 1996, supra).

The invention also features a method for enhancing the effect of the nucleic acid catalyst of the instant invention in vivo. The method includes the step of causing the nucleic acid catalyst to be localized in vivo with its target. In a related aspect, the invention features nucleic acid catalysts which are adapted for localization with the viral target of the agent in vivo.

Those in the art will recognize that many methods can be used for modification of nucleic acid catalyst such that they are caused to be localized in an appropriate compartment with a target. Examples of these methods follow but are not limiting in the invention. Thus, for example, the nucleic acid catalysts of the invention can be synthesized in vivo from vectors (or formed in vitro) such that they are covalently or noncovalently bonded with a targeting agent, examples of which are well known in the art (Sullenger et al., U.S. Pat. No. 5,854,038; Castanotto et al., *Methods Enzymol* 2000;313:401–20; Rossi et al., Science 1999, 285,1685). These targeting agents are termed "localization signals". In addition, nucleic acid catalysts may be synthesized in vitro and administered in any one of many standard methods to cause the nucleic acid catalysts to be targeted to an appropriate cellular compartment within a patient.

By "enhancing" the effect of a nucleic acid catalysts in vivo is meant that a localization signal targets that nucleic acid catalysts to a specific site within a cell and thereby causes that nucleic acid catalysts to act more efficiently. Thus, a lower concentration of nucleic acid catalysts administered to a cell in vivo can have an equal effect to a larger concentration of non-localized nucleic acid catalysts. Such increased efficiency of the targeted or localized nucleic acid catalysts can be measured by any standard procedure well-known to those of ordinary skill in the art. In general, the effect of the nucleic acid catalyst is enhanced by placing the nucleic acid catalyst in a closer proximity with the target, so that it may have its desired effect on that target. This may be achieved by causing the nucleic acid catalysts to be located in a small defined compartment with the target (e.g., within a viral particle), or to be located in the same space within a compartment, e.g., in a nucleus at the location of synthesis of the target.

Localization signals include any proteinaceous or nucleic acid component which naturally becomes localized in the desired compartment, for example, a viral packaging signal, or its equivalent. Localization signals can be identified by those in the art as those signals which cause the nucleic acid catalysts to which they are associated with to become localized in certain compartments, and can be readily discovered using standard methodology. These localization signals can be tethered to the nucleic acid catalysts by any desired procedure, for example, by construction of a DNA template which produces both the localization signal and nucleic acid catalysts as part of the same molecule, or by covalent or ionic bond formation between two moieties. All that is essential in the invention is that the nucleic acid catalysts be able to have its inhibitory effect when localized in the target site, and that the localization signal be able to localize that nucleic acid catalysts to that target site. Examples of useful localization signals and cell compartments include viral genomic packaging signals, for example, for RNA virus genomes, including, retroviruses (HIV, HTLV I & II, other human retroviruses, ALV, RSV, avian sarcoma virus and other chicken retroviruses, MoMLV and other Mouse retroviruses, FeLV and other feline retroviruses, and all other retroviral genomic RNA packaging signals). Also included are all other RNA viruses packaging signals; e.g., hepatitis B virus, and all DNA virus genomic packaging signals, e.g., HSV I, and adenovirus. Other viral nucleic acid sorting signals include HIV's Rev response element, and any other nucleic acid sequence which causes viral RNA or DNA to be sorted in some unique way, e.g., retroviral frame shifting during translation.

Yet other examples include any cellular RNA localization signal which causes RNAs containing the signal to be sorted into a pathway which does not contain large numbers of incorrect targets; viral protein localization/assembly signals: e.g., Rev or gag proteins.

Increasing the concentration of a viral inhibitor at an intracellular site important for viral replication or assembly is a general way to increase the effectiveness of nucleic acid catalysts. The above-described colocalization strategy can make use of, for example, a viral packaging signal to colocalize nucleic acid catalysts with a target responsible for viral replication. In this way viral replication can be reduced or prevented. This method can be employed to enhance the effectiveness of nucleic acid catalysts by tethering them to an appropriate localization signal to sort them to the therapeutically important intracellular and viral location where the viral replication machinery is active.

Such colocalization strategies are not limited to using naturally occurring localization signals. Nucleic acid catalysts can be targeted to important intracellular locations by use of artificially evolved RNAs and/or protein decoys (Szostak, 17 TIBS 89, 1992). These evolved molecules are selected for example to bind to a viral protein and may be used to colocalize nucleic acid catalysts with a viral target by tethering the inhibitor to such a decoy.

In yet another aspect, the invention features an expression vector comprising a nucleic acid sequence encoding at least one of the catalytic nucleic acid molecules of the invention, in a manner which allows expression of that nucleic acid molecule. The expression vector comprises in one embodiment; a) a transcription initiation region; b) a transcription termination region; c) a nucleic acid sequence encoding at least one said nucleic acid molecule; and wherein said sequence is operably linked to said initiation region and said termination region, in a manner which allows expression and/or delivery of said nucleic acid molecule. In another preferred embodiment the expression vector comprises: a) a transcription initiation region; b) a transcription termination region; c) an open reading frame; d) a nucleic acid sequence encoding at least one said nucleic acid molecule, wherein said sequence is operably linked to the 3'-end of said open reading frame; and wherein said gene sequence is operably linked to said initiation region, said open reading frame and said termination region, in a manner which allows expression and/or delivery of said nucleic acid molecule. In yet another embodiment, the expression vector comprises: a) a transcription initiation region; b) a transcription termination region; c) an intron; d) a nucleic acid sequence encoding at least one said nucleic acid molecule; and wherein said sequence is operably linked to said initiation region, said intron and said termination region, in a manner which allows expression and/or delivery of said nucleic acid molecule. In another embodiment, the expression vector comprises: a) a transcription initiation region; b) a transcription termination region; c) an intron; d) an open reading frame; e) a nucleic acid sequence encoding at least one said nucleic acid molecule, wherein said sequence is operably linked to the 3'-end of said open reading frame; and wherein said sequence is operably linked to said initiation region, said intron, said open reading frame and said termination region, in a manner which allows expression and/or delivery of said nucleic acid molecule.

By "consists essentially of" is meant that the active ribozyme contains an enzymatic center or core equivalent to those in the examples, and binding arms able to bind target nucleic acid molecules such that cleavage at the target site occurs. Other sequences can be present which do not interfere with such cleavage.

The nucleic acid catalyst of the instant invention can be used to inhibit expression of foreign or endogenous genes, in vitro or in vivo, in prokaryotic cells or in eukaryotic cells, in bacteria, fungi, mycoplasma, archebacteria, algae, plants or any other biological system.

By "endogenous" gene is meant a gene normally found in a cell in its natural location in the genome.

By "foreign" or "heterologous" gene is meant a gene not normally found in the host cell, but that is introduced by standard gene transfer techniques or acquired as result of an infection (e.g., bacterial, viral or fungal infection).

By a "plant" is meant a photosynthetic organism, either eukaryotic and prokaryotic.

By "promoter" is meant a nucleotide sequence element within a gene which controls the expression of that gene. A promoter sequence provides the recognition for RNA polymerase and other transcription factors required for efficient transcription. Promoters from a variety of sources can be used efficiently in plant cells to express ribozymes. For example, promoters of bacterial origin, such as the octopine synthetase promoter, the nopaline synthase promoter, the manopine synthetase promoter; promoters of viral origin, such as the cytomegalovirus, cauliflower mosaic virus (35S); plant promoters, such as the ribulose-1,6-biphosphate (RUBP) carboxylase small subunit (ssu), the beta-conglycinin promoter, the phaseolin promoter, the ADH promoter, heat-shock promoters, and tissue specific promoters. A promoter can also contain certain enhancer sequence elements that improve the transcription efficiency.

EXAMPLES

The following are non-limiting examples showing the selection, isolation, synthesis and activity of enzymatic nucleic acids of the instant invention.

An extensive array of site-directed mutagenesis studies have been conducted with the hammerhead ribozyme to probe relationships between nucleotide sequence and catalytic activity. These systematic studies have made clear that most nucleotides in the conserved core of the hammerhead ribozyme (Forster & Symons, 1987, *Cell*, 49, 211) cannot be mutated without significant loss of catalytic activity. In contrast, a combinatorial strategy that simultaneously screens a large pool of mutagenized ribozymes for RNAs that retain catalytic activity can be used more efficiently to define immutable sequences and to identify new ribozyme variants (Breaker, 1997, supra). For example, Joseph and Burke (1993; *J. Biol. Chem.*, 268, 24515) have used an in vitro selection approach to rapidly screen for sequence variants of the 'hairpin' self-cleaving RNA that show improved catalytic activity. This approach was successful in identifying two mutations in the hairpin ribozyme that together give a 10-fold improvement in catalytic rate.

Applicant employed in vitro selection to isolate populations of $Mg^{2+}$-dependent self-cleaving ribozymes from a pool of random-sequence molecules. Characterization of a small number of individual ribozymes from various populations revealed the emergence of at least 12 classes of ribozymes that adopt distinct secondary structure motifs. Only one of the 12 classes corresponds to a previously known folding pattern—that of the natural hammerhead ribozyme. Each prototypic ribozyme promotes self-cleavage via an internal phosphoester transfer reaction involving the adjacent 2'-hydroxyl group with a chemical rate enhancement of at least 1000-fold above the corresponding uncatalyzed rate.

In vitro Selection of Self-cleaving RNAs from a Random Pool

Figure 1:
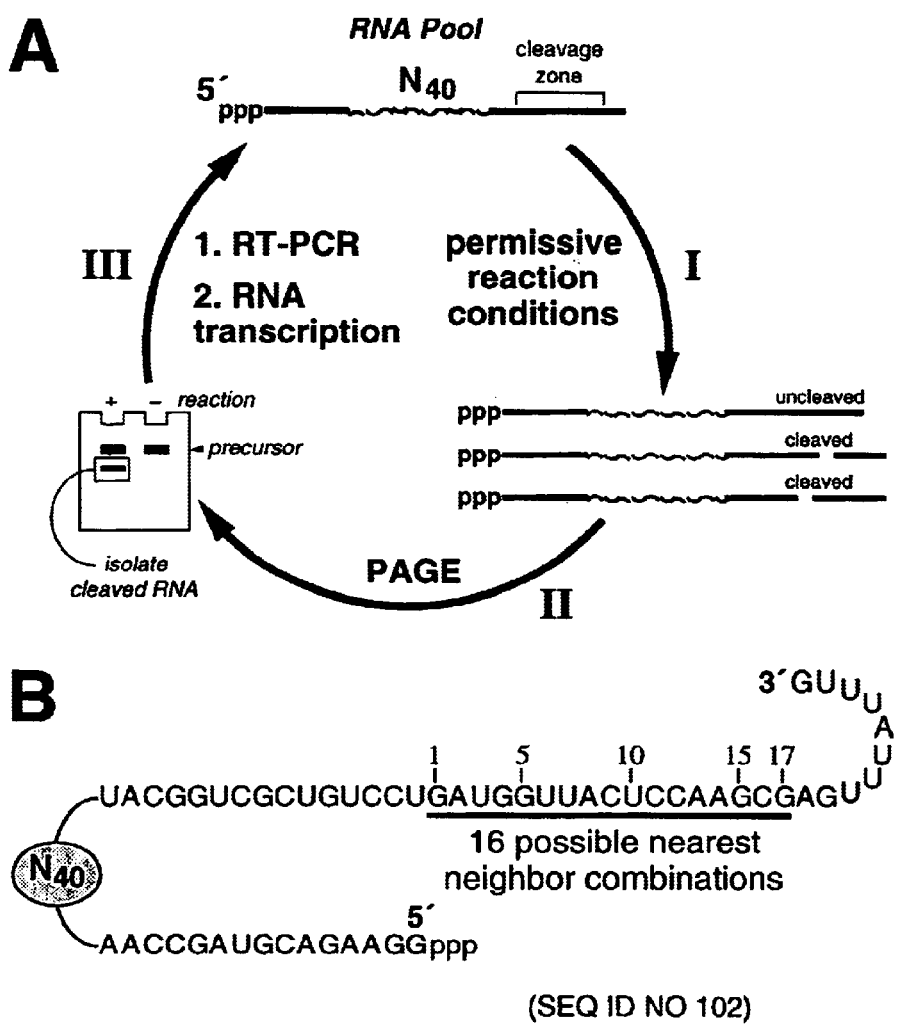

Isolation of new ribozymes from a population of ~$10^{14}$ different RNAs was performed using the selective-amplification scheme depicted in FIG. 1A. Each RNA construct used for in vitro selection includes a 40-nt random-sequence region flanked both on its 5'- and 3' sides by domains of defined nucleotide sequence (FIG. 1B). The 3'-flanking domain was designed to serve as the target site for ribozyme cleavage. Due to its extended length, the 3'-flanking domain can experience the loss of nucleotides via ribozyme action, yet still function as a primer-binding site for amplification by RT-PCR. Moreover, the nucleotide sequence of this domain was designed to represent all 16 possible nearest neighbor combinations in order to favor the isolation of ribozymes that might have necessity for a particular dinucleotide identity at their cleavage site.

In each round of selection, the RNAs were transcribed in vitro using T7 RNAP and the uncleaved RNA precursors were isolated by PAGE. The $Mg^{2+}$ concentration and the incubation time used for in vitro transcription were minimized in order to reduce the likelihood that efficient $Mg^{2+}$-dependent ribozymes would be cleaved during enzymatic synthesis and thereby lost upon isolation of the uncleaved RNA precursors. In addition, the incubation time used for crush/soak isolation of RNA precursors from polyacrylamide gel was minimized to preclude the isolation of self-cleaving ribozymes that react in the absence of $Mg^{2+}$. For selection, the purified RNA precursors were incubated under permissive reaction conditions (50 mM Tris-HCl [pH 7.5 at 23° C.], 250 mM KCl, 20 mM $MgCl_2$) at 23° C. for 4 hr. RNAs that cleaved in the 3' domain during this incubation were isolated by PAGE. Specifically, the zone that contains RNA cleavage fragments that are between ~10 to ~30 nucleotides shorter than the precursor RNAs was excised and the recovered RNAs were amplified by RT-PCR.

The population of RNAs isolated after six rounds of selection (G6) exhibits a significant level of self-cleavage activity in the presence of $Mg^{2+}$. At this stage, the major 5'-cleavage products were isolated and the RT-PCR products of the isolated RNAs were cloned and sequenced. The remainder of the zone typically excised, which presumably contains 5'-cleavage fragments of different lengths, was used to continue the selective-amplification process. This isolation strategy serves two purposes. First, the ribozymes that produce the major cleavage products observed in FIG. 1C, and which presumably dominate the population at G6, can be examined in greater detail. Second, these more commonly represented sequences are largely excluded from the subsequent rounds of selection and thus are less likely to dominate the RNA population in future rounds. This allows ribozymes that are less frequently represented to increase in frequency in later populations. In a similar fashion, the main product bands representing the 5'-cleavage fragments at G9, G12 and G15 were selectively recovered from the gel and subjected to RT-PCR amplification followed by cloning and sequencing. This strategy offers an effective means by which many different self-cleaving RNA motifs can be isolated.

By "random sequence region" is meant a region of completely random sequence and/or partially random sequence. By completely random sequence is meant a sequence wherein theoretically there is equal representation of A, T, G and C nucleotides or modified derivatives thereof, at each position in the sequence. By partially random sequence is meant a sequence wherein there is an unequal representation of A, T, G and C nucleotides or modified derivatives thereof, at each position in the sequence. A partially random sequence can therefore have one or more positions of complete randomness and one or more positions with defined nucleotides.

Characterization of New Self-cleaving Ribozyme Sequences

Figure 2:
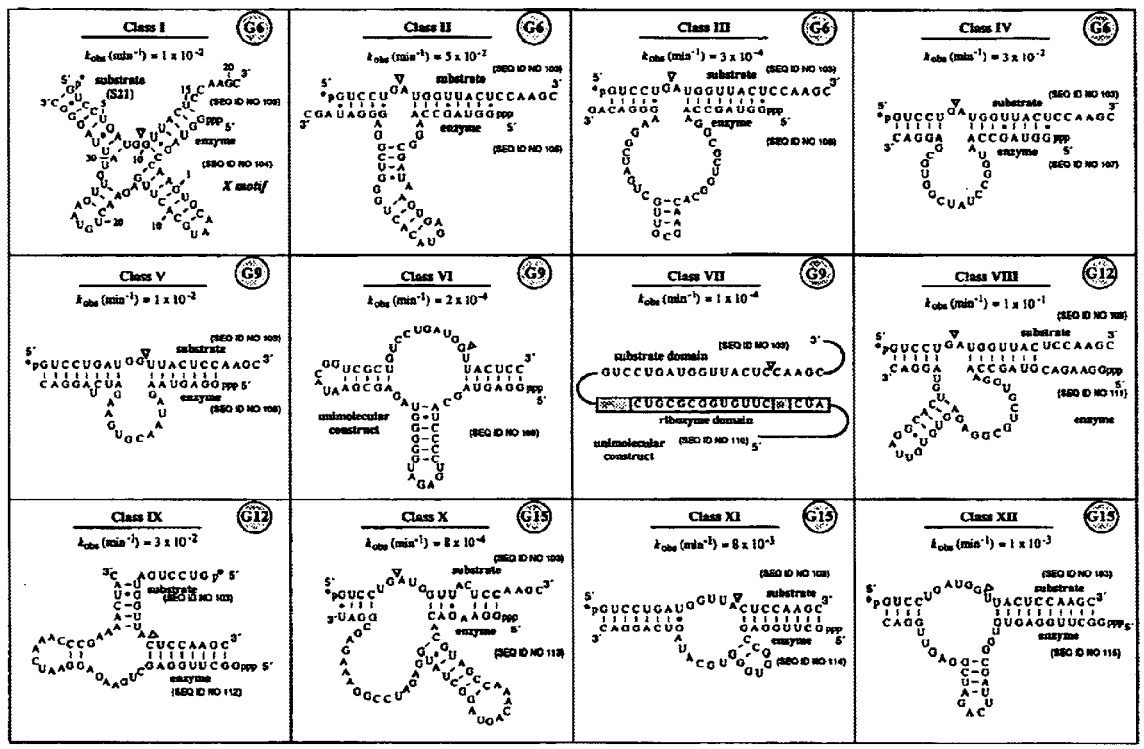

Sequence analysis of greater than 100 clones representing self-cleaving ribozymes from the G6, G9, G12 and G15 populations revealed as many as 20 distinct sequence classes of RNAs. In some cases, numerous RNAs conformed to a single class of self-cleaving ribozyme based on sequence elements that are common among the related variants. For example, ~30 clones were identified that can form a common secondary structure with similar core nucleotides that we defined as "class I" ribozymes. In other instances, RNAs were isolated that were entirely unique in sequence compared to all other clones. These "orphan" sequences were classified independently, for example, as was done with the "class II" ribozyme. Ultimately, these 20 different sequence classes were grouped into twelve distinct structural classes of self-cleaving ribozymes that were identified based on the presence of distinctive sequence elements, secondary structures and cleavage sites (FIG. 2). Only one of the twelve classes (class IX) corresponds to a naturally-occurring RNA—the self-cleaving hammerhead ribozyme. The distinctions between the different structural classes of ribozymes were established as described for class I and class II ribozymes below.

For each of the 20 putative sequence classes into which the ribozymes were originally grouped, applicant conducted three to five rounds of reselection (FIG. 1A) for self-cleavage activity beginning with a population of ribozyme variants based on the nucleotide sequence of a representative clone. As expected, the introduction of random mutations (d=0.21; see Fedor and Uhlenbeck, 1992, Biochemistry, 31, 12042–12054) into the original $N_{40}$ domain of each clone decreases the catalytic activity of the population significantly. However, after three to five rounds of reselection, the mutagenized populations recovered significant levels of self-cleavage activity. Once the catalytic activity of a particular population became near equal to that of its parent clone, representative ribozyme variants were identified by cloning and sequencing.

The nucleotide sequences corresponding to the variant ribozyme domains of cloned RNAs for each class were aligned to provide an artificial phylogeny. Table VIII shows artificial phylogenetic analysis of class I, class II, and class V ribozymes. Sequence variations are depicted for the 40 nucleotides corresponding to the original random-sequence domain of each parental sequence (numbered). Dots indicate no change from the parental sequence listed first. The asterisk identifies a class I ribozyme variant that carries mutations at positions 18 and 26 that retain the ability to base pair. For example, applicant observed that the parental sequences of both class I and class II ribozymes undergo substantial mutation without complete disruption of catalytic activity (Table VIII). However, the pattern of mutation acquisition in each case is indicative of the presence of conserved primary and secondary structures that presumably are important for ribozyme function. Among the ribozyme variants obtained for class I, all retain the prototypic nucleotide sequence at positions 12–16 (FIG. 2 and Table VIII), suggesting that these nucleotides are critical for self-cleavage activity. Nucleotides 8–14, which overlap with the conserved 12–16 nt region exhibit complementarity to nucleotides within the 3' primer-binding domain. Moreover, the nucleotides at positions 17–19 and 25–27 are both mutually complementary and highly conserved. This indicates that these latter two sequence elements also might form a hairpin structure with intervening nucleotides 20–24 serving as a connecting loop. Consistent with this interpretation is the observation that mutations within positions 17–19 and 25–27 acquired by a class I ribozyme variant (Table VIII; asterisk) allows retention of base complementarity. In addition, the putative loop sequence spanning nucleotides 20–24 tolerates significant mutation as would be expected if the nucleotides in the loop were unimportant for stem formation and ultimately for ribozyme action.

Similar characteristics of structure formation and conserved sequences are evident in the artificial phylogeny for class II ribozymes (Table VIII). However, the data indicate that class II ribozymes form a catalytic structure that is distinct from that of class I. For example, complementary segments of the original random-sequence domain also are consistent with the formation of two separate stem elements. However, if present, these stems would be arranged differently from those predicted to form in class I ribozymes. At this time only one stem, that formed between nucleotides 8–11 and 16–19, appears to be present as judged by the emergence of sequence variants in the artificial phylogeny of class II. Moreover, two conserved regions (nucleotides 1–7 and 22–30) (FIG. 2 and Table VIII) of class II RNAs are different from the conserved sequences found in class I RNAs, indicating that the two classes of ribozymes are indeed distinct.

Likewise, by analysis of the artificial phylogenetic data for the remaining 18 clones, applicant identified as many as 12 distinct classes of ribozymes (FIG. 2). In many instances, obscure sequence and structural similarities were revealed between the different sequence classes upon examination of each artificial phylogeny that was generated by reselection. Such unforeseen similarities were identified typically among representative RNAs that conform to a structural class placing very little demand on sequence conservation in the core of the ribozyme domain (e.g. classes V and VIII). It also is important to note that the structural models depicted in FIG. 2 are not intended to represent confirmed secondary structures. In most cases, limited artificial phylogenetic data coupled with preliminary analyses using a secondary-structure prediction algorithm (Zuker, 1989, *Science*, 244, 48–52) were used to derive the models.

Characterization of Bimolecular Ribozyme Reactions

Based on preliminary sequence analysis, class I self-cleaving ribozymes form an X-shaped secondary structure (FIG. 2). In this model, a separate ribozyme domain base pairs to its corresponding substrate domain with duplex formation occurring both 5' and 3' relative to an unpaired G residue that resides within the nearest neighbor sequence of the original RNA construct (position 4 of the nearest neighbor domain, FIG. 1B; position 9 of a 21-nt substrate "S21", FIG. 2). This secondary structure arrangement also locates the conserved nucleotides and the putative hairpin structures near this unpaired G residue.

Phosphodiester linkages of residues that reside outside of helical structures are most likely to be targets for ribozyme action. While stable RNA helices restrict conformational freedom of phosphodiester bonds, linkages joining unpaired nucleotides can more easily adopt the "in-line" geometry that is necessary for internal transesterification (Soukup, 1999, *RNA*, 5, 1308–1325). Therefore, the structural model indicates that cleavage of S21 should occur at the G residue residing at position 9 (FIG. 2). Consistent with the proposed "X-motif" model is the observation that a bimolecular construct comprised of S21 and a 46-nt RNA corresponding to the enzyme domain of a minimized X motif variant (FIG. 2) exhibits $Mg^{2+}$-dependent cleavage activity. Furthermore, the RNA cleavage was determined to occur at the phosphodiester linkage that resides 3' relative to the unpaired G (between nucleotides 9 and 10) of S21.

Applicant also examined the cleavage activity of a 44-nt construct that carries the conserved sequence and structural elements identified in class II ribozymes. This RNA forms a bimolecular interaction with S21 that presumably leaves unpaired the substrate nucleotides G and A at positions 6 and 7 (Table VIII). Consistent with this structural model, we find that the complex is cleaved within S21 between nucleotides 6 and 7 when $Mg^{2+}$ is included in the reaction mixture. In a similar fashion, bimolecular structures were tested for eight of the remaining 10 classes. In most instances, ribozyme activity and cleavage patterns are consistent with the proposed secondary structures depicted in FIG. 2.

Rate Constants for Prototypic Constructs Representing the 12 Ribozyme Classes

Rate constants for RNA transesterification were determined for each of the 12 constructs depicted in FIG. 2. For example, both class I and class II constructs produce linear cleavage kinetics through more than one half life of the substrate RNA (FIG. 3A). The representative class I and class II constructs examined herein exhibit rate constants of 0.01 and 0.05 $min^{-1}$, respectively. Similar examinations of the remaining ribozyme constructs reveal that the rate constants for RNA cleavage in nearly all cases are below 0.05 $min^{-1}$. In contrast, rate constants for the natural self-cleaving RNAs such as the hammerhead and HDV ribozymes typically range between 1 $min^{-1}$ and 100 $min^{-1}$ (Fedor and Uhlenbeck, 1999, *Biochemistry*, 31, 12042–12054). For comparison, the uncatalyzed rate of internal RNA transesterification under the selection conditions used is ~$10^{-7}$ $min^{-1}$ (Li and Breaker, 1999, *J. Am. Chem. Soc.*, 121, 5364–5372). Therefore, even the slowest of constructs depicted in FIG. 2 accelerate the chemical step of RNA cleavage by at least 1,000 fold. The most active prototype construct (class VIII, $k_{obs}$=0.1 $min^{-1}$) provides an overall chemical rate enhancement of ~1 million fold over the corresponding uncatalyzed rate.

It is important to note, however, that the original selection and the 20 independent reselections were conducted such that even very slow ribozymes were allowed to persist in the population. The isolation of ribozymes from random sequence employed ribozyme incubation times of 4 hr. Under these selection conditions, RNAs that self-cleave with a rate constant greater than $10^{-3}$ $min^{-1}$ experience little or no selective disadvantage compared to ribozymes that cleave with infinitely faster cleavage rates. Similarly, the goal of the reselections was to create variant ribozymes that retained activity so that an artificial phylogeny could be created for each representative RNA. The ribozyme incubations during reselection were typically carried out for 30–60 min. Therefore, the selective pressure applied at this stage also was not sufficient to favor the isolation of ribozymes with rates that rival those of naturally occurring ribozymes.

Ribozyme Cleavage Sites

Ribozymes and deoxyribozymes that catalyze the cleavage of RNA via a cyclizing mechanism typically require a specific consensus sequence at the site of cleavage. In most cases, substrate binding specificity is determined by Watson/Crick base pairing between enzyme and substrate domains, and this specificity can easily be engineered by the user. However, the hammerhead ribozyme favors cleavage of the phosphodiester linkage at UH sites, where H represents A, U or C (Vaish et al., 1998, *PNAS USA*, 95, 2158–2162). To maximize the diversity of ribozymes that could be isolated by applicant's selection scheme, applicant included the nearest neighbor domain depicted in FIG. 1B. This domain provides a comprehensive sampling of all 16 dinucleotides, thereby offering a greater diversity of cleavage sites than would be present in most substrate domains of arbitrary sequence composition. Applicant finds that the 12 classes of ribozymes examined in this study cleave at five different locations within the nearest neighbor domain (FIG. 3B). As predicted from RNA cleavage patterns, ribozymes isolated from the G6 population (classes I–IV) cleave at two sites— both near the 5' end of this domain. Similar correspondence between cleavage patterns and cleavage site selection are observed with ribozymes isolated from subsequent rounds. However, ribozymes from G12 and G15 that generate the largest 5'-cleavage fragments are not representative of new cleavage sites near the 3' end of the nearest neighbor domain. Applicant finds that several ribozymes accumulated insertions in the original $N_{40}$ domain that yield longer 5'-cleavage fragments despite processing at sites that are also used by other ribozymes. The most frequently used cleavage site is the linkage between the initial GA dinucleotide at the 5' end of the nearest neighbor domain, (FIG. 3B). However, it is not clear whether or not this dinucleotide sequence is intrinsically favorable to the formation of structures that self-cleave.

Class I "X motif"

Nearly all ribozyme constructs derived from the reselections (FIG. 2) exhibit rate constants for RNA cleavage that are far below the maximum values obtained for the natural self-cleaving ribozymes. This observation brings into question whether new RNA-cleaving motifs can even approach the catalytic efficiency of motifs that currently exist in nature. Until this point, applicant's in vitro selection and reselection efforts have been directed towards the identification and confirmation of new structural motifs for self-cleaving ribozymes. Therefore, the selection reactions intentionally were conducted under exceedingly permissive conditions such that even highly defective variants of new motifs could be enriched in the RNA population and ultimately be identified by cloning and sequencing. Likewise, reselections were conducted under almost equally permissive conditions in order to identify variants that could contribute to the assembly of artificial phylogenies, and not necessarily to produce superior catalysts. Indeed, none of the 20 reselections conducted, including one that was carried out using a mutagenized population derived from hammerhead i, provided variant ribozymes that exhibit kinetic characteristics like those displayed by natural self-cleaving ribozymes.

Figure 4:
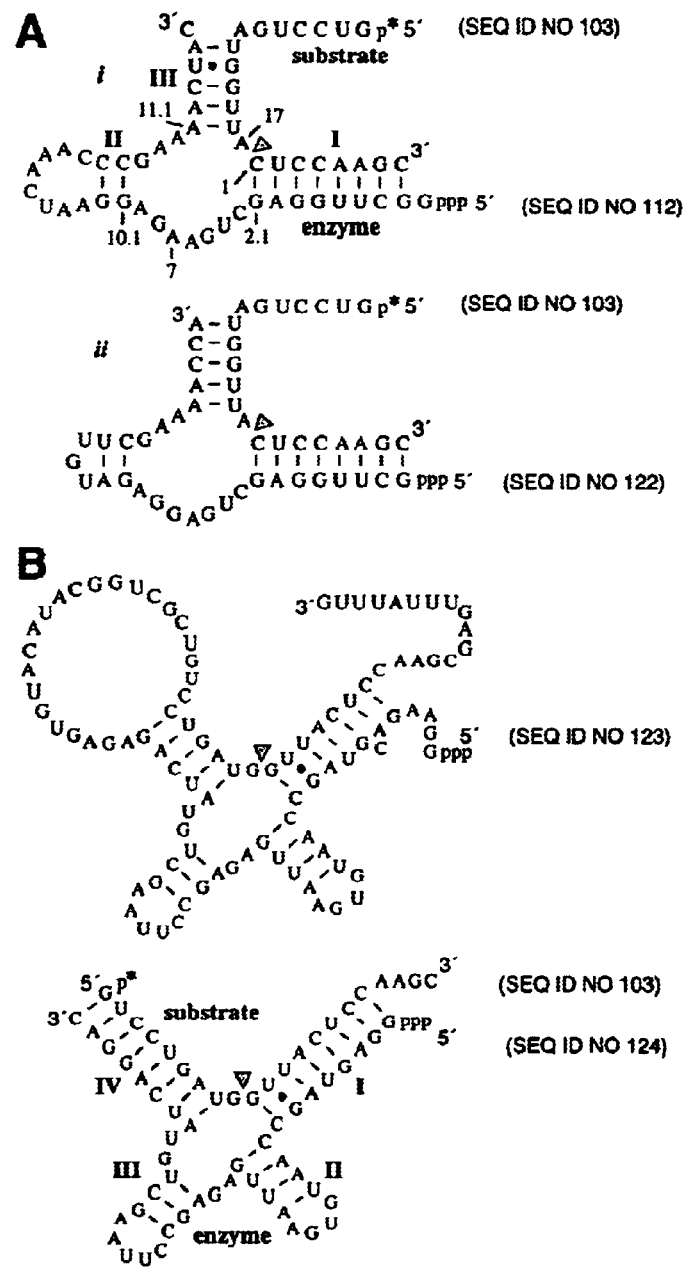

Therefore applicant set out to enrich for ribozyme variants whose rate constants were significantly higher than that of the general population. To this end, applicant pooled RNA samples from G6, G9, G12 and G15. This combined starting population was then subjected to additional rounds of in vitro selection as described in FIG. 1A, but where decreasing incubation times (as low as 5 sec) for the selection reaction were used to favor the isolation of the fastest ribozymes. After 10 additional rounds of selection, applicant found that the resulting RNA population undergoes ~6% cleavage upon incubation for 5 sec under the permissive reaction conditions. Surprisingly, only a single 5'-cleavage fragment is observed despite the fact that ribozymes cleaving at multiple sites within the nearest neighbor domain were selectively amplified. These results indicated that a single class of relatively fast ribozymes ($k_{obs}$~0.7 $min^{-1}$) has come to dominate the RNA population. Indeed, cloning and sequencing revealed that the population is comprised primarily of a single RNA sequence (FIG. 4B) that corresponds to a variation of the original X motif ribozyme (FIG. 2, class I).

A bimolecular construct based on the dominant self-cleaving RNA (FIG. 4B) exhibits a $k_{obs}$ of ~0.2 $min^{-1}$ under single turn-over conditions, which corresponds to a 20-fold improvement over the corresponding class I construct depicted in FIG. 2. This finding suggests that further improvements in catalytic performance might be made to the remaining classes of ribozymes, as the initial constructs examined likely reflect non-optimal variants. Interestingly, the maximum rate constant expected for optimal hammerhead ribozymes (~1 $min^{-1}$) remains several fold greater than that measured for the bimolecular version of the improved X motif depicted in FIG. 4B. Nevertheless, applicant concludes from these findings that other small RNA motifs can form RNA-cleaving structures that compare favorably in catalytic rate enhancement with that of natural ribozymes.

Ribozyme Engineering

Sequence, chemical and structural variants of ribozymes of the present invention can be engineered using the techniques shown above and known in the art to cleave a separate target RNA or DNA in trans. For example, the size of ribozymes can be reduced or increased using techniques known in the art (Zaug et al., 1986, *Nature*, 324, 429; Ruffner et al., 1990, *Biochem.*, 29, 6534; McCall et al., 1992, *Proc. Natl. Acad. Sci., USA.*, 89, 5710; Long et al., 1994, Supra; Hendry et al., 1994, *BBA* 1219, 405; Benseler et al., 1993, *JACS*, 115, 8483; Thompson et al., 1996, *Nucl. Acids Res.*, 24, 4401; Michels et al., 1995, *Biochem.*, 34, 2965; Been et al., 1992, *Biochem.*, 31, 11843; Guo et al., 1995, *EMBO. J.*, 14, 368; Pan et al., 1994, *Biochem.*, 33, 9561; Cech, 1992, *Curr. Op. Struc. Bio.*, 2, 605; Sugiyama et al., 1996, *FEBS Lett.*, 392, 215; Beigelman et al., 1994, *Bioorg. Med. Chem.*, 4, 1715; all are incorporated in their totality by reference herein). For example, the stem-loop domains of the ribozymes may not be essential for catalytic activity and hence could be systematically reduced in size using a variety of methods known in the art, to the extent that the overall catalytic activity of the ribozyme is not significantly decreased. In addition, the introduction of variant stem-loop structures via site directed mutagenesis and/or chemical modification can be employed to develop ribozymes with improved catalysis, increased stability, or both.

Further rounds of in vitro selection strategies described herein and variations thereof can be readily used by a person skilled in the art to evolve additional nucleic acid catalysts and such new catalysts are within the scope of the instant invention. In addition, the optimization of these variant ribozyme constructs by modification of stem-loop structures as is known in the art may provide for species with improved cleavage activity.

Example 1

Oligonucleotide Synthesis

Synthetic DNAs and the 21 nucleotide (nt) RNA substrate (S21) were prepared by standard solid phase methods (Keck Biotechnology Resource Laboratory, Yale University) and purified by denaturing (8 M urea) polyacrylamide gel electrophoresis (PAGE). The 2'-TBDMS groups of the synthetic RNA were removed by 24 hr treatment with triethylamine trihydrofluoride (15 µl per $AU_{260}$ crude RNA). Molecules that were radiolabeled using T4 polynucleotide kinase (T4 PNK, New England Biolabs) and [γ-$^{32}$P]ATP according to the manufacturer's directions were subsequently purified by denaturing 20% PAGE and isolated from the gel by crush-soaking in 10 mM Tris-HCl (pH 7.5 at 23° C.), 200 mM NaCl and 1 mM ethylenediaminetetraacetic acid (EDTA) followed by precipitation with ethanol as described below.

Example 2

In vitro Selection

The initial population of RNA for in vitro selection was created by first generating a double-stranded DNA template for in vitro transcription. SuperScript® II reverse transcriptase (RT, GibcoBRL) was used to extend 280 pmoles of the DNA oligonucleotide "primer 1" (5'-GAAATAAACTCGCTTGGAGTAACCATCAGG-ACAGCGACCGTA-3') (SEQ ID NO 99); region representing 16 possible nearest neighbor combinations is underlined) using 270 pmoles of the template DNA (5'-TCTAATACGACTCACTATAGGAAGACGTAGCCAA $N_{40}$TACGGTCGCTGTCC TG-3') (SEQ ID NO 100); T7 promoter is underlined and N represents an equal mixture of the four standard nucleotides). The extension reaction was conducted in a total of 50 µl containing 50 mM Tris-HCl (pH 8.3 at 23° C.), 75 mM KCl, 3 mM $MgCl_2$, 10 mM dithiothreitol (DTT), 0.2 mM each of the four deoxyribonucleoside-5' triphosphates (dNTPs), and 10 U µl$^{-1}$ RT by incubation at 37° C. for 1 hr. The resulting double-stranded DNA was precipitated by the addition of 5 µl 3 M sodium acetate (pH 5.5) and 140 µl 100% ethanol and pelleted by centrifugation. This extension reaction provides ~10$^{14}$ different template sequences.

The DNA templates were transcribed in a total volume of 100 µl containing 50 mM Tris-HCl (pH 7.5 at 23° C.), 10 mM $MgCl_2$, 50 mM DTT, 20 mM spermidine, 2 mM each of the four ribonucleoside-5' triphosphates (NTPs), and 35 U µl⁻¹ T7 RNA polymerase (T7 RNAP) by incubation at 37° C. for 1 hr. [α-$^{32}$P]UTP was added to the transcription reaction to produce internally $^{32}$P-labeled RNAs when necessary. The reaction was terminated by the addition of 50 µl 40 mM EDTA and precipitated by the addition of the appropriate amounts of sodium acetate and ethanol. The uncleaved precursor RNAs were isolated by denaturing 10% PAGE, recovered from the gel as described above and stored in deionized water (dH$_2$O) at −20° C. until use. In subsequent rounds of selection, double-stranded DNA from the polymerase chain reaction (PCR) was transcribed as described above, but for shorter periods of time (e.g. 10 min) to minimize the loss of ribozymes that efficiently cleave during transcription.

The initial selection reaction (G0) contained 2000 pmoles of RNA in a total of 400 µl reaction buffer (50 mM HEPES [pH 7.5 at 23° C.], 250 mM KCl and 20 mM MgCl$_2$) and was incubated at 23° C. for 4 hr. The reaction was terminated by the addition of EDTA and the RNA was recovered by precipitation with ethanol. RNA cleavage products were separated by denaturing 10% PAGE, visualized and quantified using a Molecular Dynamics PhosphorImager®, and the gel region corresponding to the location of the desired RNA cleavage products was excised. The RNA was recovered from the excised gel by crush-soak elution followed by precipitation with ethanol. The selected RNAs were amplified by RT-PCR as described previously (10) using primers 1 and 2 (5'-GAATTCTAATACGACTCACTATAGGAA-GACGTAGCCAA-3') (SEQ ID NO 101); T7 promoter is underlined). The resulting double-stranded DNA from each round of in vitro selection was used to transcribe the RNA population for the subsequent round, in which all steps were conducted at ~1/10$^{th}$ the scale of G0. All other parameters of the selection process were maintained as in G0. Representative ribozymes from the populations derived from 6, 9, 12 and 15 rounds of selection were examined by cloning (TOPO®-TA cloning kit; Invitrogen) and sequencing (ThermoSequenase® kit; Amersham Pharmacia).

Example 3
Artificial Phylogeny Generation

To confirm the self-cleaving activity of various clones, internally $^{32}$P-labeled ribozyme precursors were incubated under the selection reaction conditions for up to several hours to detect cleavage products upon separation by denaturing 10% PAGE. Artificial phylogenies for active clones each representing one of ~20 different sequence classes were generated by conducting reselections after the introduction of mutations. Reselections were conducted by first synthesizing a DNA construct for each individual that corresponds to the template strand for in vitro transcription. In each case, the nucleotides corresponding to the original random-sequence domain were synthesized with a degeneracy (d) of 0.21 per position, such that all possible variants with six or fewer mutations relative to the original sequence are represented. Typically, three to five rounds of selective amplification as described above (using selection reaction incubations of 1 hr or less) were required for each population to exhibit a level of catalytic activity that corresponded to that of the original clone. When this occurred, the population was cloned and sequenced.

Example 4
Characterization of Ribozyme Catalytic Function

In most cases, more detailed kinetic and structural characterizations of ribozymes from different structural classes were conducted with a variant from the corresponding artificial phylogeny that contains the mutations most commonly acquired during reselection. Initial rate constants for self-cleavage (classes VI and VII) were determined by incubating internally $^{32}$P-labeled ribozyme precursors in selection buffer for various times, separating the products by PAGE, and quantifying the yields by PhosphorImager®. Rate constants were derived as previously described (Soukup and Breaker, 1999, Proc. Natl. Acad. Sci. USA, 96, 3584–3589). Rate constants for bimolecular ribozyme function were established using a similar strategy, except that the reactions were allowed to proceed through at least two half lives of the substrate. To achieve single turnover conditions, trace amounts of $^{32}$P-labeled substrate were incubated with 500 nM ribozyme.

Cleavage sites for unimolecular reactions were determined by incubating 5' $^{32}$P-labeled precursor RNA in selection buffer, separating the products by denaturing 10% PAGE and comparing the gel mobility of the 5' cleavage fragment to that of each cleavage fragment generated by partial RNA digestion using RNase T1 or alkali as described previously (Soukup and Breaker, 1999, RNA, 5, 1308–1325). Similarly, the cleavage site for each bimolecular ribozyme reaction was established by incubating trace amounts of 5' $^{32}$P-labeled substrate RNA with 500 nM ribozyme and comparing the products of ribozyme cleavage, RNase T1 digestion, and alkaline digestion using denaturing 20% PAGE.

Example 5
Chemical Stabilization of Ribozyme Motif (Class V)

Examples of stabilized Class V ribozymes and control ribozymes useful in this study are shown in Table VII. Initially, ribozymes (Class V) were designed with varying combinations of 2'-O-methyl nucleotides. The ribozymes were chemically synthesized. Cleavage reactions were carried out with 500 nM final ribozyme concentration, single turnover kinetics in 50 mM Tris-Cl pH 7.5, 150 mM KCl, 20 mM Mg$^{2+}$, 37 C and trace substrate. Results are summarized in Table II. The all ribo wild type V ribozyme used as a control (RPI No. 14189) resulted in a cleavage rate (K$_{obs}$) of 0.044 min⁻¹. Two of the 2'-O-methyl constructs (RPI No. 14880 with 6 and 7 substituted 2'-O-Me arms, and RPI No. 14881 with 5 and 7 substituted 2'-O-Me arms), both resulted in improved cleavage activity with K$_{obs}$ values of 0.066 min⁻¹. RPI construct No 14880 was subsequently used as a control for a study to determine the effect of 2'-O-methyl substitution in the Class V ribozyme motif core via a 2'-O-methyl "walk" experiment using the same cleavage reaction conditions as above. The results of this study are summarized in FIG. 6 with K$_{obs}$ and K$_{rel}$ values summarized in Table III. The effect of various combinations of 2'-O-methyl substitutions in the Class V ribozyme core was investigated under the same conditions. Table IV outlines the results of this study in which a "seven ribose" core motif emerged with a K$_{obs}$ value of 0.127 min⁻¹. This seven ribose motif of the Class V ribozyme (RPI No. 15705) was used as the base motif for further core stabilization studies. Additional experiments focused on stabilization of the core pyrimidine residues of the Class V motif. Table V summarizes data from an experiment determining the cleavage activity Class V motif ribozymes with modified core pyrimidines with phosphorodithioate, 2'-fluoro, 2'-amino, and 2'-deoxy substitutions. This study indicates that the C7 position (FIG. 6) is the most tolerant to modifications while the U4 position is the least tolerant to modification. Further reductions in ribo core residues resulted in ribozymes with decreased activity relative to the "seven ribose" core version of the Class V motif, however, these further stabilized versions retained activity. Testing of the further reduced ribo constructs in conjunction with additional chemical modifications is summarized in Table VI.

Example 5
Similarity between Class I and Class VIII Ribozymes

Two strategies were used to examine whether the Class I and Class VIII ribozymes share sequence and structural similarities. First, a series of fourteen variant constructs were generated that examined the importance of various structural features of Class VIII ribozymes. For example, the 5'-leader sequence of Class VIII is essential, only when the extra bulge immediately preceding the stem II element is present. If this bulge and putative stem II element is replaced by a more convincing stem II structure like that present in the Class I motif structure (FIG. 7), then the leader sequence of Class VIII can be eliminated. In a similar fashion, other elements of Class VIII ribozymes when examined, show similarity to those of Class I ribozymes. A series of kinetic analyses were used to compare the characteristics of the Class I and Class VIII motifs. In each case, the bimolecular constructs depicted in FIG. 7 were used for comparison. Each of these substrates (trace) can be saturated with ribozyme as depicted in FIG. 8a. Furthermore, each motif has near identical characteristics upon variation of monovalent salt (FIG. 8b), pH (FIG. 8c), and divalent magnesium (FIG. 8d). These results support the view that, at their respective core, the Class I and Class VIII motifs are similar.

Diagnostic Uses

Enzymatic nucleic acids of this invention can be used as diagnostic tools to examine genetic drift and mutations within diseased cells or to detect the presence of target RNA in a cell. The close relationship between ribozyme activity and the structure of the target RNA allows the detection of mutations in any region of the molecule which alters the base-pairing and three-dimensional structure of the target RNA. By using multiple ribozymes described in this invention, one can map nucleotide changes which are important to RNA structure and function in vitro, as well as in cells and tissues. Cleavage of target RNAs with ribozymes can be used to inhibit gene expression and define the role (essentially) of specified gene products in the progression of disease. In this manner, other genetic targets can be defined as important mediators of the disease. These experiments can lead to better treatment of the disease progression by affording the possibility of combinational therapies (e.g., multiple ribozymes targeted to different genes, ribozymes coupled with known small molecule inhibitors, or intermittent treatment with combinations of ribozymes and/or other chemical or biological molecules). Other in vitro uses of ribozymes of this invention are well known in the art, and include detection of the presence of mRNAs associated with disease condition. Such RNA is detected by determining the presence of a cleavage product after treatment with a ribozyme using standard methodology.

In a specific example, ribozymes which cleave only wild-type or mutant forms of the target RNA are used for the assay. The first ribozyme is used to identify wild-type RNA present in the sample and the second ribozyme is used to identify mutant RNA in the sample. As reaction controls, synthetic substrates of both wild-type and mutant RNA are cleaved by both ribozymes to demonstrate the relative ribozyme efficiencies in the reactions and the absence of cleavage of the "non-targeted" RNA species. The cleavage products from the synthetic substrates also serve to generate size markers for the analysis of wild-type and mutant RNAs in the sample population. Thus each analysis involves two ribozymes, two substrates and one unknown sample which is combined into six reactions. The presence of cleavage products is determined using an RNAse protection assay so that full-length and cleavage fragments of each RNA can be analyzed in one lane of a polyacrylamide gel. It is not absolutely required to quantify the results to gain insight into the expression of mutant RNAs and putative risk of the desired phenotypic changes in target cells. The expression of mRNA whose protein product is implicated in the development of the phenotype is adequate to establish risk. If probes of comparable specific activity are used for both transcripts, then a qualitative comparison of RNA levels will be adequate and will decrease the cost of the initial diagnosis. Higher mutant form to wild-type ratios will be correlated with higher risk whether RNA levels are compared qualitatively or quantitatively.

Additional Uses

Potential uses of sequence-specific enzymatic nucleic acid molecules of the instant invention include many of the same applications for the study of RNA that DNA restriction endonucleases have for the study of DNA (Nathans et al., 1975 *Ann. Rev. Biochem.* 44:273). For example, the pattern of restriction fragments can be used to establish sequence relationships between two related RNAs, and large RNAs could be specifically cleaved to fragments of a size more useful for study. The ability to engineer sequence specificity of the ribozyme is ideal for cleavage of RNAs of unknown sequence.

The nucleic acid catalysts of the instant invention can be used to specifically cleave an RNA sequence for which an appropriately engineered nucleic acid catalyst base pairs at the designated flanking regions (e.g., X and Y in Formulae 1 and 2). Suitable target RNA substrates include viral, messenger, transfer, ribosomal, nuclear, organellar, other cellular RNA, or any other natural RNA having a cleavage sequence, as well as RNAs, which have been engineered to contain an appropriate cleavage sequence. The nucleic acid catalysts are useful in vivo in prokaryotes or eukaryotes of plant or animal origin for controlling viral infections or for regulating the expression of specific genes.

Once introduced into the cell, the nucleic acid catalyst bind to the target RNA and cleave the target RNA sequence or sequences for which it has been designed, inactivating the RNA. If the RNA is necessary for the life cycle of a virus, the virus is eliminated and if the RNA is the product of a specific gene, the expression of that gene is regulated. The nucleic acid catalyst can be designed to work in prokaryotes and within the nucleus (without poly(A) tail) or in the cytoplasm of a eukaryotic cell (with polyadenylation signals in place) for plants and animals.

All patents and publications mentioned in the specification are indicative of the levels of skill of those skilled in the art to which the invention pertains. All references cited in this disclosure are incorporated by reference to the same extent as if each reference had been incorporated by reference in its entirety individually.

One skilled in the art would readily appreciate that the present invention is well adapted to carry out the objects and obtain the ends and advantages mentioned, as well as those inherent therein. The methods and compositions described herein as presently representative of preferred embodiments are exemplary and are not intended as limitations on the scope of the invention. Changes therein and other uses will occur to those skilled in the art, which are encompassed within the spirit of the invention, are defined by the scope of the claims.

It will be readily apparent to one skilled in the art that varying substitutions and modifications may be made to the invention disclosed herein without departing from the scope and spirit of the invention. Thus, such additional embodiments are within the scope of the present invention and the following claims.

The invention illustratively described herein suitably may be practiced in the absence of any element or elements, limitation or limitations which is not specifically disclosed herein. Thus, for example, in each instance herein any of the terms "comprising", "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, optional features, modification and variation of the concepts herein disclosed may be resorted to by those skilled in the art, and that such modifications and variations are considered to be within the scope of this invention as defined by the description and the appended claims.

In addition, where features or aspects of the invention are described in terms of Markush groups or other grouping of alternatives, those skilled in the art will recognize that the invention is also thereby described in terms of any individual member or subgroup of members of the Markush group or other group.

Thus, additional embodiments are within the scope of the invention and within the claims that follow.

TABLE I

| Reagent | Equivalents | Amount | Wait Time* DNA | Wait Time* 2'-O-methyl | Wait Time* RNA |
|---|---|---|---|---|---|
| A. 2.5 μmol Synthesis Cycle ABI 394 Instrument ||||||
| Phosphoramidites | 6.5 | 163 μL | 45 sec | 2.5 min | 7.5 min |
| S-Ethyl Tetrazole | 23.8 | 238 μL | 45 sec | 2.5 min | 7.5 min |
| Acetic Anhydride | 100 | 233 μL | 5 sec | 5 sec | 5 sec |
| N-Methyl Imidazole | 186 | 233 μL | 5 sec | 5 sec | 5 sec |
| TCA | 176 | 2.3 mL | 21 sec | 21 sec | 21 sec |
| Iodine | 11.2 | 1.7 mL | 45 sec | 45 sec | 45 sec |
| Beaucage | 12.9 | 645 μL | 100 sec | 300 sec | 300 sec |
| Acetonitrile | NA | 6.67 mL | NA | NA | NA |

| Reagent | Equivalents | Amount | Wait Time* DNA | Wait Time* 2'-O-methyl | Wait Time* RNA |
|---|---|---|---|---|---|
| B. 0.2 μmol Synthesis Cycle ABI 394 Instrument ||||||
| Phosphoramidites | 15 | 31 μL | 45 sec | 233 sec | 465 sec |
| S-Ethyl Tetrazole | 38.7 | 31 μL | 45 sec | 233 min | 465 sec |
| Acetic Anhydride | 655 | 124 μL | 5 sec | 5 sec | 5 sec |
| N-Methyl Imidazole | 1245 | 124 μL | 5 sec | 5 sec | 5 sec |
| TCA | 700 | 732 μL | 10 sec | 10 sec | 10 sec |
| Iodine | 20.6 | 244 μL | 15 sec | 15 sec | 15 sec |
| Beaucage | 7.7 | 232 μL | 100 sec | 300 sec | 300 sec |
| Acetonitrile | NA | 2.64 mL | NA | NA | NA |

| Reagent | Equivalents DNA/2'-O-methyl/Ribo | Amount DNA/2'-O-methyl/Ribo | Wait Time* DNA | Wait Time* 2'-O-methyl | Wait Time* Ribo |
|---|---|---|---|---|---|
| C. 0.2 μmol Synthesis Cycle 96 well Instrument ||||||
| Phosphoramidites | 22/33/66 | 40/60/120 μL | 60 sec | 180 sec | 360 sec |
| S-Ethyl Tetrazole | 70/105/210 | 40/60/120 μL | 60 sec | 180 min | 360 sec |
| Acetic Anhydride | 265/265/265 | 50/50/50 μL | 10 sec | 10 sec | 10 sec |
| N-Methyl Imidazole | 502/502/502 | 50/50/50 μL | 10 sec | 10 sec | 10 sec |
| TCA | 238/475/475 | 250/500/500 μL | 15 sec | 15 sec | 15 sec |
| Iodine | 6.8/6.8/6.8 | 80/80/80 μL | 30 sec | 30 sec | 30 sec |
| Beaucage | 34/51/51 | 80/120/120 | 100 sec | 200 sec | 200 sec |
| Acetonitrile | NA | 1150/1150/1150 μL | NA | NA | NA |

*Wait time does not include contact time during delivery.

TABLE II

Class V ribozyme 2'-O-methyl arm optimization

| RPI No. | DESCRIPTION | $k_{obs}$ (min.$^{-1}$) | % in 1$^{st}$ exponential |
|---|---|---|---|
| 14880 | 6 @ 7 2'-O-Me arms | 0.066 | 82.3 |
| 14881 | 5 @ 7 2'-O-Me arms | 0.066 | 81.0 |
| 14189 | WT all ribose "bulged U" | 0.044 | 72.5 |
| 14882 | 5 @ 6 2'-O-Me arms | 0.043 | 76.6 |
| 14883 | 5 @ 5 2'O-Me arms | 0.037 | 75.4 |
| 14885 | 4 @ 4 2'-O-Me arms | 0.031 | 84.0 |

TABLE II-continued

Class V ribozyme 2'-O-methyl arm optimization

| RPI No. | DESCRIPTION | $k_{obs}$ (min.$^{-1}$) | % in 1$^{st}$ exponential |
|---|---|---|---|
| 14884 | 4 @ 5 2'-O-Me arms | 0.030 | 82.8 |
| 14879 | 6 @ 8 2'-O-Me arms | 0.0009 | 60.0 |

TABLE III

Class V ribozyme motif 2'-O-methyl core "walk"

| RPI No. | DESCRIPTION | $k_{obs}$ (min.$^{-1}$) | Krel to .20672 |
|---|---|---|---|
| 14189 | WT All Ribose Assay Control | 0.036 | 0.64 |
| 14880 | 6 @ 7 2'-OMe Arms gel-purified | 0.061 | 1.09 |
| 15297 | 6 @ 7 2'-OMe Arms crude synthesis | 0.056/0.058 | 1.00 |
| 15305 | 6 @ 7 2'-OMe Arms + Core 2'-OMe A6 | 0.072 | 1.29 |
| 15310 | 7 @ 7 2'-OMe Arms ribo core | 0.070 | 1.25 |
| 15309 | 6 @ 7 2'-OMe Arms + Core 2'-OMe G2 | 0.069 | 1.23 |
| 15299 | 6 @ 7 2'-OMe Arms + Core 2'-OMe A12 | 0.068 | 1.21 |
| 15300 | 6 @ 7 2'-OMe Arms + Core 2'-OMe A11 | 0.060 | 1.07 |
| 15306 | 6 @ 7 2'-OMe Arms + Core 2'-OMe A5 | 0.057 | 1.02 |
| 15301 | 6 @ 7 2'-OMe Arms + Core 2'-OMe G10 | 0.050 | 0.89 |
| 15298 | 6 @ 7 2'-OMe Arms + Core 2'-OMe G13 | 0.030 | 0.54 |
| 15303 | 6 @ 7 2'-OMe Arms + Core 2'-OMe G8 | 0.029 | 0.52 |
| 15304 | 6 @ 7 2'-OMe Arms + Core 2'-OMe C7 | 0.017 | 0.30 |
| 15308 | 6 @ 7 2'-OMe Arms + Core 2'-OMe A3 | 0.010 | 0.17 |
| 15302 | 6 @ 7 2'-OMe Arms + Core 2'-OMe U9 | 0.0004 | 0.007 |
| 15307 | 6 @ 7 2'-OMe Arms + Core 2'-OMe U4 | 0.0001 | 0.002 |
| 15311 | All 2'-OMe A14.1 = Ribo | 0.00008 | 0.001 |

TABLE IV

Class V ribozyme motif combination core

| RPI No. | DESCRIPTION (all other residues = 2'-O-Methyl) | $k_{abs}$ (min.$^{-1}$) | $k_{rel}$ to .20672 All Ribo Core |
|---|---|---|---|
| 15705 | 7 RIBO CORE A3, U4, C7, G8, U9, G13, A14.1 = ribo | 0.127 | 2.31 |
| 15297 | ALL RIBO "CORE" G2 – A14.1 = ribo | 0.055 | 1.00 |
| 15702 | 6 RIBO CORE U4, C7, G8, U9, G13, A14.1 = ribo | 0.036 | 0.65 |
| 15700 | 4 RIBO "CORE" U4, C7, U9, A14.1 = ribo | 0.0019 | 0.03 |
| 15701 | 5 RIBO "CORE" U4, C7, G8, U9, A14.1 = ribo | 0.0012 | 0.02 |
| 15703 | 3 RIBO CORE U4, U9, A14.1 = ribo | 0.0006 | 0.01 |
| 15704 | 3 RIBO CORE U4, U9, A14.1 = ribo | 0.0006 | 0.01 |

TABLE V

Class V ribozyme motif with pyrimidine stabilized core

| RPI No. | DESCRIPTION | $k_{obs}$ (min.$^{-1}$) | $k_{rel}$ to .21422 (7 Ribo Core) | $k_{rel}$ to .20672 (All Ribo Core) |
|---|---|---|---|---|
| 15705 | 7 RIBO CORE A3, U4, C7, G8, U9, G13, A14.1 = ribo | 0.113 | 1.00 | 2.05 |
| 16188 | "7 ribo" U4 = PS2 | 0.144 | 1.28 | 2.62 |
| 16191 | "6 ribo" C7 = 2'F-C | 0.121 | 1.07 | 2.2 |
| 16197 | "6 ribo" C7 = 2-NH2-C | 0.063 | 0.56 | 1.15 |
| 16186 | "7 ribo" U9 = PS2 | 0.063 | 0.56 | 1.15 |
| 16194 | "6 ribo" C7 = 2-deoxy-C | 0.030 | 0.27 | 0.55 |
| 16196 | "6 ribo" U9 = 2-NH2-U | 0.025 | 0.22 | 0.45 |
| 16192 | "6 ribo" U9 = 2'F-U | 0.015 | 0.13 | 0.27 |
| 16195 | "6 ribo" U9 = 2-deoxy-U | 0.011 | 0.10 | 0.20 |
| 16198 | "6 ribo" U4 = 2-NH2-U | 0.001 | 0.009 | 0.02 |
| 16190 | "6 ribo" U4 = 2'F-U | 0.0005 | 0.004 | 0.009 |
| 16193 | "6 ribo" U4 = 2'-deoxy-U | 0.0002 | 0.002 | 0.004 |

PS2 = phosphorodithioate linkage
2'-F-U = 2'-deoxy-2'-fluoro uridine
2'-F-C = 2'-deoxy-2'-fluoro cytidine
2'-NH2-U = 2'-deoxy-2'-amino uridine
2'-NH2-C = 2'-deoxy-2'-amino cytidine

TABLE VI

Class V ribozyme motif with reduced ribo content

| RPI No | DESCRIPTION | $k_{abs}$ (min.$^{-1}$) | $k_{rel}$ to .21422 (7 Ribo Core) | $k_{rel}$ to .20672 (All Ribo Core) |
|---|---|---|---|---|
| 15705 | 7 RIBO CORE A3, U4, C7, G8, U9, G13, A14.1 = ribo | 0.117 | 1.00 | 2.13 |
| 16013 | 4 RIBO CORE U4, G8, U9, A14.1 = ribo | 0.041 | 0.35 | 0.75 |
| 17584 | 4 RIBO U4, U9 = PS C7 = 2'-OMe | 0.0008 | 0.007 | 0.02 |
| 17585 | 5 RIBO U4, U9 = PS C7 = 2'-OMe | 0.0018 | 0.02 | 0.03 |
| 17586 | 4 RIBO U4 = PS, U9 = NH2 C7 = 2'-OMe | 0.0003 | 0.003 | 0.005 |
| 17587 | 5 RIBO U4 = PS, U9 = NH2 C7 = 2'-OMe | 0.0006 | 0.005 | 0.01 |

TABLE VI-continued

Class V ribozyme motif with reduced ribo content

| RPI No | DESCRIPTION | $k_{abs}$ (min.$^{-1}$) | $k_{rel}$ to .21422 (7 Ribo Core) | $k_{rel}$ to .20672 (All Ribo Core) |
|---|---|---|---|---|
| 17589 | 5 RIBO U4 = PS, U9 = NH2 C7 = 2'-F | 0.0021 | 0.02 | 0.04 |
| 17590 | 7 RIBO C7 = PS | 0.105 | 0.90 | 1.91 |
| 17591 | 6 RIBO U4, U9 = PS C7 = 2'-OMe | 0.022 | 0.19 | 0.40 |
| 17588 | 4 RIBO U4, U9 = PS C7 = 2'F | 0.012 | 0.10 | 0.22 |

PS = phosphorothioate linkage
2'-F = 2'-deoxy-2'-fluoro

TABLE VII

Class V ribozymes

| Synth No. | RPI No. | Seq. ID No. | Ribozyme |
|---|---|---|---|
| 19984 | 14880 | 1 | gga guaA GA UAA CGU GAA G Au cag gacB |
| 19985 | 14881 | 2 | gga guAA GA UAA CGU GAA G Au cag gacB |
| 19120 | 14189 | 3 | GGA GUA AGA UAA CGU GAA G AU CAG GAC |
| 19986 | 14882 | 4 | gga guAA GA UAA CGU GAA G AU cag gacB |
| 19987 | 14883 | 5 | gga guAA GA UAA CGU GAA G AU Cag gacB |
| 19989 | 14885 | 6 | gga gUAA GA UAA CGU GAA G AU CAg gacE |
| 19988 | 14884 | 7 | gga gUAA GA UAA CGU GAA G AU Cag gacB |
| 19983 | 14879 | 8 | gga guaA GA UAA CGU GAA G au cag gacB |
| 20680 | 15305 | 9 | gga guaA GA UAa CGU GAA G Au cag gacB |
| 20685 | 15310 | 10 | gga guaa GA UAA CGU GAA G Au cag gacB |
| 20684 | 15309 | 11 | gga guaA GA UAA CGU GAA G Au cag gacB |
| 20674 | 15299 | 12 | gga guaA GA UAA CGU GAa G Au cag gacB |
| 20675 | 15300 | 13 | gga guaA GA UAA CGU GaA G Au cag gacB |
| 20681 | 15306 | 14 | gga guaA GA UaA CGU gAA G Au cag gacB |
| 20676 | 15301 | 15 | gga guaA GA UAA CGU GAA G Au cag gacB |
| 20673 | 15298 | 16 | gga guaA GA UAA CGU GAA g Au cag gacB |
| 20678 | 15303 | 17 | gga guaA GA UAA CgU GAA G Au cag gacS |
| 20679 | 15304 | 18 | gga guaA GA UAA cGU GAA G Au cag gacB |
| 21076 | 15308 | 19 | gga guaA GA UAA CGU GAA G Au cag gacB |
| 20677 | 15302 | 20 | gga guaA GA UAA CGu GAA G Au cag gacB |
| 21075 | 15307 | 21 | gga guaA GA uAA CGU GAA G Au cag gacB |
| 20686 | 15311 | 22 | gga guaa ga uaa cgu gaa g Au cag gacB |
| 21422 | 15705 | 23 | gga guaa gA Uaa CGU gaa G Au cag gacB |
| 21577 | 15702 | 24 | gga guaa ga Uaa CGU gaa G Au cag gacB |
| 21417 | 15700 | 25 | gga guaa ga Uaa CgU gaa g Au cag gacB |

TABLE VII-continued

Class V ribozymes

| Synth No. | RPI No. | Seq. ID No. | Ribozyme |
|---|---|---|---|
| 21418 | 15701 | 26 | gga guaa ga Uaa CGU gaa g Au cag gacB |
| 21420 | 15703 | 27 | gga guaa ga Uaa cgU gaa g Au cag gacB |
| 22128 | 16188 | 28 | gga guaa gA U$_{S2}$aa CGU gaa G Au cag gacB |
| 22131 | 16191 | 29 | gga guaa gA Uaa <u>C</u>GU gaa G Au cag gacB |
| 22137 | 16197 | 30 | gga guaa gA Uaa CGU gaa G Au cag gacB |
| 22126 | 16186 | 31 | gga guaa gA Uaa CGU$_{S2}$ gaa G Au cag gacB |
| 22134 | 16194 | 32 | gga guaa gA Uaa <u>C</u>CGU gaa G Au cag gacB |
| 22136 | 16196 | 33 | gga guaa gA Uaa CG<u>U</u> gaa G Au cag gacB |
| 22132 | 16192 | 34 | gga guaa gA Uaa CG<u>U</u> gaa G Au cag gacB |
| 22135 | 16195 | 35 | gga guaa gA Uaa CG<u>U</u> gaa G Au cag gacS |
| 22138 | 16198 | 36 | gga guaa gA Uaa CGU gaa G Au cag gacB |
| 22130 | 16190 | 37 | gga guaa gA <u>U</u>aa CGU gaa G Au cag gacB |
| 22133 | 16193 | 38 | gga guaa gA <u>U</u>aa CGU gaa G Au cag gacB |
| 21818 | 16013 | 39 | gga guaa ga Uaa cGU gaa g Au cag gacB |
| 23786 | 17584 | 40 | gga guaa ga U$_S$aa cGU$_S$ gaa g Au cag gacB |
| 23787 | 17585 | 41 | gga guaa ga U$_S$aa CGU$_S$ gaa G Au cag gacB |
| 23788 | 17586 | 42 | gga guaa ga U$_S$aa cGU gaa g Au cag gacB |
| 23789 | 17587 | 43 | gga guaa ga U$_S$aa cGU gaa G Au cag gacB |
| 23791 | 17589 | 44 | gga guaa ga U$_S$aa <u>C</u>GU gaa G Au cag gacB |
| 23792 | 17590 | 45 | gga guaa ga Uaa C$_S$GU gaa G Au cag gacB |
| 23793 | 17591 | 46 | gga guaa ga U$_S$aa cGU$_S$ gaa G Au cag gacB |
| 24021 | 17588 | 47 | gga guaa ga U$_S$aa <u>C</u>GU$_S$ gaa G Au cag gacB |

<u>U</u>, <u>C</u> = 2'-deoxy-2'-fluoro Uridine, Cytidine
U, C = 2'-deoxy Uridine, Cytidine
U, C = 2'-deoxy-2'-amino Uridine, Cytidine
UPPER CASE = RIBO
lower case = 2'-O-Methyl
S = phosphorothioate linkage
S2 = phosphorodithioate linkage
B = 3',3'-inverted deoxyabasic moiety

TABLE VIII

Class I

```
                    10        20        30        40
                    .         .         .         .
wild type: AUGCAAUGCAUUUGAGAACUGUAAGUUGUAUGAGGGCAUG    (SEQ ID NO 48)
    1      ...UG........ ......C....................  (SEQ ID NO 49)
    2      U.......C.........A.........U....AG..      (SEQ ID NO 50)
    3      G.......................U...UG..           (SEQ ID NO 51)
    4      .....C..........A.A.............AG..       (SEQ ID NO 52)
    5      .....U...G.........G......A............    (SEQ ID NO 53)
    6      G..................G.......U...U....       (SEQ ID NO 54)
    7      ...U........CA.........U............       (SEQ ID NO 55)
    9      ......U.........C...........C........      (SEQ ID NO 56)
   10      ................C.................G..      (SEQ ID NO 57)
   11      .....G.G........UC.................         (SEQ ID NO 58)
   12      .....U....C.......G...A...C..G.........G..  (SEQ ID NO 59)
```

TABLE VIII-continued

| | | |
|---|---|---|
| 14 | G.....................G.........U.......A | (SEQ ID NO 60) |
| 17 | ....U................AG.........G.....C. | (SEQ ID NO 61) |
| 18 | .....G...G..........................C......G. | (SEQ ID NO 62) |
| 19 | G......................................... | (SEQ ID NO 63) |
| 21 | ...A.................G.................G. | (SEQ ID NO 64) |
| 22 | G.....................A.................U | (SEQ ID NO 65) |
| 23 | G.....................A.........U...U.... | (SEQ ID NO 66) |

Class II

```
                    10        20        30        40
                    .         .         .         .
wild type:  GGCGAUAGGUGAGUACACUGGGUCGGAGGGAUAGCUAGGU    (SEQ ID NO 67)
     1'     .......A...C....................C........    (SEQ ID NO 68)
     2'     .......A........................A           (SEQ ID NO 69)
     3'     .........C..............................    (SEQ ID NO 70)
     2      .........A.....A........................    (SEQ ID NO 71)
     3      ............................A.........      (SEQ ID NO 72)
     7      .......A...G....................GG....      (SEQ ID NO 73)
     8      .......A........A.......................    (SEQ ID NO 74)
     9      .............A.......................ACA    (SEQ ID NO 75)
    21      ............G...................U....UC     (SEQ ID NO 76)
    24      ............A...................CG......C   (SEQ ID NO 77)
    26      ................................GU...       (SEQ ID NO 78)
    29      .....C.....UU....................A.C         (SEQ ID NO 79)
    30      ..........U....................C.            (SEQ ID NO 80)
    31      ...............  ................U.G....    (SEQ ID NO 81)
    34      ..........................G...GA..A.        (SEQ ID NO 82)
```

Class V

```
                    10        20        30        40
                    .         .         .         .
wild type:  GGCUCGUGGGGAGUGAGAUAACGUGAAGAUCUAGGGCGGGGGA    (SEQ ID NO 83)
     2      ........C........  .....................U.....    (SEQ ID NO 84)
     3      .......U...G............................U..     (SEQ ID NO 85)
     5      U...U...C.....................G.....A.....      (SEQ ID NO 86)
     6      ........C.....A..................AC......U.C    (SEQ ID NO 87)
     7      ....G..U.........................U..            (SEQ ID NO 88)
     9      ......C........  .....................U...      (SEQ ID NO 89)
    10      .A..........A...................U....U..U..     (SEQ ID NO 90)
    11      ....U..UU......  .....................C.C..     (SEQ ID NO 91)
    12      .........C...............A.......U..U           (SEQ ID NO 92)
    13      ..........A......................U..C...        (SEQ ID NO 93)
    14      .................................A.U.UA.G      (SEQ ID NO 94)
    17      .A...............................C..U.          (SEQ ID NO 95)
    19      .............................C..                (SEQ ID NO 96)
```

---

What is claimed is:

1. A nucleic acid molecule with endonuclease activity having the formula II:3'—X—Z—Y—5' wherein, X and Y are independently oligonucleotides of length sufficient to stably interact with a target nucleic acid molecule; Z is an oligonucleotide having a nucleotide sequence selected from the group consisting of 5'-AGAUAACGUGAAGAU-3' SEQ ID NO:97) and 5'-AAUGGCCUAUCGGUGCGA-3' (SEQ ID NO: 98).

2. The nucleic acid molecule with endonuclease activity of claim 1, wherein said chemical linkage is independently or in combination selected from the group consisting of phosphate ester amide, phosphorothioate, phosphorodithioate, arabino, and arabinofluoro linkages.

3. The nucleic acid molecule with endonuclease activity of claim 1, wherein said nucleic acid molecule is chemically synthesized.

4. The nucleic acid molecule with endonuclease activity of claim 1, wherein said nucleic acid molecule comprises at least one sugar modification.

5. The nucleic acid molecule with endonuclease activity of claim, wherein said nucleic acid molecule comprises at least one nucleic acid base modification.

6. The nucleic acid molecule with endonuclease activity of claim 1, wherein said nucleic acid molecule comprises at least one phosphate backbone modification.

7. The nucleic acid molecule with endonuclease activity of claim 4, wherein said sugar modification is selected from the group consisting of 2'-H, 2'-O-methyl, 2'-O-allyl, 2'-C-allyl, 2'-deoxy-2'-fluoro, and 2'-deoxy-2'-amino modifications.

8. The nucleic acid molecule with endonuclease activity of claim 6, wherein said phosphate backbone modification is selected from the group consisting of phosphorothioate, phosphorodithioate, and amide modifications.

9. The nucleic acid molecule with endonuclease activity of claim 1, wherein said nucleic acid molecule comprises a 5'-cap, a 3'-cap, or both a 5'-cap and a 3'-cap.

10. The nucleic acid molecule with endonuclease activity of claim 9, wherein said 5'-cap is a phosphorothioate modification of at least one 5'-terminal nucleotide in said nucleic acid molecule.

11. The nucleic acid molecule with endonuclease activity of claim 9, wherein said 5'-cap is a phosphorothioate modification of at least two 5'-terminal nucleotides in said nucleic acid molecule.

12. The nucleic acid molecule with endonuclease activity of claim 9, wherein said 5'-cap is a phosphorothioate modification of at least three 5'-terminal nucleotides in said nucleic acid molecule.

13. The nucleic acid molecule with endonuclease activity of claim 9, wherein said 5'-cap is a phosphorothioate modification of at least four 5'-terminal nucleotides in said nucleic acid molecule.

14. The nucleic acid molecule with endonuclease activity of claim 9, wherein said 3'-cap is a 3'-3' inverted riboabasic moiety.

15. The nucleic acid molecule with endonuclease activity of claim 9, wherein said 3'-cap is a 3'-3' inverted deoxyriboabasic moiety.

16. The nucleic acid molecule with endonuclease activity of claim 1, wherein said nucleic acid cleaves a separate nucleic acid molecule.

17. The nucleic acid molecule with endonuclease activity of claim 16, wherein said separate nucleic acid molecule is RNA.

18. The nucleic acid molecule with endonuclease activity of claim 16, wherein said nucleic acid comprises between 12 and 100 bases complementary to said separate nucleic acid molecule.

19. The nucleic acid molecule with endonuclease activity of claim 16, wherein said nucleic acid comprises between 14 and 24 bases complementary to said separate nucleic acid molecule.

20. The nucleic acid molecule with endonuclease activity of claims 1, wherein said X and Y are independently of length selected from the group consisting of 3, 4, 5, 6, 7, 8, 9, 10, 11, 12, 13, 14, 15, 17, and 20 nucleotides.

21. The nucleic acid molecule with endonuclease activity of claim 1, wherein the length of X is equal to the length of Y.

22. The nucleic acid molecule with endonuclease activity of claim 1, wherein the length of X is not equal to the length of Y.

23. An isolated cell including the nucleic acid molecule with endonuclease activity of claim 1.

24. The isolated cell of claim 23, wherein said cell is a mammalian cell.

25. The isolated cell of claim 24, wherein said cell is a human cell.

26. An expression vector comprising a nucleic acid sequence encoding the nucleic acid molecule with endonuclease activity of claim 1, in a manner which allows expression of the nucleic acid molecule with endonuclease activity.

27. An isolated cell including the expression vector of claim 26.

28. The isolated cell of claim 27, wherein said cell is a mammalian cell.

29. The isolated cell of claim 28, wherein said cell is a human cell.

30. A composition comprising the nucleic acid molecule with endonuclease activity of claim 1 and a phamaceutically acceptable diluent.

31. The expression vector of claim 26, wherein said vector comprises: a) a transcription initiation region; b) a transcription termination region; c) a nucleic acid sequence encoding the nucleic acid molecule with endonuclease activity of claim 2; and wherein said nucleic acid sequence is operably linked to said initiation region and said termination region, in a manner which allows expression and/or delivery of said nucleic acid molecule.

32. The expression vector of claim 26, wherein said vector comprises: a) a transcription initiation region; b) a transcription termination region; c) an open reading frame; d) a nucleic acid sequence encoding the nucleic acid molecule with endonuclease activity of claim 2, wherein said sequence is operably linked to the 3'-end of said open reading frame; and wherein said nucleic acid sequence is operably linked to said initiation region, said open reading frame and said termination region, in a manner which allows expression and/or delivery of said nucleic acid molecule.

33. The expression vector of claim 26, wherein said vector comprises: a) a transcription initiation region; b) a transcription termination region; c) an intron; d) a nucleic acid sequence encoding the nucleic acid molecule with endonuclease activity of claim 2; and wherein said nucleic acid sequence is operably linked to said initiation region, said intron and said termination region, in a manner which allows expression and/or delivery of said nucleic acid molecule.

34. The expression vector of claim 26, wherein said vector comprises: a) a transcription initiation region; b) a transcription termination region; c) an intron; d) an open reading frame; e) a nucleic acid sequence encoding the nucleic acid molecule with endonuclease activity of claim 2, wherein said sequence is operably linked to the 3'-end of said open reading frame; and wherein said nucleic acid sequence is operably linked to said initiation region, said intron, said open reading frame and said termination region, in a manner which allows expression and/or delivery of said nucleic acid molecule.

* * * * *

UNITED STATES PATENT AND TRADEMARK OFFICE
CERTIFICATE OF CORRECTION

| | | |
|---|---|---|
| PATENT NO. | : 6,831,171 B2 | Page 1 of 1 |
| APPLICATION NO. | : 09/780929 | |
| DATED | : December 14, 2004 | |
| INVENTOR(S) | : Ronald Breaker and Leonid Beigelman | |

It is certified that error appears in the above-identified patent and that said Letters Patent is hereby corrected as shown below:

Specification, Column 1, at line 4, insert

--STATEMENT REGARDING FEDERALLY SPONSORED RESEARCH DEVELOPMENT
This invention was made with government support under GM057500 awarded by National Institute of Health. The government has certain rights in the invention.--

Signed and Sealed this
Thirteenth Day of November, 2012

David J. Kappos
*Director of the United States Patent and Trademark Office*